United States Patent
Setoi et al.

[11] Patent Number: 5,521,170
[45] Date of Patent: May 28, 1996

[54] BENZAMIDE DERIVATIVES AND PHARMACEUTICAL COMPOSITION COMPRISING THE SAME

[75] Inventors: Hiroyuki Setoi, Tsukuba; Takehiko Ohkawa, Ishigemachi; Tatsuya Zenkoh, Toride; Keiji Hemmi, Tsukuba; Hirokazu Tanaka, Takarazuka, all of Japan

[73] Assignee: Fujisawa Pharmaceutical Co., Ltd., Osaka, Japan

[21] Appl. No.: 220,695

[22] Filed: Mar. 31, 1994

[30] Foreign Application Priority Data

Apr. 13, 1993 [GB] United Kingdom .................. 9307527

[51] Int. Cl.$^6$ .................. C07D 241/44; C07D 243/12; C07D 245/06; C07D 241/36
[52] U.S. Cl. .................. 514/183; 514/221; 514/249; 540/460; 540/517; 540/518; 544/354
[58] Field of Search .................. 540/517, 460, 540/518; 514/221, 183, 249; 544/354

[56] References Cited

U.S. PATENT DOCUMENTS

| | | | |
|---|---|---|---|
| 5,244,898 | 9/1993 | Ogawa et al. | 514/213 |
| 5,258,510 | 11/1993 | Ogawa et al. | 540/476 |

FOREIGN PATENT DOCUMENTS

| | | |
|---|---|---|
| 05320135 | 12/1993 | Japan . |
| 06157480 | 6/1994 | Japan . |
| WO94/20473 | 9/1994 | WIPO . |

OTHER PUBLICATIONS

Database WPI, Derwent Publications, WO 9401113,(Jan. 20, 1994), JP–175566, Jul. 2, 1992.
Database WPI, Derwent Publications, WO 9105–549, (May 2, 1991), JP–181858, Jul. 9, 1990.
Database WPI, Derwent Publications, EP 514667, Apr. 19,1991, JP–087994, Nov. 25, 1992.

*Primary Examiner*—Philip I. Datlow
*Attorney, Agent, or Firm*—Oblon, Spivak, McClelland, Maier & Neustadt

[57] ABSTRACT

Compounds having the structure below

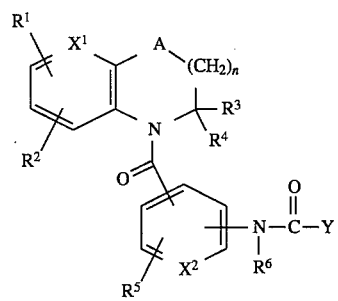

and pharmaceutically acceptable salts thereof exhibit vasopressin antagonistic activity, vasodilating activity, hypotensive activity, activity for inhibiting saccharide release in the liver, activity for inhibiting growth of mesagium cells, water diuretic activity, platelet agglutination inhibitory activity, oxytocin antagonistic activity and the like, and are useful in treating or preventing hypertension, heart failure, renal insufficiency, edema, ascites, vasopressin parasecretion syndrome, hepatocirrhosis, hyponatremia, hypokalemia, diabetic or circulation disorder, oxytocin related diseases and the like.

8 Claims, No Drawings

BENZAMIDE DERIVATIVES AND PHARMACEUTICAL COMPOSITION COMPRISING THE SAME

This invention relates to new benzamide derivatives and pharmaceutically acceptable salts thereof.

More particularly, it relates to new benzamide derivatives and pharmaceutically acceptable salts thereof which possess activities as vasopressin antagonistic activity, vasodilating activity, hypotensive activity, activity for inhibiting saccharide release in liver, activity for inhibiting growth of mesagium cells, water diuretic activity, platelet agglutination inhibitory activity, oxytocin antagonistic activity and the like, to a pharmaceutical composition comprising the same and to a method for the treatment and/or prevention of hypertension, heart failure, renal insufficiency, edema, ascites, vasopressin parasecretion syndrome, hepatocirrhosis, hyponatremia, hypokalemia, diabetic, circulation disorder, oxytocin relating diseases [e.g. premature delivery, dysmenorrhea, endometritis, etc.] and the like in human beings or animals.

One object of this invention is to provide new and useful benzamide derivatives which possess aforesaid activities.

Another object of this invention is to provide processes for the preparation of said benzamide derivatives and salts thereof.

A further object of this invention is to provide a pharmaceutical composition comprising, as an active ingredient, said benzamide derivatives and pharmaceutically acceptable salts thereof.

Still further object of this invention is to provide a therapeutical method for the treatment and/or prevention of aforesaid diseases in human beings or animals, using said benzamide derivatives and pharmaceutically acceptable salts thereof.

Some benzamide derivatives have been known as vasopressin antagonist or oxytocin antagonist, for example, in International Publication Nos. WO 91/05549 and WO 94/01113, and Japanese Patent Application Publication Nos. 5-132466 and 5-320135.

The object benzamide derivatives of this invention are new and can be represented by the following general formula (I):

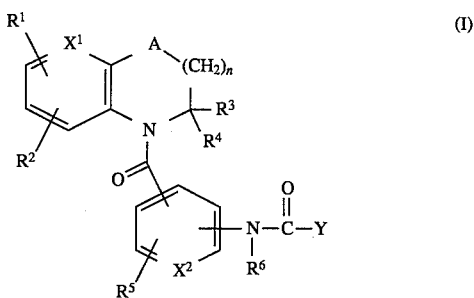

wherein $R^1$ is hydrogen or lower alkyl, $R^2$ is hydrogen, lower alkyl, halo(lower)alkyl, halogen or lower alkoxy, $R^3$ and $R^4$ are each hydrogen, lower alkyl or taken together to form oxo, $R^5$ is hydrogen, halogen, nitro, hydroxy, protected hydroxy, lower alkyl or lower alkoxy optionally substituted with lower alkylamino, $R^6$ is hydrogen, lower alkyl or acyl, A is

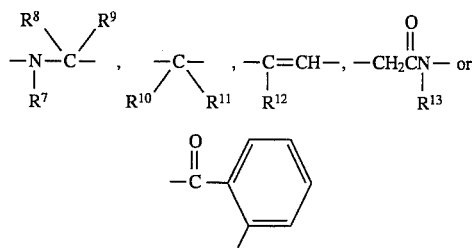

in which $R^7$ is hydrogen; lower alkyl optionally substituted with halogen, amino, lower alkylamino, protected amino, acyl, a heterocyclic group, hydroxy or protected hydroxy; or acyl; and $R^8$ and $R^9$ are each hydrogen, or taken together to form oxo or thioxo; or $R^7$ and $R^8$ are taken together to form a bond; and $R^9$ is lower alkylamino, N-lower alkylpiperazinyl or lower alkylthio optionally substituted with lower alkylamino;

$R^{10}$ is hydrogen;

$R^{11}$ is hydrogen, hydroxy, lower alkylamino or lower alkyl optionally substituted with acyl; or $R^{10}$ and $R^{11}$ are taken together to form oxo or lower alkoxyimino optionally substituted with acyl;

$R^{12}$ is lower alkyl optionally substituted with acyl; and $R^{13}$ is lower alkyl;

$X^1$ is CH or N, $X^2$ is CH or N,

Y is

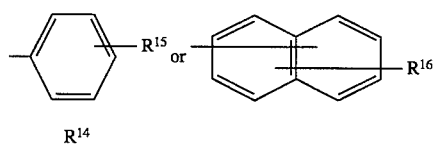

in which $R^{14}$ is hydrogen, halogen, hydroxy or lower alkoxy, $R^{15}$ is aryloxy, naphthyl, phenyl substituted with substituent(s) selected from the group consisting of lower alkyl, lower alkoxy, halogen, halo(lower)alkyl, hydroxy, amino(lower)alkyl, azido(lower)alkyl, lower alkylamino(lower)alkyl, acylamino(lower)alkyl, hydroxy(lower)alkyl, cyano and acyl, or a heterocyclic group, and $R^{16}$ is aryl and n is 0, 1, 2 or 3, and pharmaceutically acceptable salts thereof.

The object compound (I) or its salt can be prepared by the processes as illustrated in the following reaction schemes.
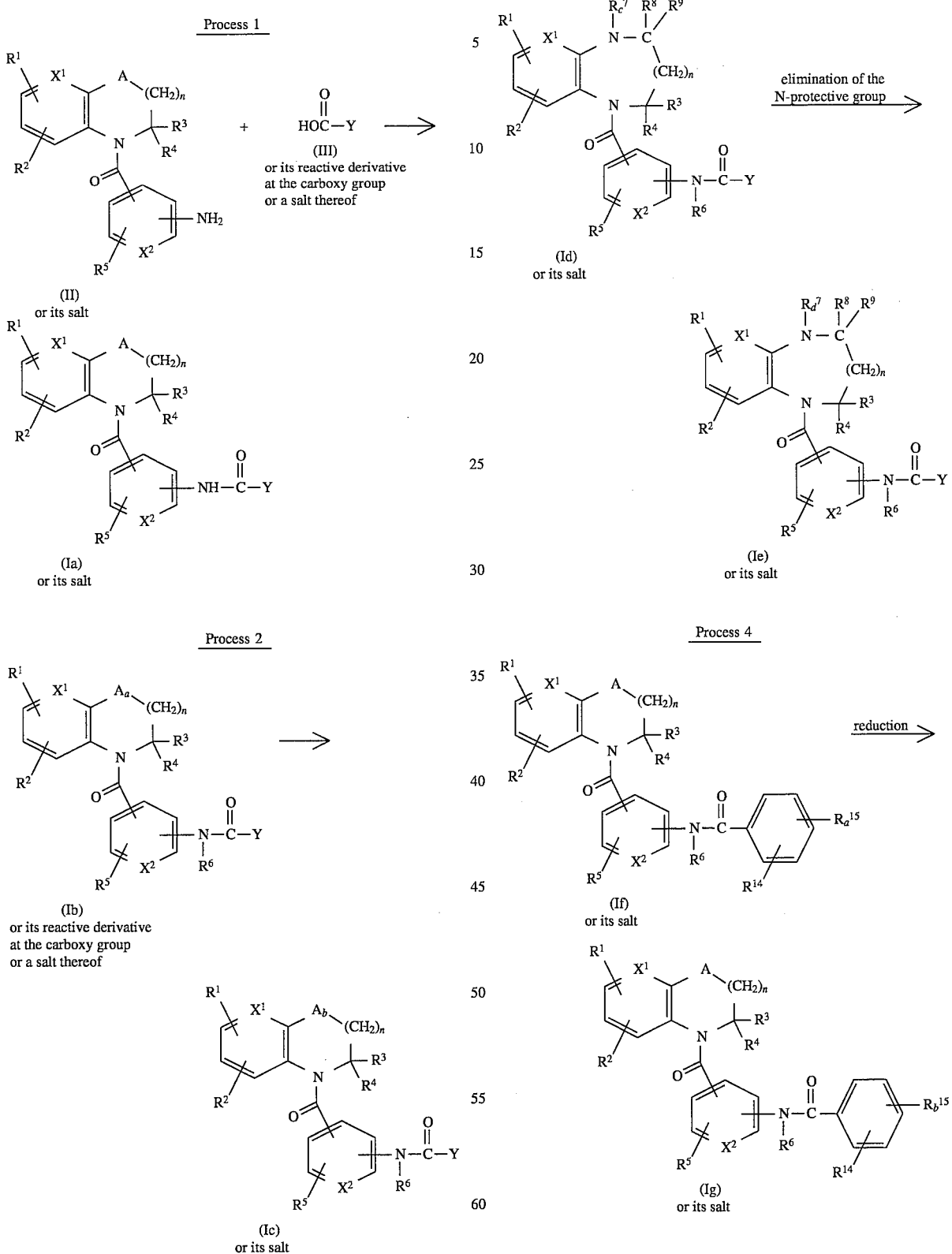

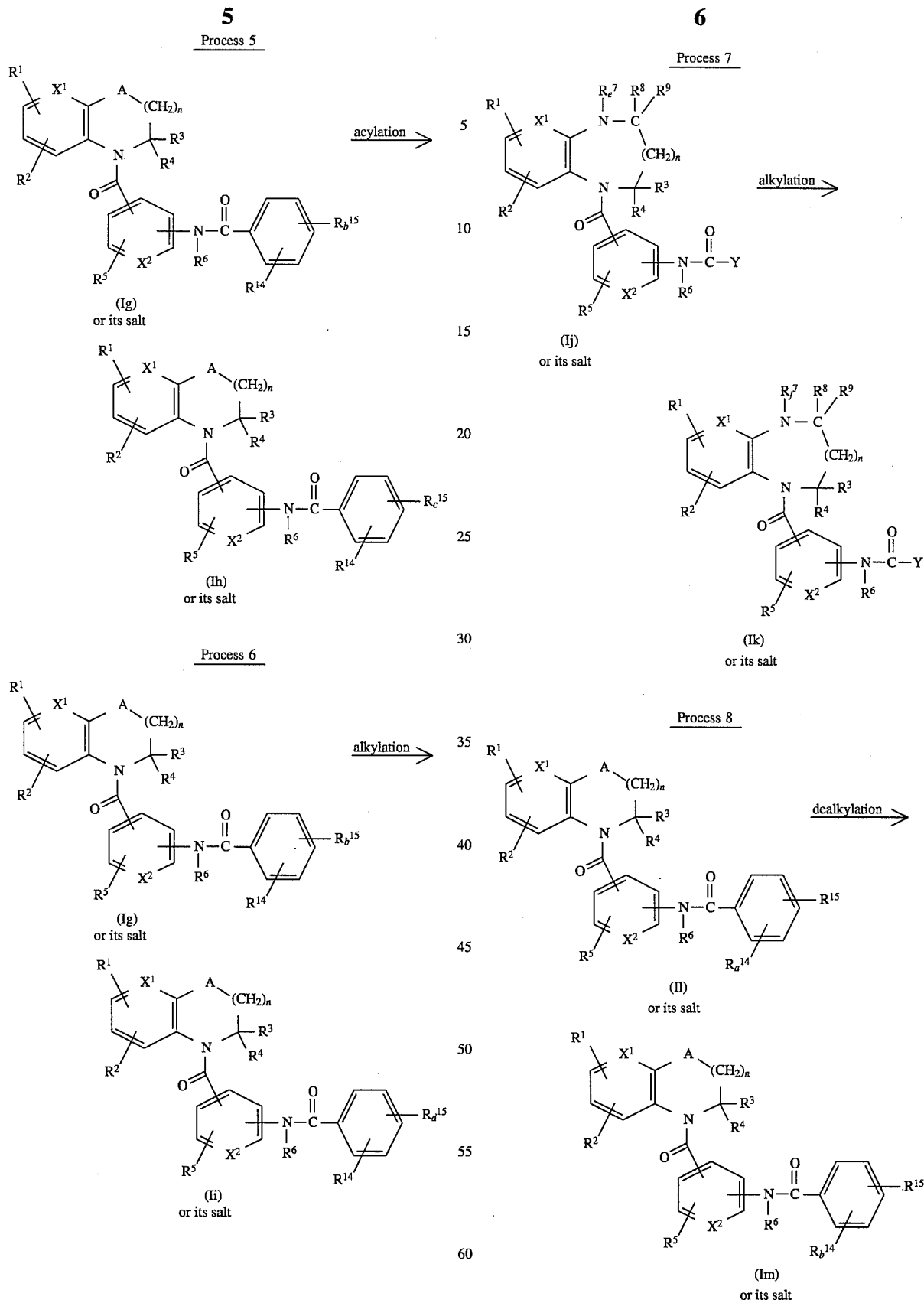

Process 9
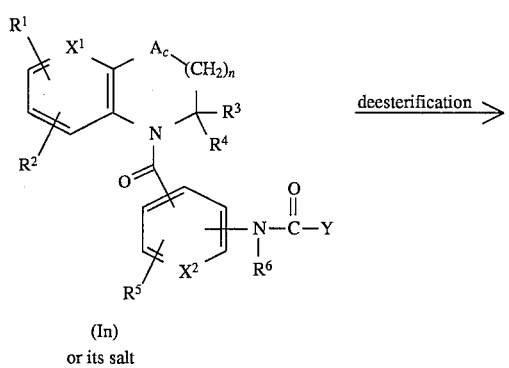
(In)
or its salt
deesterification →
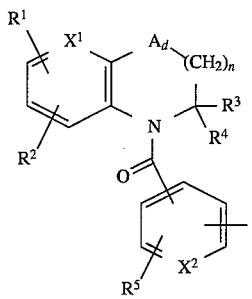
(Io)
or its salt
Process 10
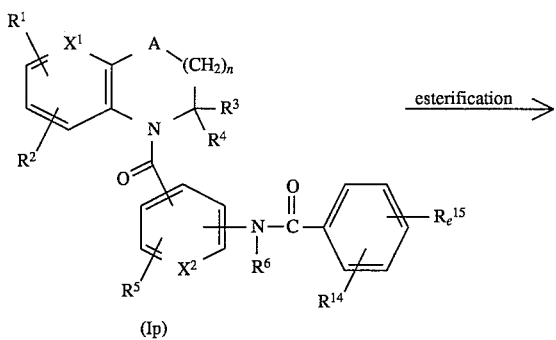
(Ip)
or its reactive derivative
at the carboxy group
or a salt thereof
esterification →
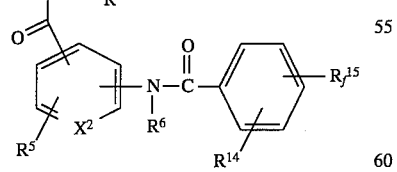
(Iq)
or its salt
Process 11
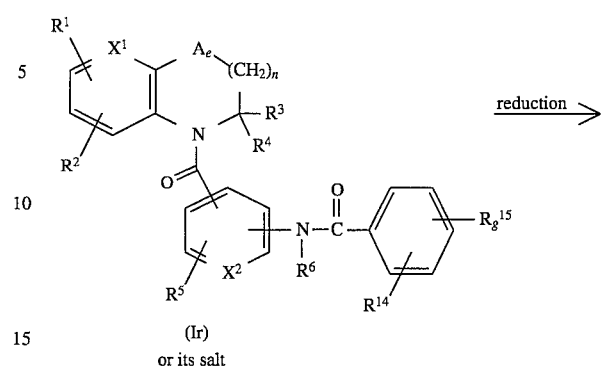
(Ir)
or its salt
reduction →
(Is)
or its salt
Process 12
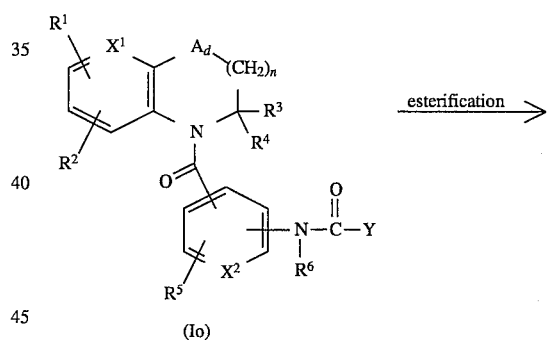
(Io)
or its reactive derivative
at the carboxy group
or a salt thereof
esterification →
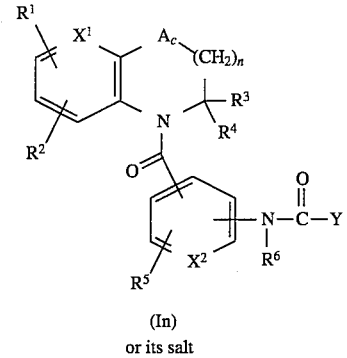
(In)
or its salt Process 13
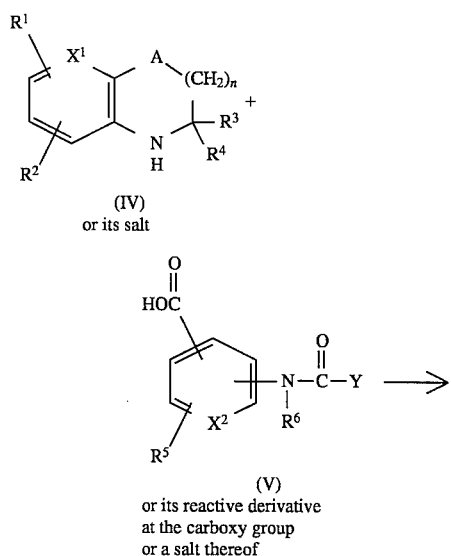
Process 14
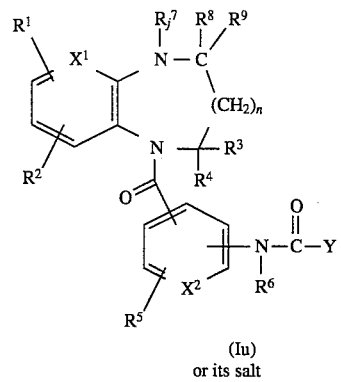
Process 14
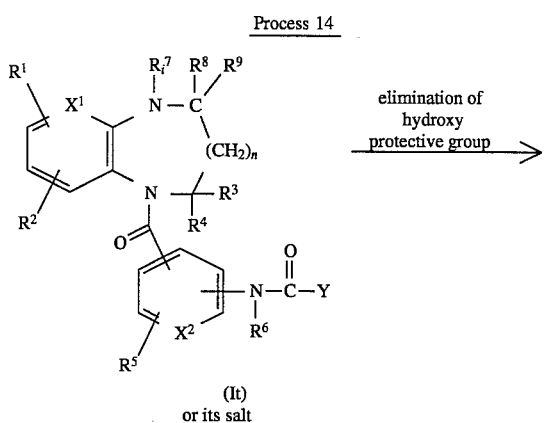
Process 15
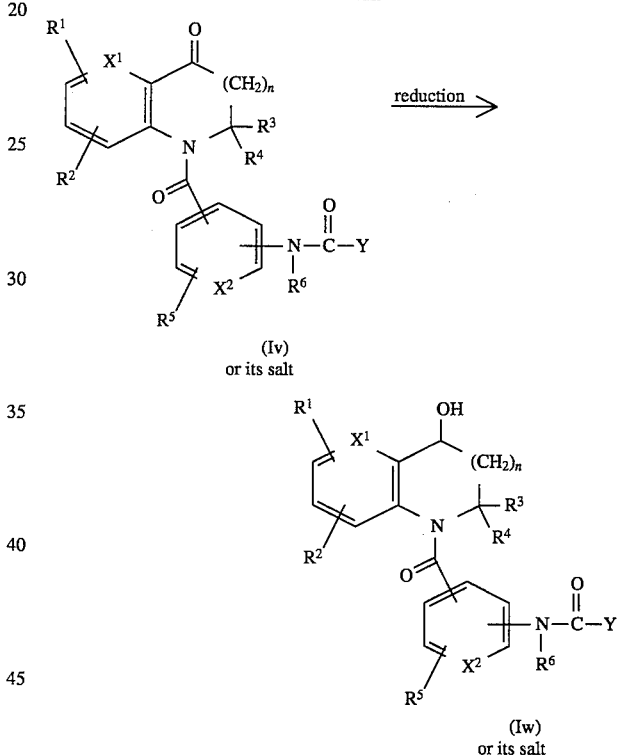
Process 16
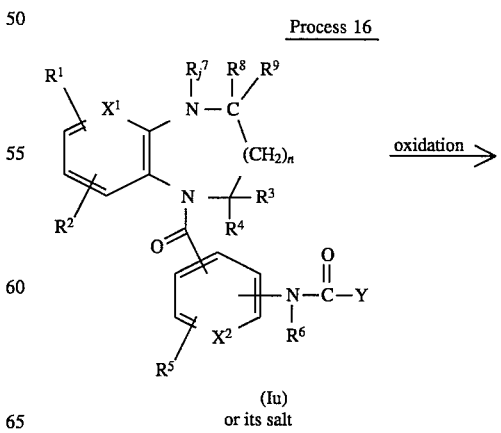

11
-continued
Process 16
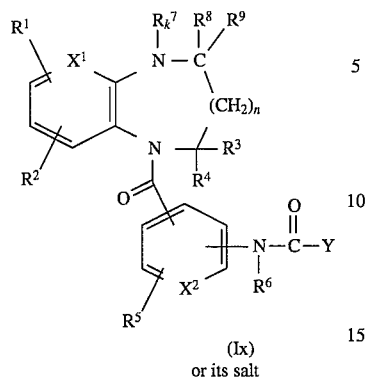
(Ix)
or its salt
Process 17
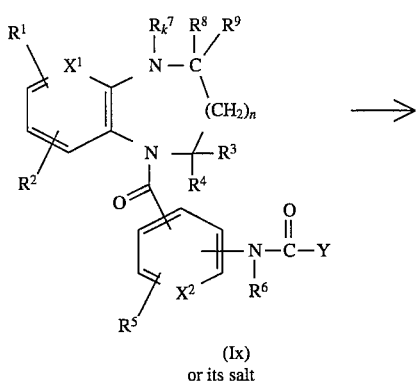
(Ix)
or its salt
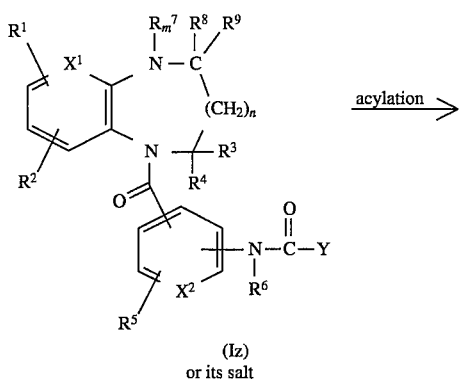
(Iy)
or its salt
Process 18
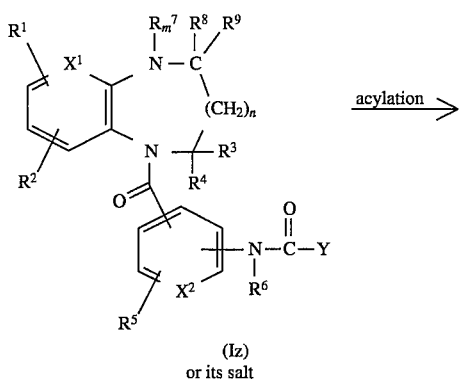
(Iz)
or its salt
12
-continued
Process 18
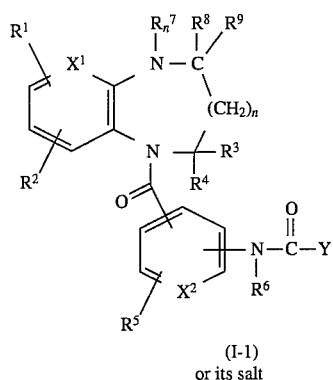
(I-1)
or its salt
Process 19
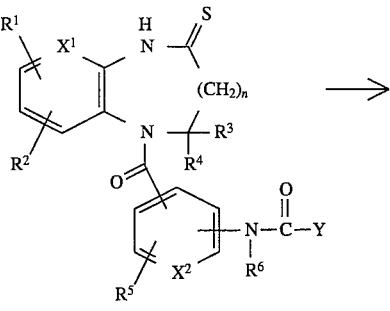
(I-2)
or its salt
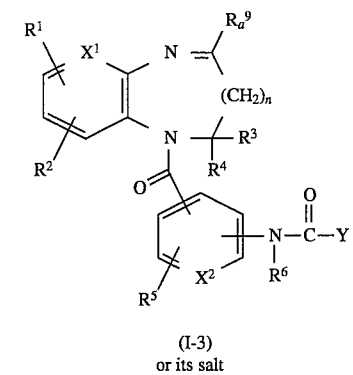
(I-3)
or its salt
Process 20
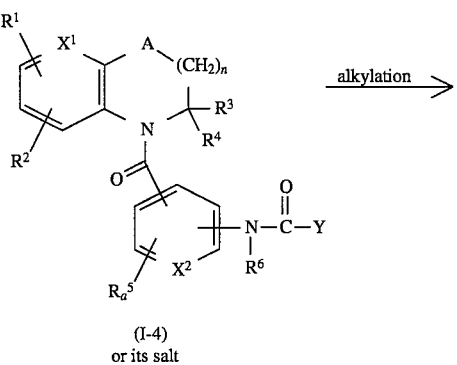
(I-4)
or its salt -continued
Process 20

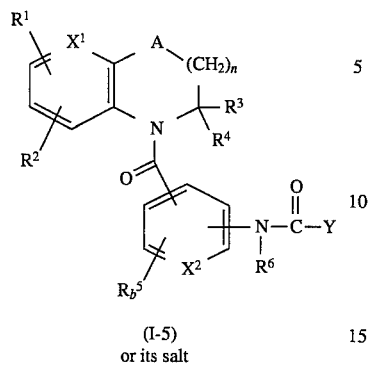

(I-5)
or its salt

Process 21

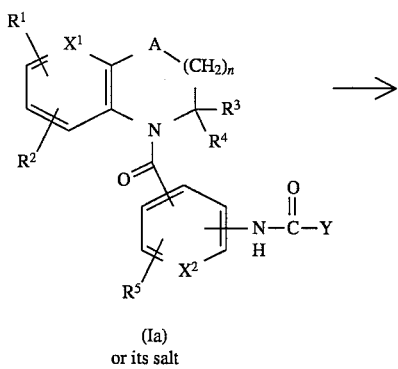

(Ia)
or its salt

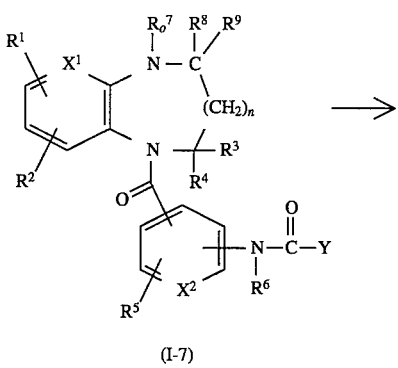

(I-6)
or its salt

Process 22

(I-7)
or its salt

-continued
Process 22

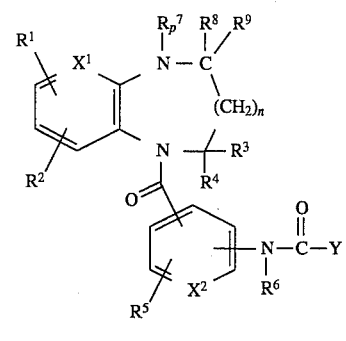

(I-8)
or its salt wherein $R^1$, $R^2$, $R^3$, $R^4$, $R^5$, $R^6$, A, $X^1$, $X^2$, Y and n are each defined above,

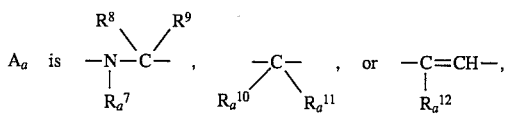

in which
$R^8$ and $R^9$ are each as defined above;
$R_a^7$ is lower alkyl substituted with carboxy;
$R_a^{10}$ is hydrogen,
$R_a^{11}$ is lower alkyl substituted with carboxy; or
$R_a^{10}$ and $R_a^{11}$ are taken together to form lower alkoxyimino substituted with carboxy; and
$R_a^{12}$ is lower alkyl substituted with carboxy;
$A_b$ is

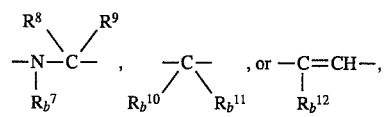

in which
$R^8$ and $R^9$ are each as defined above;
$R_b^7$ is lower alkyl substituted with carbamoyl which may be substituted with lower alkyl, lower alkylamino(lower)alkyl, a heterocyclic(lower)alkyl, acyl(lower)alkyl, lower alkylamino or a heterocyclic group, or an N-containing heterocycliccarbonyl;
$R_b^{10}$ is hydrogen,
$R_b$ is lower alkyl substituted with carbamoyl which may be substituted with lower alkyl, lower alkylamino(lower)alkyl, a heterocyclic(lower)alkyl, acyl(lower)alkyl, lower alkylamino or a heterocyclic group, or an N-containing heterocycliccarbonyl; or
$R_b^{10}$ and $R_b^{11}$ are taken together to form lower alkoxyimino substituted with carbamoyl which may be substituted with lower alkyl, lower alkylamino(lower)alkyl, a heterocyclic(lower)alkyl, acyl(lower)alkyl, lower alkylamino or a heterocyclic group, or an N-containing heterocycliccarbonyl; and
$R_b^{12}$ is lower alkyl substituted with carbamoyl which may be substituted with lower alkyl, lower alkylamino(lower)alkyl, a heterocyclic(lower)alkyl, acyl(lower)alkyl, lower alkylamino or a heterocyclic group, or an N-containing heterocycliccarbonyl;

$R_c^7$ is lower alkyl substituted with protected amino or N-protected piperazinylcarbonyl, $R_d^7$ is lower alkyl substituted with amino or piperazinylcarbonyl, $R_a^{15}$ is phenyl substituted with azido(lower)alkyl, $R_b^{15}$ is phenyl substituted with amino(lower)alkyl, $R_c^{15}$ is phenyl substituted with acylamino(lower)alkyl, $R_d^{15}$ is phenyl substituted with lower alkylamino(lower)alkyl, $R_e^7$ is lower alkyl substituted with amino, $R_f^7$ is lower alkyl substituted with lower alkylamino, $R_a^{14}$ is lower alkoxy, $R_b^{14}$ is hydroxy, $A_c$ is

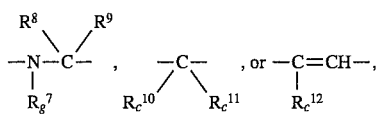

in which $R^8$ and $R^9$ are each as defined above;

$R_g^7$ is lower alkyl substituted with esterified carboxy or N-[esterified carboxy(lower)alkyl]piperazinylcarbonyl;

$R_c^{10}$ is hydrogen, $R_c^{11}$ is lower alkyl substituted with esterified carboxy; or $R_c^{10}$ and $R_c^{11}$ are taken together to form lower alkoxyimino substituted with esterified carboxy; and $R_c^{12}$ is lower alkyl substituted with esterified carboxy;

$A_d$ is

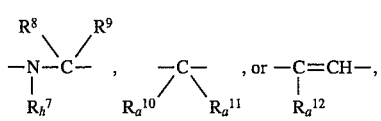

in which $R^8$, $R^9$, $R_a^{10}$, $R_a^{11}$ and $R_a^{12}$ are each as defined above, $R_h^7$ is lower alkyl substituted with carboxy or N-[carboxy(lower)alkyl]piperazinylcarbonyl, $R_e^{15}$ is phenyl substituted with carboxy, $R_f^{15}$ is phenyl substituted with esterified carboxy, $A_e$ is

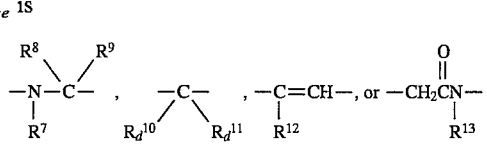

in which $R^7$, $R^8$, $R^9$, $R^{12}$ and $R^{13}$ are each as defined above, $R_d^{10}$ and $R_d^{11}$ are taken together to form lower alkoxyimino optionally substituted with acyl, $R_g^{15}$ is phenyl substituted with carboxy or esterified carboxy, $R_h^{15}$ is phenyl substituted with hydroxymethyl, $R_i^7$ is lower alkyl substituted with protected hydroxy, $R_j^7$ is lower alkyl substituted with hydroxy, $R_k^7$ is lower alkyl substituted with formyl, $R_l^7$ is lower alkyl substituted with di(lower)alkylamino or N-containing heterocyclic group, $R_m^7$ is lower alkyl substituted with N-[hydroxy-(lower)alkyl] piperazinylcarbonyl, $R_n^7$ is lower alkyl substituted with N-[acyloxy(lower)alkyl] piperazinylcarbonyl, $R_a^9$ is lower alkylthio optionally substituted with lower alkylamino, $R_a^5$ is hydroxy, $R_b^5$ is lower alkoxy optionally substituted with lower alkylamino, $R_a^6$ is lower alkyl or acyl, $R_o^7$ is lower alkyl substituted with N-lower alkylpiperazinylcarbonyl, and $R_p^7$ is lower alkyl substituted with N,N-di(lower alkyl)piperaziniocarbonyl.

In the above and subsequent description of the present specification, suitable examples of the various definitions to be included within the scope of the invention are explained in detail in the following.

The term "lower" is intended to mean a group having 1 to 6 carbon atom(s), preferably one having 1 to 4 carbon atom(s), unless otherwise provided.

Suitable "lower alkyl" and lower alkyl moiety in the terms "halo(lower)alkyl", "amino(lower)alkyl", "N-lower alkylpiperazinyl", "lower alkylthio", "N-[esterified carboxy(lower)alkyl]piperazinylcarbonyl", "N-[carboxy(lower)alkyl]piperazinylcarbonyl", "N-[hydroxy(lower)alkyl] piperazinylcarbonyl", "N-[acyloxy(lower)alkyl] piperazinylcarbonyl", "N-lower alkylpiperazinylcarbonyl", "N,N-di(lower alkyl)piperaziniocarbonyl", "a heterocyclic (lower) alkyl", "N-[amino(lower)alkyl]piperazinylcarbonyl", "N-[protected amino(lower)alkyl]piperazinylcarbonyl", "lower alkylsulfonyl", "azido(lower)alkyl", "lower alkylamino(lower)alkyl", "acylamino(lower)alkyl", "hydroxy(lower)alkyl", "lower alkylcarbamoyl", "acyl(lower)alkyl" and "lower alkylamino" may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "aryl" and aryl moiety in the terms "aryloxy" and "arylsulfonyl" may be phenyl, naphthyl, phenyl substituted with lower alkyl [e.g. tolyl, xylyl, mesityl, cumenyl, di(tert-butyl)phenyl, etc.] and the like, in which preferable one is phenyl or tolyl.

Suitable "halogen" may be fluorine, chlorine, bromine and iodine, in which preferable one is fluorine or chlorine.

Suitable "lower alkoxy" and lower alkoxy moiety in the term "lower alkoxyimino" may be methoxy, ethoxy, propoxy, isopropoxy, butoxy and the like, in which preferable one is methoxy or propoxy.

Suitable "lower alkylamino" may be mono or di(lower alkyl) amino such as methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is dimethylamino.

Suitable "lower alkylamino(lower)alkyl" may be mono or di(lower alkyl)amino substituted lower alkyl such as methylaminomethyl, methylaminoethyl, methylaminopropyl, methylaminobutyl, methylaminohexyl, ethylaminomethyl, ethylaminoethyl, ethylaminopropyl, ethylaminobutyl, ethylaminohexyl, dimethylaminomethyl, dimethylaminoethyl, dimethylaminopropyl, dimethylaminobutyl, dimethylaminohexyl, diethylaminomethyl, diethylaminoethyl, diethylaminopropyl, diethylaminobutyl, diethylaminohexyl or the like, in which preferable one is dimethylaminoethyl, dimethylaminopropyl or dimethylaminobutyl.

Suitable "halo(lower)alkyl" may be chloromethyl, fluoromethyl, bromomethyl, difluoromethyl, dichloromethyl, trifluoromethyl, trichloromethyl, 2-fluoroethyl and the like, in which preferable one is trifluoromethyl.

Suitable "heterocyclic group" and a heterocyclic moiety in the terms "a heterocyclic(lower)alkyl" and "a heterocycliccarbonyl" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 7-membered heteromonocyclic group containing 1 to 4 nitrogen atoms [e.g. pyrrolidinyl, imidazolidinyl, piperidyl, piperazinyl, homopiperazinyl, etc.]; saturated heteropolycyclic group containing 1 to 4 nitrogen atoms, for example, quinuclidinyl, etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.; unsaturated 3 to 6-membered heteromonocyclic group containing an oxygen atom, for example, pyranyl, furyl, etc.; unsaturated, 3 to 6-membered heteromonocyclic group containing 1 to 2 sulfur atoms, for example, thienyl, etc.; unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.; saturated 3 to 6-membered heteromonocyclic group containing 1 to 2 oxygen atoms and 1 to 3 nitrogen atoms [e.g. morpholinyl, etc.]; unsaturated condensed heterocyclic group containing 1 to 2 oxygen atoms and 1 to 3 nitrogen atoms [e.g. benzofurazanyl, benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.; saturated 3 to 6-membered heteromonocyclic group containing 1 to 2 sulfur atoms and 1 to 3 nitrogen atoms [e.g., thiazolidinyl, etc.]; unsaturated condensed heterocyclic group containing 1 to 2 sulfur atoms and 1 to 3 nitrogen atoms [e.g., benzothiazolyl, benzothiadiazolyl, etc.]; unsaturated condensed heterocyclic group containing 1 to 2 oxygen atoms [e.g. benzofuranyl, benzodioxolyl, etc.] and the like.

Said "heterocyclic group" may be substituted with lower alkyl optionally substituted with hydroxy, acyloxy, amino, protected amino, acyl, aryl or methylenedioxyphenyl; acyl or a heterocyclic group, in which preferable one is piperazinyl, N-methylpiperazinyl, N,N-dimethylpiperazinio, N-methylhomopiperazinyl, N-(2-hydroxyethyl)piperazinyl, N-(2-acetoxyethyl)piperazinyl, N-(3-phthalimidopropyl)piperazinyl, N-(3-aminopropyl)piperazinyl, N-(pyrrolidinylcarbonylmethyl)piperazinyl, N-(methylenedioxyphenylmethyl)piperazinyl, N-ethoxycarbonylpiperazinyl, N-carboxypiperazinyl, N-tert-butoxycarbonylpiperazinyl, N-pyridylpiperazinyl, dimethylaminopiperidyl, pyrrolyl, pyridyl, piperidyl, morpholinyl or quinuclidinyl.

Suitable "acyl" and acyl moiety in the terms "acylamino(lower)alkyl", "acyl(lower)alkyl" and "N-[acyloxy(lower)alkyl]piperazinylcarbonyl" may be carboxy, esterified carboxy, carbamoyl, lower alkylcarbamoyl, lower alkanoyl, aroyl, a heterocycliccarbonyl, lower alkylsulfonyl, arylsulfonyl and the like.

The esterified carboxy may be substituted or unsubstituted lower alkoxycarbonyl [e.g. methoxycarbonyl, ethoxycarbonyl, propoxycarbonyl, butoxycarbonyl, tert-butoxycarbonyl, hexyloxycarbonyl, 2-(dimethylamino)ethoxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is lower alkoxycarbonyl or 2-(dimethylamino)ethoxycarbonyl.

The lower alkylcarbamoyl may be mono or di(lower)alkylcarbamoyl such as methylcarbamoyl, ethylcarbamoyl, propylcarbamoyl, dimethylcarbamoyl, diethylcarbamoyl, N-methyl-N-ethylcarbamoyl or the like.

The lower alkanoyl may be substituted or unsubstituted one such as formyl, acetyl, propionyl, butyryl, isobutyryl, valeryl, isovaleryl, pivaloyl, hexanoyl, trifluoroacetyl or the like, in which preferable one is formyl or acetyl.

The aroyl may be substituted or unsubstituted one such as benzoyl, naphthoyl, toluoyl, di(tert-butyl)benzoyl, tolylbenzoyl, aminobenzoyl, tolylbenzoylaminobenzoyl and the like.

The N-containing heterocyclic moiety in the term "an N-containing heterocycliccarbonyl" may be one containing at least one nitrogen atom mentioned above, in which preferable one is piperazinylcarbonyl, N-methylpiperazinylcarbonyl, N,N-dimethylpiperaziniocarbonyl, N-methylhomopiperazinylcarbonyl, N-(2-hydroxyethyl)piperazinylcarbonyl, N-(2-acetoxyethyl)piperazinylcarbonyl, N-(3-phthalimidopropyl)piperazinylcarbonyl, N-(3-aminopropyl)piperazinylcarbonyl, N-(pyrrolidinylcarbonylmethyl)piperazinylcarbonyl, N-(methylenedioxyphenylmethyl)piperazinylcarbonyl, N-ethoxycarbonylpiperazinylcarbonyl, N-carboxypiperazinylcarbonyl, and N-tert-butoxycarbonylpiperazinylcarbonyl.

The lower alkylsulfonyl may be methylsulfonyl, ethylsulfonyl, propylsulfonyl, butylsulfonyl and the like.

The arylsulfonyl may be substituted or unsubstituted one such as phenylsulfonyl, tolylsulfonyl, dimethoxyphenylsulfonyl or the like, in which preferable one is dimethoxyphenylsulfonyl.

"N-Protective group" in "protected amino" may be common N-protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkoxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like, in which preferable one is phthaloyl or tert-butoxycarbonyl.

"N-Protective group" in "N-protected piperazinylcarbonyl" may be common N-protective group such as substituted or unsubstituted lower alkanoyl [e.g. formyl, acetyl, propionyl, trifluoroacetyl, etc.], lower alkoxycarbonyl [e.g. tert-butoxycarbonyl, tert-amyloxycarbonyl, etc.], substituted or unsubstituted aralkoxycarbonyl [e.g. benzoloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like, in which preferable one is tert-butoxycarbonyl.

"Protected hydroxy" may be commonly protected hydroxy such as substituted lower alkoxy such as lower alkoxy(lower)alkoxy [e.g. methoxymethoxy, etc.], lower alkoxy(lower)alkoxy(lower)alkoxy [e.g. methoxyethoxymethoxy, etc.], substituted or unsubstituted ar(lower)alkoxy [e.g. benzyloxy, nitrobenzyloxy, etc.], etc., acyloxy such as lower alkanoyloxy [e.g. acetoxy, propionyloxy, pivaloyloxy, etc.], aroyloxy [e.g. benzoyloxy, fluorenecarbonyloxy, etc.], lower alkoxycarbonyloxy [e.g. methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy, etc.], substituted or unsubstituted ar(lower)alkoxycarbonyloxy [e.g. benzyloxycarbonyloxy, bromobenzyloxycarbonyloxy, etc.] etc., tri(lower)alkylsilyloxy [e.g. trimethylsilyloxy, etc.] and the like.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

The phenyl group for $R^{15}$ may be substituted with 1 to 5 substituent(s) as mentioned above, wherein the preferable number of the substituent(s) is 1 to 2.

Preferable compound (I) is one which has hydrogen for $R^1$, hydrogen lower alkyl or halogen for $R^2$, hydrogen for $R^3$, hydrogen for $R^4$, hydrogen or lower alkoxy for $R^5$, hydrogen for $R^6$,

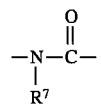

(wherein $R^7$ is lower alkyl optionally substituted with amino, lower alkylamino, protected amino, acyl or piperidino) or

(wherein $R^{11}$ is hydrogen, lower alkylamino or acyl(lower)alkyl) for A, CH for $X^1$, CH for $X^2$,

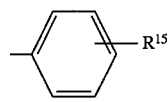

(wherein $R^{15}$ is phenyl substituted with substituent(s) selected from the group consisting of lower alkyl, lower alkoxy, halogen, halo(lower)alkyl, hydroxy, amino(lower)alkyl, azido(lower)alkyl, lower alkylamino(lower)alkyl, acylamino(lower)alkyl, hydroxy(lower)alkyl, cyano and acyl) for Y, and 0, 1 or 2 for n.

More preferable compound (I) is one which has hydrogen for $R^1$, hydrogen lower alkyl or halogen for $R^2$, hydrogen for $R^3$, hydrogen for $R^4$, hydrogen or lower alkoxy for $R^5$, hydrogen for $R^6$,

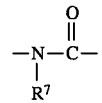

(wherein $R^7$ is lower alkyl substituted with N-lower alkylpiperazinylcarbonyl or lower alkyl substituted with di(lower)alkylamino) or

(wherein $R^{11}$ is lower alkyl substituted with N-lower alkylpiperazinylcarbonyl) for A, CH for $X^1$, CH for $X^2$,

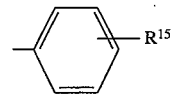

(wherein $R^{15}$ is phenyl substituted with lower alkyl or di(lower alkyl)) for Y, and 0, 1 or 2 for n.

Most preferable compound (I) is one which has hydrogen for $R^1$, hydrogen for $R^2$, hydrogen for $R^3$, hydrogen for $R^4$, hydrogen for $R^5$, hydrogen for $R^6$,

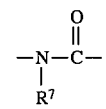

(wherein $R^7$ is lower alkyl substituted with N-lower alkylpiperazinylcarbonyl) for A, CH for $X^1$, CH for $X^2$,

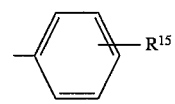

(wherein $R^{15}$ is phenyl substituted with lower alkyl or di(lower alkyl)) for Y, and 1 for n.

Suitable pharmaceutically acceptable salts of the object compound (I) are conventional non-toxic salts and include an acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a metal salt such as an alkali metal salt [e.g. sodium salt, potassium salt, etc.] and an alkaline earth metal salt [e.g. calcium salt, magnesium salt, etc.] and the like.

The processes for preparing the object compound (I) are explained in detail in the following.

PROCESS 1

The object compound (Ia) or its salt can be prepared by reacting a compound (II) or its salt with a compound (III) or its reactive derivative at the carboxy group or a salt thereof.

Suitable salts of the compounds (Ia), (II) and (III) and its reactive derivative at the carboxy group may be the same as those exemplified for the compound (I).

Suitable reactive derivative at the carboxy group of the compound (III) may include an acid halide, an acid anhydride containing intramolecular, intermolecular and a mixed ones, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.] or an ester with an N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; diphenyl chlorophosphate; diphenylphosphinic chloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro- 1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, 4-dimethylaminopyridine, N-(lower)alkylmorpholine, N,N-di(lower)alkylaniline (e.g. N,N-dimethylaniline, etc.) N,N-di(lower)alkylbenzylamine, or the like.

The reaction temperature is not critical, and the reaction is usually carried out under cooling to heating.

In this reaction, in case that the intramolecular acid anhydride (e.g. diphenic anhydride, etc.) is used as the reactive derivative at the carboxy group of the compound (III), the compound (Ia) having phenyl substituted with carboxy for $R^{15}$ may be obtained. In case that the compound (II) having aminobenzoyl for $R^7$ in A used as a starting compound, the compound (Ia) having aminobenzoyl, amino in which is substituted with

for R in A may be obtained. These cases are included within the scope of the present reaction.

PROCESS 2

The object compound (Ic) or its salt can be prepared by reacting a compound (Ib) or its reactive derivative at the carboxy group or a salt thereof with an amine.

Suitable salts of the compounds (Ic) and (Ib) and its reactive derivative at the carboxy group may be the same as those exemplified for the compound (I).

Suitable "amine" may be ammonia optionally substituted with lower alkyl, lower alkylamino(lower)alkyl, a heterocyclic(lower)alkyl, acyl(lower)alkyl, lower alkylamino or a heterocyclic group, N-containing heterocyclic compound and the like.

The ammonia substituted with lower alkyl, lower alkylamino(lower)alkyl, a heterocyclic(lower)alkyl, acyl(lower)alkyl, lower alkylamino or a heterocyclic group may be one substituted with those as illustrated above.

The N-containing heterocyclic compound may be saturated 5 to 7-membered N-, or N- and S-, or N- and O-containing heterocyclic compound such as pyrrolidine, imidazolidine, substituted or unsubstituted piperidine, substituted or unsubstituted piperazine, substituted or unsubstituted homopiperazine, morpholine, thiomorpholine, quinuclidine or the like, in which preferable one is piperazine, N-methylpiperazine, N-methylhomopiperazine, N-(2-hydroxyethyl)piperazine, N-(3-phthalimidopropyl)piperazine, N-(2-acetoxyethyl)piperazine, N-(pyrrolidinylcarbonylmethyl)piperazine, N-(methylenedioxyphenylmethyl)piperazine, N-ethoxycarbonylpiperazine, N-carboxypiperazine, N-tert-butoxypiperazine, N-pyridylpiperazine or dimethylaminopiperidine.

This reaction can be carried out in substantially the same manner as Process 1, and therefore the reaction mode and reaction condition (e.g. solvent, reaction temperature, etc.) of this reaction are to be referred to those as explained in Process 1.

PROCESS 3

The object compound (Ie) or its salt can be prepared by subjecting a compound (Id) or its salt to elimination reaction of the N-protective group.

Suitable salts of the compound (Id) and (Ie) may be the same as those exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non- 5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

PROCESS 4

The object compound (Ig) or its salt can be prepared by subjecting a compound (If) or its salt to reduction.

Suitable salts of the compounds (If) and (Ig) may be the same as those exemplified for the compound (I).

The reduction may include chemical reduction and catalytic reduction, which are carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, bonane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under cooling to heating.

PROCESS 5

The object compound (Ih) or its salt can be prepared by reacting a compound (Ig) or its salt with an acylating agent.

Suitable salt of the compound (Ig) may be the same as those exemplified for the compound (I).

Suitable salt of the compound (Ih) may be an acid addition salt as those exemplified for the compound (I).

The acylating agent may include an organic acid represented by the formula: $R^{17}$-OH, in which $R^{17}$ is acyl as illustrated above, or its reactive derivative.

The suitable reactive derivative of organic acid may be a conventional one such as an acid halide [e.g. acid chloride, acid bromide, etc.], an acid azide, an acid anhydride, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

PROCESS 6

The object compound (Ii) or its salt can be prepared by reacting a compound (Ig) or its salt with an alkylating agent.

Suitable salts of the compounds (Ig) and (Ii) may be the same as those exemplified for the compound (I).

Suitable alkylating agent may be lower alkyl halide [e.g. methyl iodide, ethyl bromide, etc.], a combination of a carbonyl compound such as aliphatic ketone [e.g. acetone, ethyl methyl ketone, etc.], carbaldehyde [e.g. formaldehyde, ethanal, etc.], orthocarboxylic acid ester [e.g. triethyl orthoformate, etc.] or the like, and a reducing agent including chemical and catalytic ones [e.g. formic acid, sodium borohydride, sodium cyanoborohydride, palladium on carbon, etc.].

When lower alkyl halide is used as alkylating agent, the reaction is preferably carried out in the presence of a base such as an alkali metal [e.g. sodium, potassium, etc.], an alkaline earth metal [e.g. magnesium, calcium, etc.], the hydride or hydroxide or carbonate or bicarbonate thereof, tri(lower)alkylamine, N,N-di(lower)alkylaniline, or the like.

The reaction is usually carried out in a conventional solvent which does not adversely influence the reaction such as water, dioxane, an alcohol [e.g. methanol, ethanol, etc.], acetonitrile, tetrahydrofuran, acetic acid, N,N-dimethylformamide, or a mixture thereof.

Additionally, in case that the above-mentioned alkylating agent or base is in liquid, it can also be used as a solvent.

The reaction temperature is not critical and the reaction can be carried out under cooling to heating.

In this reaction, in case that the compound (Ig) having lower alkyl substituted with amino for $R^7$ in A is used as a starting compound, the compound (Ii) having lower alkyl substituted with lower alkylamino for $R^7$ in A may be obtained according to reaction conditions. This case is included within the scope of the present reaction.

PROCESS 7

The object compound (Ik) or its salt can be prepared by reacting a compound (Ij) or its salt with an alkylating agent.

Suitable salts of the compounds (Ij) and (Ik) may be the same as those exemplified for the compound (I).

This reaction can be carried out in substantially the same manner as that of Process 6, and therefore the reaction mode and reaction condition (e.g. solvent, reaction temperature, etc.) of this reaction are to be referred to those as explained in Process 6.

In this reaction, in case that the compound (Ij) having phenyl substituted with amino(lower)alkyl for $R^{15}$ in Y is used as a starting compound, the compound (Ik) having phenyl substituted with lower alkylamino(lower)alkyl for R in Y may be obtained according to reaction condition. This case is included within the scope of the present reaction.

PROCESS 8

The object compound (Im) or its salt can be prepared by subjecting a compound (Il) or its salt to dealkylation reaction.

Suitable salts of the compounds (Il) and (Im) may be the same as those exemplified for the compound (I).

The reaction is carried out in accordance with a conventional method such as hydrolysis or the like.

The hydrolysis is preferably carried out in the presence of an acid including Lewis acid [e.g. hydrochloric acid, hydrobromic acid, hydroiodic acid, boron tribromide, boron trichloride, etc.] or tri(lower)alkyl silyliodide [e.g. trimethylsilyliodide, etc.].

The reaction is usually carried out in a solvent such as water, acetic acid, methylene chloride, tetrahydrofuran, a mixture thereof or any other solvent which does not adversely influence the reaction.

The reaction temperature is not critical and the reaction is usually carried out under cooling to heating.

PROCESS 9

The object compound (Io) or its salt can be prepared by subjecting a compound (In) or its salt to deesterification reaction.

Suitable salts of the compounds (In) and (Io) may be the same as those exemplified for the compound (I).

The reaction is carried out in accordance with a conventional method such as hydrolysis, reduction or the like.

The hydrolysis is preferably carried out in the present of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non- 5-ene, 1,4-diazabicyclo[2.2.21-octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ethyl, methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalitic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, pallaidum black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

PROCESS 10

The object compound (Iq) or its salt can be prepared by reacting a compound (Ip) or its reactive derivative at the carboxy group or a salt thereof with a hydroxy compound.

Suitable salts of the compounds (Iq) and (Ip) and its reactive derivative at the carboxy group may be the same as those exemplified for the compound (I).

Suitable reactive derivative at the carboxy group of the compound (Ip) may be acid halide [e.g. acid chloride, acid bromide, etc.] and the like.

Suitable hydroxy compound may be an alcohol [e.g. methanol, ethanol, propanol, benzyl alcohol, 2-dimethylaminoethanol, etc.], phenol, naphthol and the like.

The reaction is usually carried out in a conventional solvent such as diethyl ether, tetrahydrofuran, dioxane, methylene chloride or any other organic solvent which does not adversely influence the reaction.

Additionally, in case that the above-mentioned hydroxy compound is in liquid, it can also be used as a solvent.

The reaction temperature is not critical and the reaction is usually carried out under cooling to heating.

When the compound (Ip) is used in a free acid form in the reaction, the reaction is preferably carried out in the presence of an acid or a conventional condensing agent as illustrated in Process 1.

Suitable acid may be an organic acid [e.g. formic acid, acetic acid, propionic acid, trifluoroacetic acid, trichloroacetic acid, etc.], an inorganic acid [e.g. hydrogen chloride, hydrochloric acid, hydrobromic acid, hydroiodic acid, sulfuric acid, etc.] and Lewis acid [e.g. boron tribromide, etc.].

In this reaction, in case that the reaction is carried out in the presence of a condensing agent, the reaction mode and reaction condition (e.g. solvent, reaction temperature) of this reaction are to be referred to those as explained in Process 1.

PROCESS 11

The object compound (Is) or its salt can be prepared by reacting a compound (Ir) or its salt with a reducing agent.

Suitable salts of the compounds (It) and (Is) may be the same as those exemplified for the compound (I).

Suitable reducing agent may be diborane, lithium aluminum hydride and the like.

The reaction is usually carried out in a conventional solvent such as diethyl ether, tetrahydrofuran or any other organic solvent which does not adversely influence the reaction.

The reaction temperature is not critical, and the reaction can be carried out under cooling to heating.

PROCESS 12

The object compound (In) or its salt can be prepared by reacting a compound (Io) or its reactive derivative at the carboxy group or a salt thereof with a hydroxy compound.

Suitable salts of the compound (In) and (Io) and its reactive derivative at the carboxy group may be the same as those exemplified for the compound (I).

Suitable reactive derivative at the carboxy group of the compound (Io) may be acid halide [e.g. acid chloride, acid bromide, etc.] and the like.

This reaction can be carried out in substantially the same manner as that of Process 10, and therefore the reaction mode and reaction condition (e.g. solvent, reaction temperature, etc.) of this reaction are to be referred to those as explained in Process 10.

PROCESS 13

The object compound (I) or its salt can be prepared by reacting a compound (IV) or its salt with a compound (V) or its reactive derivatives at the carboxy group or a salt thereof.

Suitable salts of the compounds (IV) and (V) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

PROCESS 14

The object compound (Iu) or its salt can be prepared by subjecting a compound (It) or its salt to elimination reaction of hydroxy protective group.

Suitable salts of the compounds (It) and (Iu) may be the same as those exemplified for the compound (I).

This reaction is carried out in accordance with a conventional method such as hydrolysis or the like.

The hydrolysis is preferably carried out in the present of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non- 5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ethyl, methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

PROCESS 15

The object compound (Iw) or its salt can be prepared by reacting a compound (Iv) or its salt with a reducing agent.

Suitable salts of the compound (Iv) and (Iw) may be the same as those exemplified for the compound (I).

Suitable reducing agent may be alkali metal borohydride [e.g. sodium borohydride, etc.] and the like.

The reaction is usually carried out in a conventional solvent such as an alcohol [e.g. methanol, ethanol, etc.], water or any other solvent which does not adversely influence the reaction, or a mixture thereof.

The reaction temperature is not critical, and the reaction can be carried out under cooling to heating.

PROCESS 16

The object compound (Ix) or its salt can be prepared by reacting a compound (Iu) or its salt with an oxidizing agent.

Suitable salts of the compounds (Iu) and (Ix) may be the same as those exemplified for the compound (I).

Suitable oxidizing agent may be dimethyl sulfoxide, a mixture of dimethyl sulfoxide and oxalyl chloride, and the like.

This reaction is preferably carried out in the presence of alkali metal iodide [e.g. sodium iodide, etc.] and alkali metal carbonate [e.g. sodium carbonate] or tri(lower)alkylamine [e.g. triethylamine, etc.].

The reaction is usually carried out in a solvent which does not adversely influence the reaction such as dimethoxyethane, dichloromethane or the like. Additionally in case that the above-mentioned oxidizing agent is in liquid, it can also be used as a solvent.

The reaction temperature is not critical and the reaction is carried out under cooling to heating.

PROCESS 17

The object compound (Iy) or its salt can be prepared by reacting a compound (Ix) or its salt with di(lower)alkylamine or N-containing heterocyclic compound in the presence of a reducing agent.

Suitable salts of the compounds (Ix) and (Iy) may be the same as those exemplified for the compound (I).

Suitable di(lower)alkylamine, lower alkyl in which may be the same and different, may be dimethylamine, diethylamine, N-methyl-N-ethylamine and the like.

Suitable N-containing heterocyclic compound may be one as exemplified in Process 3.

Suitable reducing agent may include chemical and catalytic one [e.g. formic acid, sodium borohydride, sodium cyanoborohydride, palladium on carbon, etc.].

The reaction is usually carried out in a conventional solvent which does not adversely influence the reaction such as water, dioxane, an alcohol [e.g. methanol, ethanol, etc.], acetonitrile, tetrahydrofuran, acetic acid, N,N-dimethylformamide, or a mixture thereof.

The reaction temperature is not critical and the reaction can be carried out under cooling to heating.

PROCESS 18

The object compound (I-1) or its salt can be prepared by subjecting a compound (Iz) or its salt to acylation reaction.

Suitable salts of the compounds (Iz) and (I-1) may be the same as those exemplified for the compound (I).

This reaction can be carried out in substantially the same manner as Process 5, and therefore the reaction mode and reaction condition (e.g. solvent, reaction temperature, etc.) of this reaction are to be referred to those as explained in Process 5.

PROCESS 19

The object compound (I-3) or its salt can be prepared by reacting a compound (I-2) or its salt with lower alkyl halide or its salt, lower alkyl in which may be substituted with lower alkylamino, in the presence of a base.

Suitable salts of the compounds (I-2) and (I-3) may be the same as those exemplified for the compound (I).

Suitable salts of lower alkyl halide, lower alkyl in which is substituted with lower alkylamino may be an acid addition salt as exemplified for the compound (I).

Suitable base may be alkali metal [e.g. lithium, sodium, potassium, etc.], the hydroxide or carbonate or bicarbonate thereof [e.g. sodium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like.

The reaction is also preferably carried out in the presence of alkali metal iodide [e.g. sodium iodide, potassium iodide, etc.] and the like.

This reaction is usually carried out in a conventional solvent such as tetrahydrofuran, dioxane, aromatic hydrocarbon [e.g. benzene, toluene, xylene, etc.], N,N-dimethylformamide, acetone, a mixture thereof, or any other solvent which does not adversely influence the reaction.

The reaction temperature is not critical, and the reaction is usually carried out under cooling to heating.

PROCESS 20

The object compound (I-5) or its salt can be prepared by reacting a compound (I-4) or its salt with lower alkyl halide or its salt, lower alkyl in which may be substituted with lower alkylamino, in the presence of a base.

Suitable salts of the compounds (I-4) and (I-5) may be the same as those exemplified for the compound (I).

Suitable salt of lower alkyl halide, lower alkyl in which is substituted with lower alkylamino may be an acid addition salt as exemplified for the compound (I).

This reaction can be carried out in substantially the same manner as Process 19, and therefore the reaction mode and the reaction condition [e.g. solvent, reaction temperature, etc.] of this reaction are to be referred to those explained in Process 19.

PROCESS 21

The object compound (I-6) or its salt can be prepared by reacting a compound (Ia) or its salt with an alkylating or acylating agent.

Suitable salts of the compounds (Ia) and (I-6) may be the same as those exemplified for the compound (I).

Suitable alkylating agent may be lower alkyl halide [e.g. methyl iodide, ethyl bromide, etc.] and the like.

Suitable acylating agent may be a reactive derivative of organic acid as illustrated in Process 5.

The reaction is preferably carried out in the presence of a base such as an alkali metal [e.g. sodium, potassium, etc.], an alkaline earth metal [e.g. magnesium, calcium, etc.], the hydride or hydroxide or carbonate or bicarbonate thereof, tri(lower)alkylamine, N,N-di(lower)alkylaniline, 4-di(lower)alkylaminopyridine [e.g. 4-dimethylaminopyridine, etc.], or the like.

The reaction is usually carried out in a conventional solvent such as acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction temperature is not critical, and the reaction is preferably carried out under cooling to heating.

PROCESS 22

The object compound (I-8) or its salt can be prepared by reacting a compound (I-7) or its salt with lower alkyl halide.

Suitable salt of the compound (I-7) may be an acid addition salt as exemplified for the compound (I).

Suitable salt of the compound (I-8) may be halide.

The reaction is usually carried out in a conventional solvent such as acetone, dioxane, chloroform, methylene chloride, acetonitrile, tetrahydrofuran or any other organic solvent which does not adversely influence the reaction, or a mixture thereof.

The reaction temperature is not critical, and the reaction is preferably carried out under cooling to heating.

The starting compounds (II), (IIa), (IVa), (IVb), (IVc) and (V) or a salt thereof can be prepared by the following processes.

Process A

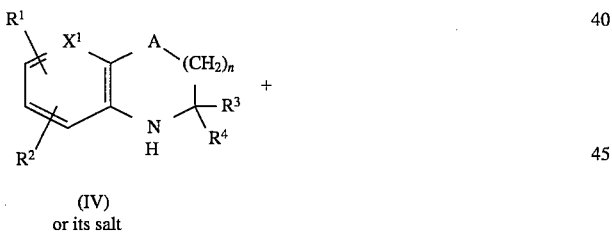

(IV)
or its salt

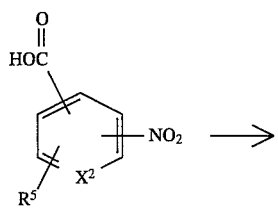

(VI)
or its reactive derivative
at the carboxy group
or a salt thereof

-continued
Process A

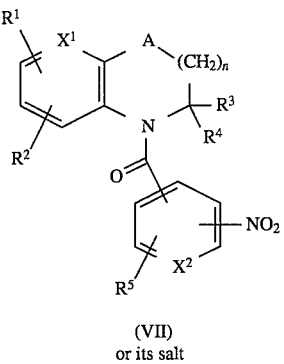

(VII)
or its salt

Process B

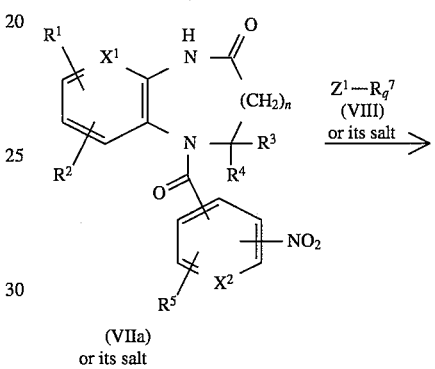

(VIIa)
or its salt $Z^1$—$R_q^7$
(VIII)
or its salt →

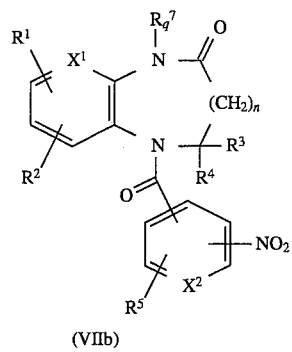

(VIIb)

Process C
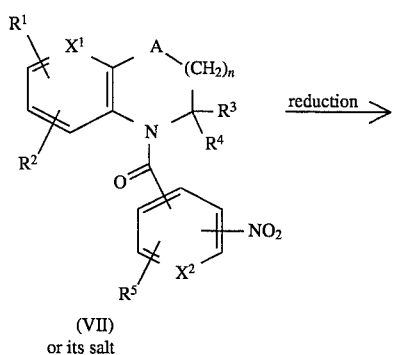
(VII)
or its salt
↓ reduction
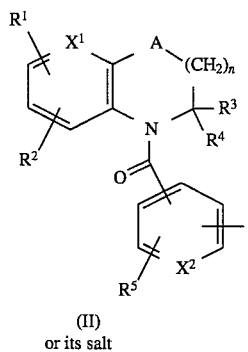
(II)
or its salt
Process D
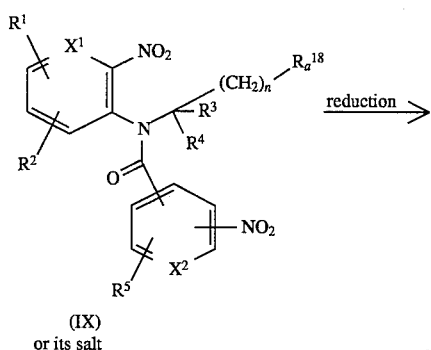
(IX)
or its salt
↓ reduction
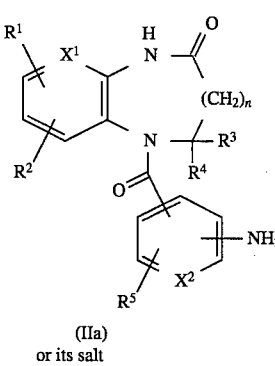
(IIa)
or its salt
Process E
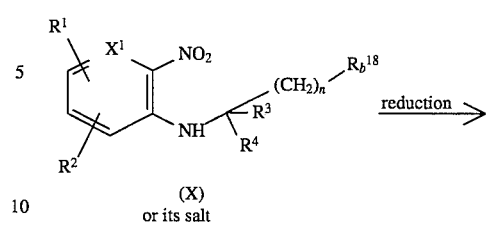
(X)
or its salt
↓ reduction
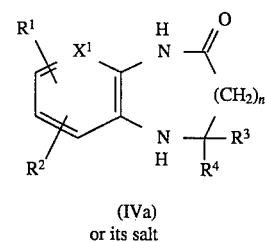
(IVa)
or its salt
Process F
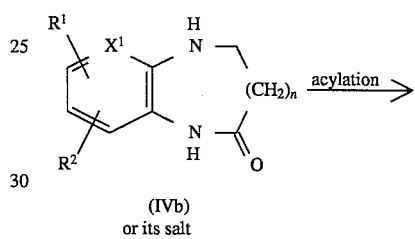
(IVb)
or its salt
↓ acylation
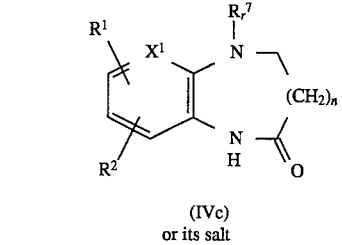
(IVc)
or its salt
Process G
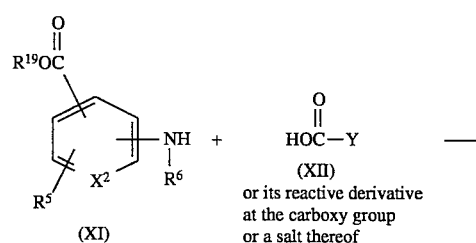
(XI)
or its salt
(XII)
or its reactive derivative
at the carboxy group
or a salt thereof
⟶
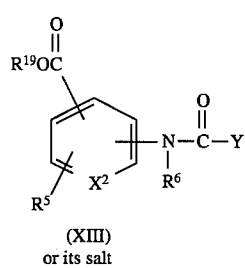
(XIII)
or its salt Process H

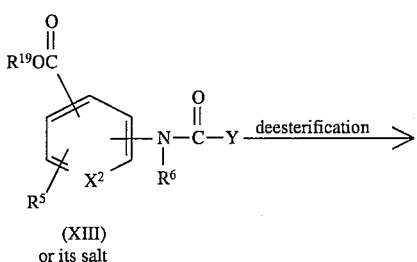

(XIII) or its salt deesterification →

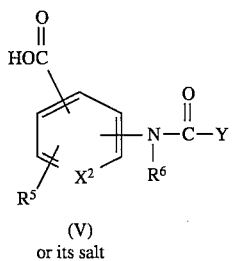

(V) or its salt

Process I

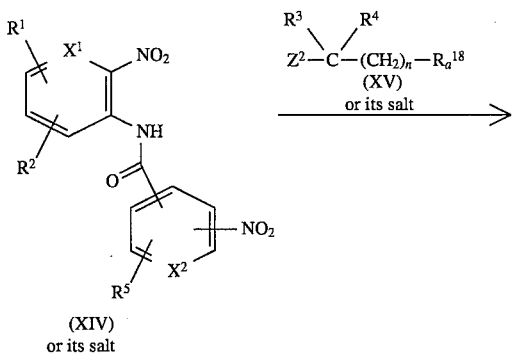

(XIV) or its salt

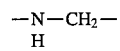
(XV) or its salt

→

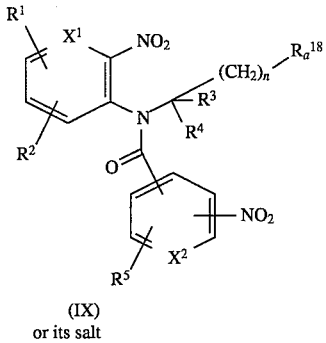

(IX) or its salt wherein $R^1$, $R^2$, $R^3$, $R^4$, $R^5$, $R^6$, A, $X^1$, $X^2$, Y and n are each as defined above, $R_q^7$ is lower alkyl optionally substituted with halogen, amino, lower alkylamino, protected amino, acyl, a heterocyclic group, hydroxy or protected hydroxy, $Z^1$ is acid residue, $R_a^{18}$ is carboxy or esterified carboxy, $R_b^{18}$ is carboxy or esterified carboxy, $R_r^7$ is acyl, $R_a^{19}$ is esterified carboxy, and $Z^2$ is acid residue.

The above-mentioned processes for preparing the starting compounds are explained in detail in the following.

PROCESS A

The compound (VII) or its salt can be prepared by reacting a compound (IV) or its salt with a compound (VI) or its reactive derivative at the carboxy group or a salt thereof.

Suitable salts of the compounds (IV) and (VII) may be the same as those exemplified for the compound (I).

Suitable salts of the compound (VI) and its reactive derivative at the carboxy group may be a base salt as exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

In this reaction, in case that the compound (IV) having $$-\underset{H}{N}-CH_2-$$

for A and nitrobenzoic acid as the compound (VI) are used as a starting compound, the compound having $$-\underset{R^7}{N}-CH_2-$$

(wherein $R^7$ is nitrobenzoyl) for A may be obtained according to reaction conditions. This case is included within the scope of the present reaction.

PROCESS B

The compound (VIIb) or its salt can be prepared by reacting a compound (VIIa) or its salt with a compound (VIII) or its salt.

Suitable salt of the compound (VIIa) may be an acid addition salt as exemplified for the compound (I).

Suitable salts of the compounds (VIIb) and (VIII) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

In this reaction, in case that the compound (VIII) having lower alkyl substituted with acyl for $R_q^7$ and chlorine for $Z^1$ [e.g. methyl chloroacetate, etc.] is used as a starting compound, the reaction is preferably carried out in the presence of an alkali metal iodide [e.g. sodium iodide, potassium iodide, etc.].

PROCESS C

The compound (II) or its salt can be prepared by subjecting a compound (VII) or its salt to reduction.

Suitable salts of the compounds (II) and (VII) may be the same as those exemplified for the compound (I).

This reaction can be carried out in substantially the same manner as Process 4, and therefore the reaction mode and reaction condition (e.g. solvent, reaction temperature, etc.) of this reaction are to be referred to those as explained in Process 4.

In this reaction, in case that the compound (VII) having

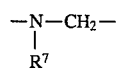

(wherein $R^7$ is nitrobenzoyl) for A is used as a starting compound, the compound (II) having

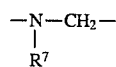

(wherein $R^7$ is aminobenzoyl) for A may be obtained according to reaction conditions. This case is included within the scope of the present reaction.

In this reaction, in case that the compound (VII) having protected hydroxy for $R^5$ is used as a starting compound, the compound (II) having hydroxy for $R^5$ may be obtained according to reaction conditions. This case is included within the scope of the present reaction.

PROCESS D

The compound (IIa) or its salt can be prepared by subjecting a compound (XI) or its salt to reduction.

Suitable salt of the compound (IIa) may be an acid addition salt as exemplified for the compound (I).

Suitable salt of the compound (IX) may be a base salt as exemplified for the compound (I).

This reaction can be carried out in substantially the same manner as Process 4, and therefore the reaction mode and reaction condition (e.g. solvent, reaction temperature, etc.) of this reaction are to be referred to those as explained in Process 4.

PROCESS E

The compound (IVa) or its salt can be prepared by subjecting a compound (X) or its salt to reduction.

Suitable salt of the compound (IVa) may be an acid addition salt as exemplified for the compound (I).

Suitable salt of the compound (X) may be the same as those exemplified for the compound (I).

This reaction can be carried out in substantially the same manner as Process 4, and therefore the reaction mode and reaction condition (e.g. solvent, reaction temperature, etc.) of this reaction are to be referred to those as explained in Process 4.

PROCESS F

The compound (IVc) or its salt can be prepared by reacting a compound (IVb) or its salt with an acylating agent.

Suitable salts of the compounds (IVb) and (IVc) may be acid addition salts as exemplified for the compound (I).

This reaction can be carried out in substantially the same manner as Process 5, and therefore the reaction mode and reaction condition (e.g. solvent, reaction temperature, etc.) of this reaction are to be referred to those as explained in Process 5.

PROCESS G

The compound (XIII) or its salt can be prepared by reacting a compound (XI) or its salt with a compound (XII) or its reactive derivative at the carboxy group or a salt thereof.

Suitable salt of the compound (XI) may be an acid addition salt as exemplified for the compound (I).

Suitable salts of the compounds (XIII) and (XII) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

In this reaction, in case that the compound (XI) having hydrogen for $R^6$ and the compound (XII) having tolylphenyl for Y are used as a starting compound, the compound (XIII) having tolylbenzoyl for R may be obtained according to reaction conditions. This case is included within the scope of this reaction.

PROCESS H

The compound (V) or its salt can be prepared by subjecting a compound (XIII) or its salt to deesterification reaction.

Suitable salts of the compounds (Vl and (XIII) may be the same as those exemplified for the compound (I).

This reaction can be carried out in substantially the same manner as Process 9, and therefore the reaction mode and reaction condition (e.g. solvent, reaction temperature, etc.) of this reaction are to be referred to those as explained in Process 9.

In this reaction, in case that the compound (XIII) having acyl for $R^6$ is used as a starting compound, the compound (V) having hydrogen for R may be obtained according to reaction conditions. This case is included the scope of the present reaction.

PROCESS I

The compound (IX) or its salt can be prepared by reacting a compound (XIV) or its salt with a compound (XV) or its salt.

Suitable salt of the compound (XIV) may be an acid addition salt as exemplified for the compound (I).

Suitable salt of the compound (XV) may be a base salt as exemplified for the compound (I).

Suitable salt of the compound (IX) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

The compounds obtained by the above processes can be isolated and purified by a conventional method such as pulverization, recrystallization, column chromatography, reprecipitation, or the like, and converted to desired salt in conventional manner, if necessary.

It is to be noted that the compound (I) and the other compounds may include one or more stereoisomer(s) such as optical isomer(s) and geometrical isomer(s) due to asymmetric carbon atoms and double bond(s), and all of such isomers and mixture thereof are included within the scope of this invention.

The object compound (I) and pharmaceutically acceptable salts thereof possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, and are useful for the treatment and/or prevention of hypertension, heart failure, renal insufficiency, edema, ascites, vasopressin parasecretion syndrome, hepatocirrhosis, hyponatremia, hypokalemia, diabetic, circulation disorder, oxytocin relating diseases [e.g. premature delivery, dysmenorrhea, endometritis, etc.] and the like in human beings and animals.

In order to illustrate the usefulness of the object compound (I), the pharmacological data of the compound (I) are shown in the following.

TEST 1

Vasopressin 1 (V1) receptor binding (i) Test Method:

The rat liver was dissected and homogenized in 10 volume of ice cold 250 mM sucrose buffer containing 25 mM Tris-HCl (pH 7.4), 5 mM $MgCl_2$ and 0.1 mM phenylmethylsulfonyl fluoride (PMSF). The homogenate was centrifuged at 1000 xg for 10 minutes. The supernatant fraction was separated and centrifuged at 45,000 xg for 30 minutes. The remaining pellet was resuspended in 10 volume of ice cold 100 mM Tris-HCl (pH 7.4) buffer (containing 5 mM $MgCl_2$, 0.1% bovine serum albumin and 0.1 mM PMSF), and centrifuged at 45,000 xg for 30 minutes again. The final pellet was resuspended in 100 mM Tris-HCl buffer. The resulting membrane preparation was used immediately for the binding assay.

Competition assays were conducted at equilibrium (60 minutes at 25° C.) by using 0.5 nM $^3$H-vasopressin ([phenylalanyl-3,4,5-$^3$H]-vasopression; 40–87 Ci/mmol; New England Nuclear) in 100 mM Tris-HCl (pH 7.4) buffer. Nonspecific binding was determined by using 1 µM $[d(CH_2)_5, Tyr^2(Me), Arg^8]$-vasopressin (Peptide institute, Japan). After incubation, reaction was terminated by adding 5 ml of ice-cold 100 mM Tris-HCl (pH 7.4) buffer, and then filtered rapidly through Whatman glass filter (GF/C). The filter was washed 2 times with the same buffer (5 ml). The glass filter was mixed with liquid scintillation cocktail, and radioactivity was counted in a liquid scintillation counter (TRI-CARB 4530, Packard). Competition activity of the test compound was represented by $IC_{50}$ values.

(ii) TEST RESULTS

| Test Compound (Example No.) | $IC_{50}$ (M) |
| --- | --- |
| 2-2) | $3.9 \times 10^{-9}$ |
| 2-21) | $4.4 \times 10^{-9}$ |

TEST 2

Vasopressin 2 (V2) receptor binding (i) Test Method:

The medullopapillary region of male rat kidey was dissected and homogenized in 10 volume of ice cold 250 mM sucrose buffer containing 25 mM Tris-HCl (pH 7.4), 5 mM $MgCl_2$ and 0.1 mM phenylmethylsulfonyl fluoride (PMSF). The homogenate was centrifuged at 500 xg for 5 minutes. The supernatant fraction was separated and centrifuged at 45,000 xg for 30 minutes. The remaining pellet was resuspended in 10 volume of ice cold 100 mM Tris-HCl (pH 7.4) buffer (containing 5 mM $MgCl_2$, 0.1% bovine serum albumin and 0.1 mM PMSF), and centrifuged at 45,000 xg for 30 minutes again. The final pellet was resuspended in 100 mM Tris-HCl buffer. The resulting membrane preparation was used immediately for the binding assay.

Competition assays were conducted at equilibrium (2 hours at. 25° C.) by using 0.5 nM $^3$H-vasopression ([phenylalanyl-3,4,5-3H]-vasopression; 40–87 Ci/mmol; New England Nuclear) in 100 mM Tris-HCl (pH 7.4) buffer. Nonspecific binding was determined by using 1 µM $[d(CH_2)_5, D\text{-Ile}^2 \text{Ile}^4 \text{Arg8}]$-vasopressin (Peninsula Laboratories USA). After incubation, reaction was terminated by adding 5 ml of ice-cold 100 mM Tris-HCl (pH 7.4) buffer, and then filtered rapidly through Whatman glass filter (GF/C). The filter was washed 2 times with the same buffer (5 ml). The glass filter was mixed with liquid scintillation cocktail, and radioactivity was counted in a liquid scintillation counter (TRI-CARB 4530, Packard). Competition activity of the test compound was represented by $IC_{50}$ values.

(ii) Test Results:

| Test Compound (Example No.) | $IC_{50}$ (M) |
| --- | --- |
| 2-4) | $3.0 \times 10^{-9}$ |
| 15 | $1.8 \times 10^{-9}$ |
| 16-3) | $2.3 \times 10^{-9}$ |
| 16-9) | $3.3 \times 10^{-9}$ |
| 16-14) | $2.7 \times 10^{-9}$ |
| 16-69) | $5.1 \times 10^{-9}$ |

For therapeutic purpose, the compound (I) of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical)administration. The pharmaceutical preparations may be capsules, tablets, dragees, granules, suppositories, solution, lotion, suspension, emulsion, ointment, gel, or the like. If desired, there may be include in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

In the following Preparations, Kieselgel Art. 5715 (Trademark: manufactured by E. Merck) (thickness: 0.25 mm) was used as TLC plate.

PREPARATION 1

To a solution of 1,3,4,5-tetrahydro-1,5-benzodiazepin-2(2H)-one (0.87 g) and triethylamine (0.55 g) in dichloromethane (5 ml) was added a solution of 4-nitrobenzoyl chloride (1.00 g) in dichloromethane (5 ml) at ambient temperature. After being stirred at ambient temperature for 2 hours, the solution was washed successively with 0.5N hydrochloric acid, saturated sodium bicarbonate aqueous solution, and brine. The organic layer was dried over magnesium sulfate, filtered and the solvents was evaporated. Trituration with a mixture of diethyl ether and diisopropyl ether (1:1) of a crude product afforded 5-(4-nitrobenzoyl)-1,3,4,5-tetrahydro-1,5-benzodiazepin-2(2H)-one (1.60 g) as a slightly brown powder.

mp: 225°–230° C.

PREPARATION 2

The following compounds were obtained according to a similar manner to that of Preparation 1.

1) 5-(4-Nitrobenzoyl)-1,3,4,5-tetrahydro-1,5-benzodiazepin- 2(2H)-one

NMR (CDCl$_3$, δ): 2.61–3.00 (2H, m), 3.90 (1H, br), 4.89 (1H, br), 6.71 (1H, d, J=8Hz), 6.90 (1H, t, J=8 Hz), 7.01–7.77 (2H, m), 7.35 (2H, d, J=8.5 Hz), 8.02 (2H, d, J=8.5 Hz), 8.52 (1H, s)

4-(4-Nitrobenzoyl)-1,2,3,4-tetrahydroquinoxalin-2-one

NMR (DMSO-d$_6$, δ): 4.43 (2H, s), 6.73 (2H, br), 7.00–7.16 (2H, m), 7.64 (2H, d, J=8.5 Hz), 8.20 (2H, d, J=8.5 Hz)

3) 4-(3-Methoxy-4-nitrobenzoyl)-1,2,3,4-tetrahydroquinoxalin- 2-one

NMR (CDCl$_3$, δ): 3.85 (3H, s), 4.62 (2H, s), 6.65 (1H, br), 6.83 (1H, ddd, J=9, 9, 1Hz), 6.94 (1H, dd, J=9, 1Hz), 7.02 (1H, dd, J=8, 1Hz), 7.10–7.21 (2H, m), 7.72 (1H, d, J=8 Hz), 9.35 (1H, s)

4) 7-Methyl-5-(4-nitrobenzoyl)-1,3,4,5-tetrahydro- 1,5-benzodiazepin-2(2H)-one

NMR (CDCl$_3$, δ): 2.05 (3H, s), 2.60–2.90 (2H, m), 3.80–3.93 (1H, br), 4.78–4.98 (1H, br), 6.52 (1H, s), 7.02 (2H, s), 7.37 (2H, d, J=10Hz), 8.03 (2H, d, J=10Hz), 8.07–8.17 (1H, br s)

5) 8-Chloro-5-(4-nitrobenzoyl)-1,3,4,5-tetrahydro-1,5-benzodiazepin- 2(2H)-one

NMR (CDCl$_3$, δ): 2.70–2.86 (2H, m), 3.80–3.95 (1H, br), 4.75–4.96 (1H, br), 6.67 (1H, d, J=9Hz), 6.89 (1H, dd, J=1, 9Hz), 7.16 (1H, d, J=1 Hz), 7.38 (2H, d, J=9Hz), 8.07 (3H, d, J=9Hz)

6) 8-Methyl-5-(4-nitrobenzoyl)-1,3,4,5-tetrahydro-1,5-benzodiazepin- 2(2H)-one

NMR (CDCl$_3$, δ): 2.30 (3H, s), 2.60–2.92 (2H, m), 3.78–3.95 (1H, m), 4.77–4.97 (1H,m), 6.59 (1H, d, J=8Hz), 6.69 (1H, d, J=8Hz), 6.94 (1H, s), 7.36 (2H, d, J=9Hz), 8.03 (2H, d, J=9Hz), 8.26–8.32 (1H, br s)

7) 8-Methoxy-5-(4-nitrobenzoyl)-1,3,4,5-tetrahydro-1,5-benzodiazepin-2(2H)-one

NMR (CDCl$_3$, δ): 2.60–2.74 (1H, m), 2.75–2.92 (1H, m), 3.77 (3H, s), 3.85 (1H, dd, J=5, 12Hz), 4.78–4.96 (1H, m), 6.42 (1H, dd, J=3, 9Hz), 6.59–6.66 (2H, m), 7.36 (2H, d, J=9Hz), 8.02 (2H, d, J=9Hz), 8.04–8.11 (1H, br s)

8) 5-(2-Chloro-4-nitrobenzoyl)-1,3,4,5-tetrahydro-1,5-benzodiazepin- 2(2H)-one

NMR (CDCl$_3$, δ): 2.60–3.04 (2H, m), 3.69–4.06 (1H, m), 4.87–5.22 (1H, m), 6.84–7.15 (3H, m), 7.15–7.47 (2H, m), 7.92 (1H, d, J=9Hz), 8.11 (1H, s), 8.49 (1H, s)

9) 5-(4-Nitrobenzoyl)-1,3,4,5-tetrahydro-1,5-benzodiazepine- 2(2H)-thione

NMR (CDCl$_3$, δ): 3.00–3.40 (2H, m), 3.85–4.10 (1H, m), 4.80–5.09 (1H, m), 6.76 (1H, br d, J=9Hz), 6.96–7.06 (1H, m), 7.19–7.46 (4H, m), 8.02 (2H, d, J=9Hz)

10) 4-Methyl-5-(4-nitrobenzoyl)-1,3,4,5-tetrahydro-1,5-benzodiazepin- 2(2H)-one

Rf: 0.53 (10% methanol in chloroform)

11) 5-(4-Nitorbenzoyl)-8-trifluoromethyl-1,3,4,5-tetrahydro- 1,5-benzodiazepin-2(2H)-one NMR (CDCl$_3$, δ): 2.76–2.85 (2H, br), 3.85–3.96 (1H, br), 4.80–4.95 (1H, br), 6.87 (1H, d, J=8Hz), 7.18 (1H, d, J=8 Hz), 7.40 (2H, d, J=10Hz), 7.41 (1H, s), 8.06 (2H, d, J=10Hz), 8.28–8.32 (1H, br s)

12) 7,8-Dimethyl-5-(4-nitrobenzoyl)-1,3,4,5-tetrahydro-1,5-benzodiazepin-2(2H )-one NMR (CDCl$_3$, δ): 1.96 (3H, s), 2.20 (3H, s), 2.57–2.93 (2H, m), 3.86 (1H, m), 4.87 (1H, m), 6.46 (1H, s), 6.92 (1H, s), 7.39 (2H, d, J=8.5Hz), 8.03 (2H, d, J=8.5Hz), 8.63 (1H, s)

13) 5-(3-Methyl-4-nitrobenzoyl)-1,3,4,5-tetrahydro-1,5-benzodiazepin- 2(2H)-one

NMR (CDCl$_3$, δ): 2.46 (3H, s), 2.60–3.00 (2H, m), 3.83 (1H, m), 4.84 (1H, m), 6.72 (1H, d, J=7.5Hz), 6.87–7.00 (2H, m), 7.17–7.31 (2H, m), 7.68 (1H, d, J=7.5Hz), 8.45 (1H, s)

PREPARATION 3

To a solution of 3-methoxy-4-nitrobenzoic acid (800 mg) and catalytic amount of N,N-dimethylformamide in dichloromethane (8 ml) was added oxalyl chloride (0.7 ml) at 0° C. and the solution was stirred at ambient temperature for 30 minutes followed by the removal of solvents to give a crude acid chloride. To a solution of 1,3,4,5-tetrahydro- 1,5-benzodiazepin-2(2H)-one (658 mg) and triethylamine (821 mg) in dichloromethane (4 ml) was added a solution of the above acid chloride in dichloromethane (4 ml) at ambient temperature and the mixture was stirred at ambient temperature for 1 hour. The resultant mixture was filtered and the solid was washed with water and diethyl ether to give 5-(3-methoxy-4-nitrobenzoyl)- 1,3,4,5-tetrahydro-1,5-benzodiazepin-2(2H)-one (1.29 g) as a colorless prisms.

mp: 195°–200° C.

PREPARATION 4

To a solution of 4-(4-nitrobenzoyl)-1,2,3,4-tetrahydroquinoxalin- 2-one (595 mg) in N,N-dimethylformamide (20 ml) was added sodium hydride (60% in oil, 80 mg). After being stirred at ambient temperature for 30 minutes, 3-bromopropylphthalimide (537 mg) was added to the solution and the mixture was stirred at ambient temperature for 4 hours. The mixture was diluted with ethyl acetate and the solution was washed successively with water, diluted hydrochloric acid, water and brine, dried over magnesium sulfate, and evaporated in vacuo to give an oil. The oil was purified by silica gel column (1% methanol in chloroform) to give 4-(4-nitrobenzoyl)-1-(3-phthaloylaminopropyl)-1,2,3,4-tetrahydroquinoxalin- 2-one (452 mg) as a pale yellow solid.

NMR (CDCl$_3$, δ): 2.16 (2H, tt, J=7.5, 7.5Hz), 3.79 (2H, t, J=7.5Hz), 4.18 (2H, t, J=7.5Hz), 4.58 (2H, s), 6.62 (1H, br), 6.81 (1H, t, J=7Hz), 7.08–7.24 (2H, m), 7.67 (2H, d, J=8.5Hz), 7.74 (2H, m), 7.86 (2H, m), 8.82 (2H, d, J=8.5Hz)

PREPARATION 5

The following compounds were obtained according to a similar manner to that of Preparation 4.

1) 1-Dimethylaminoethyl-5-(4-nitrobenzoyl)-1,3,4,5-tetrahydro- 1,5-benzodiazepin-2(2H)-one mp: 128°–131° C.

NMR (CDCl$_3$, δ): 2.26 (6H, s), 2.58–2.83 (4H, m), 3.80–4.00 (2H, m), 4.08–4.24 (1H, m), 4.78 (1H, ddd, J=5, 13, 13Hz), 6.65 (1H, d, J=8Hz), 6.91 (1H, dd, J=1, 8Hz), 7.25–7.35 (1H, m), 7.43 (1H, dd, J=1, 8Hz), 7.63 (2H, d, J=9Hz), 8.02 (1H, d, J=9Hz)

2) 1-Dimethylaminoethyl-5-(3-methoxy-4-nitrobenzoyl)-1,3,4,5-tetrahydro-1,5-benzodiazepin-2(2H)-one mp: 98°–102° C.

3) 1-(2-Ethoxycarbonylethyl)-5-(4-nitrobenzoyl)-1,3,4,5-tetrahydro- 1,5-benzodiazepin-2(2H)-one NMR (CDCl₃, δ): 1.26 (3H, t, J=7Hz), 2.52–3.10 (4H, m), 3.70–3.97 (1H, m), 4.02–4.40 (4H, m), 4.60–4.95 (1H, m), 6.58–6.82 (1H, m), 6.85–7.10 (1H, m), 7.20–7.72 (4H, m), 7.95–8.20 (2H, m)

4) 1-(3-Ethoxycarbonylpropyl)-5-(4-nitrobenzoyl)- 1,3,4,5-tetrahydro-1,5-benzodiazepin-2(2H)-one NMR (CDCl₃, δ): 1.27 (3H, t, J=7Hz), 1.96–2.31 (2H, m), 2.36–2.55 (2H, m), 2.56–2.85 (2H, m), 3.76–4.13 (3H, m), 4.62–4.92 (1H, m), 6.62–6.82 (1H, m), 6.85–7.09 (1H, m), 7.26–7.65 (4H, m), 8.06 (2H, br d, J=9Hz)

5) 1-(1-Ethoxycarbonylethyl)-5-(4-nitrobenzoyl)-1,3,4,5-tetrahydro- 1,5-benzodiazepin-2(2H)-one NMR (CDCl₃, δ): 1.17 (⅔×3H, t, J=7Hz), 1.33 (⅔×3H, t, J=7Hz), 1.67–1.92 (3H, m), 2.50–2.88 (2H, m), 3.75–3.96 (1H, m), 4.00–4.42 (2H, m), 4.43–4.70 (1H, m), 4.70–4.96 (1H, m), 6.69 (1H, br d, J=9Hz), 6.80–7.11 (1H, m), 7.20–7.66 (4H, m), 8.02 (2H, br d, J=9Hz)

6) 1-(t-Butoxycarbonylmethyl)-4-(4-nitrobenzoyl)- 1,2,3,4-tetrahydroquinoxalin-2-one NMR (CDCl₃, δ): 1.52 (9H, s), 4.68 (4H, s), 6.62 (1H, br), 6.81 (1H, t, J=8Hz), 6.93 (1H, dd, J=1, 8Hz), 7.18 (1H, dt, J= 1, 8Hz), 7.62 (2H, d, J=8.5Hz), 8.17 (1H, d, J=8.5Hz)

7) 5-(4-Nitrobenzoyl)-1-(4-phthaloylaminobutyl)-1,3,4,5-tetrahydro- 1,5-benzodiazepin-2(2H)-one NMR (CDCl₃, δ): 1.73–1.92 (4H, m), 2.57–2.71 (2H, m), 3.70–3.88 (4H, m), 4.09 (1H, m), 4.75 (1H, m), 6.63 (1H, d, J=8Hz), 6.90 (1H, t, J=8Hz), 7.23–7.40 (4H, m), 7.64–7.73 (2H, m), 7.78–7.86 (2H, m), 8.08 (2H, d, J=8.5Hz)

8) 1-(3-Dimethylaminopropyl)-4-(4-nitrobenzoyl)-1,2,3,4-tetrahydroquinoxalin- 2-one NMR (CDCl₃, δ): 1.82–2.02 (2H, m), 2.26 (6H, s), 2.39 (2H, t, J=7Hz), 4.08 (2H, t, J=7Hz), 4.58 (2H, s), 6.60 (1H, br), 6.80 (1H, br t, J=8Hz), 7.22 (1H, dd, J=1, 8Hz), 7.53 (2H, d, J=8.5Hz), 8.17 (2H, d, J=8.5Hz)

9) 1-(2-Dimethylaminoethyl)-4-(4-nitrobenzoyl)-1,2,3,4-tetrahydroquinoxalin- 2-one NMR (CDCl₃, δ): 2.30 (3H, s), 2.62 (2H, t, J=7Hz), 4.19 (1H, t, J=7Hz), 4.61 (2H, s), 6.58 (1H, br), 6.80 (1H, m), 7.19 (2H, d, J=4Hz), 7.57 (2H, d, J=8.5Hz), 8.15 (2H, d, J=8.5Hz)

10) 1-(3-Dimethylaminopropyl)-5-(4-nitrobenzoyl)-1,3,4,5-tetrahydro- 1,5-benzodiazepin-2(2H)-one NMR (CDCl₃, δ): 1.88–2.10 (3H, m), 2.27 (6H, s), 2.43 (2H, d, J=7Hz), 2.57–2.86 (2H, m), 3.78–3.90 (2H, m), 3.98 (2H, t, J=7Hz), 4.78 (1H, m), 6.67 (1H, d, J=8Hz), 6.93 (1H, t, J=8 Hz), 7.25–7.42 (4H, m), 8.03 (2H, d, J=8.5Hz)

11) 1-(4-Dimethylaminoethyl)-4-(3-methoxy-4-nitrobenzoyl)- 1,2,3,4-tetrahydroquinoxalin-2-one NMR (CDCl₃, δ): 2.30 (6H, s), 2.61 (2H, t, J=7Hz), 3.90 (3H, s), 4.18 (2H, t, J=7Hz), 4.57 (2H, s), 6.67 (1H, br), 6.80–6.94 (2H, m), 7.20–7.28 (3H, m), 7.68 (1H, d, J=8 Hz)

12) 4-(4-Nitrobenzoyl)-1-(3-piperidinopropyl)-1,2,3,4-tetrahydroquinoxalin- 2-one NMR (CDCl₃, δ): 1.46 (2H, m), 1.53–1.69 (4H, m), 1.78–2.02 (2H, m), 2.31–2.48 (6H, m), 4.09 (2H, t, J=7Hz), 4.56 (2H, s), 6.60 (1H, br) , 6.78 (1H, t, J=8Hz), 7.16–7.33 (2H, m), 7.52 (2H, d, J=8.5Hz), 8.17 (2H, d, J=8.5Hz)

13) 7,8-Dimethyl-1-ethoxycarbonylmethyl-5-(4-nitrobenzoyl)- 1,3,4,5-tetrahydro-1,5-benzodiazepin-(2H)-one Rf: 0.71 (10% methanol in chloroform)

14) 1-Ethoxycarbonylmethyl-7-methyl-5-(4-nitrobenzoyl)-1,3,4,5-tetrahydro-1,5 -benzodiazepin-2(2H)-one NMR (CDCl₃, δ): 1.31 (3H, t, J=8Hz), 2.07 (3H, s), 2.60–2.89 (2H, m) , 3.87 (1H, dd, J=5, 14Hz), 4.27 (2H, dq, J=1, 7Hz), 4.46 (1H, d, J=17Hz), 4.69–4.89 (1H, m) , 4.66 (1H, d, J=17Hz), 6.48–6.52 (1H, br s), 7.05–7.18 (2H, m), 7.51 (2H, d, J=9Hz), 8 .05 (2H, d, J=9Hz)

15) 8 -Chloro-1-ethoxycarbonylmethyl-5-(4-nitrobenzoyl)-1,3,4,5-tetrahydro-1,5-benzodiazepin-2 (2H)-one NMR (CDCl₃, δ): 1.34 (3H, t, J=8Hz), 2.67–2.89 (2H, m), 3.82–3.93 (1H, m), 4.29 (2H, q, J=7Hz), 4.50 (1H, d, J=16Hz), 4.65 (1H, d, J=16Hz), 4.67–4.88 (1H, m), 6.60–6.69 (1H, br d, J=8Hz), 6.90–6.98 (1H, br d, J=8 Hz), 7.20–7.30 (1H, m), 7.52 (2H, d, J=9Hz), 8.08 (2H, d, J=9Hz)

16) 8-Chloro-1-ethoxycarbonylmethyl-5-(3-methyl-4-nitrobenzoyl)- 1,3,4,5-tetrahydro-1,5-benzodiazepin-( 2H)-one Rf: 0.73 (10% methanol in chloroform)

17) 8-Chloro-1-ethoxycarbonylmethyl-5-(3-methoxy-4-nitrobenzoyl)- 1,3,4,5-tetrahydro-1,5-benzodiazepin(2H)-one Rf: 0.74 (10% methanol in chloroform)

18) 1-Ethoxycarbonylmethyl-5-(3-methoxy-4-nitrobenzoyl)- 8-methyl-1,3,4,5-tetrahydro-1,5-benzodiazepin-2(2H)one Rf: 0.79 (10% methanol in chloroform)

19) 1-Ethoxycarbonylmethyl-8-methyl-5-(4-nitrobenzoyl)-1,3,4,5-tetrahydro-1,5-benzodiazepin-2(2H)-one NMR (CDCl₃, δ): 1.32 (3H, t, J=7Hz), 2.31 (3H, s), 2.59–2.86 (2H, m), 3.86 (1H, dd, J=5, 13Hz), 4.22–4.36 (2H, m), 4.45 (1H, d, J=17Hz), 4.68 (1H, d, J=17Hz), 4.70–4.89 (1H, m), 6.58 (1H, d, J=8Hz), 6.72 (1H, d, J=8Hz), 7.03 (1H, s), 7.49 (2H, d, J=9Hz), 8.03 (2H, d, J=9Hz)

20) 1-Ethoxycarbonylmethyl-8-methyl-5-(3-methyl-4-nitrobenzoyl)- 1,3,4,5-tetrahydro-1,5-benzodiazepin-( 2(2H)-one Rf: 0.67 (10% methanol in chloroform)

21) 1-Ethoxycarbonylmethyl-8-methoxy-5-(4-nitrobenzoyl)- 1,3,4,5-tetrahydro-1,5-benzodiazepin-2(2H)-one Rf: 0.72 (10% methanol in chloroform)

22) 5-(2-Chloro-4-nitrobenzoyl)-1-ethoxycarbonylmethyl-1,3,4,5-tetrahydro-1,5-benzodiazepin-2(2H)-one NMR (CDCl₃, δ): 1.36 (3H, t, J=7Hz), 2.59–2.92 (2H, m), 3.77–4.00 (1H, m), 4.12–4.38 (1H, m), 4.30 (2H, q, J=7Hz), 4.74 (1H, d, J=16Hz), 4.98 (1H, dt, J=5, 14Hz), 6.90–7.08 (2H, m), 7.14–7.61 (3H, m), 7.92 (1H, d, J=9Hz), 8.12 (1H, s)

23) 5-(3-Benzyloxy-4-nitrobenzoyl)-1-ethoxycarbonylmethyl- 1,3,4,5-tetrahydro-1,5-benzodiazepin-2(2H)-one NMR (CDCl₃, δ): 1.28 (3H, t, J=7Hz), 2.57–2.86 (2H, m), 3.78–3.93 (1H, m), 4.22 (2H, q, J=7Hz), 4.38 (1H, d, J=11 Hz), 4.62 (1H, d, J=11Hz), 4.67–4.88 (1H, m), 5.01 (1H, d, J=9Hz), 5.10 (1H, d, J=9Hz), 6.66 (1H, br d, J=9Hz), 6.87 (1H, br d, J=9Hz), 6.92–7.04 (1H, m), 7.15–7.46 (5H, m), 7.60 (1H, br d, J=9Hz)

24) 4,4-Dimethyl-1-ethoxycarbonylmethyl-5-(4-nitrobenzoyl)- 1,3,4,5-tetrahydro-1,5-benzodiazepin(2H)-one Rf: 0.72 (10% methanol in chloroform)

25) 1-Ethoxycarbonylmethyl-4-methyl-5-(4-nitrobenzoyl)-1,3,4,5-tetrahydro-1,5-benzodiazepin-2(2H)-one Rf: 0.64 (10% methanol in chloroform)

26) 1-Ethoxycarbonylmethyl-5-(4-nitrobenzoyl)-8-trifluoromethyl- 1,3,4,5-tetrahydro-1,5-benzodiazepin-( 2(2H)-one NMR (CDCl₃, δ): 1.34 (3H, t, J=8 Hz), 2.70–2.79 (2H, m), 3.88–3.98 (1H, br), 4.29 (2H, dd, J=8, 15Hz), 4.62 (2H, s), 4.65–4.83 (1H, br), 7.19–7.27 (1H, br), 7.50–7.60 (3H, m), 8.00–8.12 (3H, m)

27) 5-(4-Nitrobenzoyl)-1-(3-pyridylmethyl)-1,3,4,5-tetrahydro- 1,5-benzodiazepin-2(2H)-one NMR (CDCl₃, δ): 2.68–2.81 (2H, m), 3.65–3.84 (1H, m), 4.69–4.87 (1H, m), 4.79 (1H, d, J=14Hz), 5.64 (1H, d, J=14Hz), 6.58 (1H, d, J=7.5Hz), 6.69 (1H, d, J=7.5Hz), 6.93 (1H, t, J=7.5Hz), 7.22–7.37 (3H, m), 7.48 (1H, dd, J=7.5, 1.5Hz), 7.77–7.89 (3H, m), 8.50–8.61 (2H, m)

28) 7,8-Dimethyl-1-ethoxycarbonylmethyl-5-(4-nitrobenzoyl)- 1,3,4,5-tetrahydro-1,5-benzodiazepin- 2(2H)-one NMR (CDCl$_3$, δ): 1.31 (3H, t, J=7.5Hz), 1.96 (3H, s), 2.19 (3H, s), 2.58–2.90 (2H, m), 3.84 (1H, m), 4.27 (2H, m), 4.42 (1H, d, J=15.5Hz), 4.67 (1H, d, J=15.5Hz), 4.80 (1H, m), 6.43 (1H, s), 7.00 (1H, s), 7.51 (2H, d, J=8.5Hz), 8.05 (2H, d, J=8.5Hz)

29) 1-(6-Chlorohexyl)-5-(4-nitrobenzoyl)-1,3,4,5-tetrahydro- 1,5-benzodiazepin-2(2H)-one NMR (CDCl$_3$, δ): 1.36–1.57 (4H, m), 1.70–1.87 (4H, m), 2.55–2.79 (2H, m), 3.53 (2H, t, J=7.5Hz), 3.78–4.00 (3H, m), 4.78 (1H, m), 6.67 (1H, d, J=7.5Hz), 6.91 (1H, m), 7.27–7.41 (4H, m), 8.04 (2H, d, J=8.5Hz)

30) 1-Ethoxycarbonylmethyl-5-(3-methyl-4-nitrobenzoyl)-1,3,4,5-tetrahydro-1,5-benzodiazepin-2(2H)-one NMR (CDCl$_3$, δ): 1.30 (3H, t, J=7.5Hz), 2.46 (3H, s), 2.60–2.89 (2H, m), 3.88 (1H, m), 4.25 (2H, m), 4.43 (1H, d, J=17Hz), 4.71 (1H, d, J=17Hz), 4.78 (1H, m), 6.70 (1H, d, J=7.5Hz), 6.97 (1H, m), 7.10–7.32 (3H, m), 7.41 (1H, s), 7.72 (1H, d, J=7.5Hz)

31) 1-Methoxycarbonylmethyl-5-(4-nitrobenzoyl)-1,3,4,5-tetrahydro- 1,5-benzodiazepin-2(2H)-one NMR (DMSO-d$_6$, δ): 2.45–2.80 (2H, m), 3.70 (3H, s), 3.78 (1H, m), 4.52 (1H, d, J=17.2Hz), 4.60 (1H, m), 4.78 (1H, d, J=17.2Hz), 6.90–7.06 (2H, m), 7.25–7.50 (2H, m), 7.47 (2H, d, J=8.7Hz), 8.04 (2H, d, J=8.7Hz)

PREPARATION 6

To a suspension of sodium hydride (60% oil suspension, 154 mg) in tetrahydrofuran (4 ml) was added a solution of 5-(4-nitrobenzoyl)-1,3,4,5-tetrahydro-1,5-benzodiazepin-2(2H)-one (800 mg) in tetrahydrofuran (6 ml) at 0° C. and the mixture was stirred at 0° C. for 5 minutes. To the mixture was added ethyl bromoacetate (472 mg) and then the mixture was stirred at ambient temperature overnight. The reaction was quenched with saturated ammonium chloride aqueous solution and the resultant mixture was diluted with ethyl acetate. The organic layer was washed with saturated sodium bicarbonate aqueous solution and brine, and then it was dried over magnesium sulfate. Filtration and evaporation afforded 1-ethoxycarbonylmethyl-5-(4-nitrobenzoyl)-1, 3,4,5-tetrahydro- 1,5-benzodiazepin-2(2H)-one (691 mg) as a slightly yellow amorphous.

NMR (CDCl$_3$, δ): 1.33 (3H, t, J=7Hz), 2.62–2.90 (2H, m), 3.90 (1H, ddd, J=1, 7, 13Hz), 4.29 (2H, ddd, J=1, 7, 15Hz), 4.50 (1H, d, J=16Hz), 4.70 (1H, d, J=16Hz), 4.65–4.90 (1H, m), 6.72 (1H, d, J=9Hz), 6.90–7.02 (1H, br), 7.23–7.37 (2H, m), 7.50 (2H, d, J=9Hz), 8.03 (2H, d, J=9Hz)

PREPARATION 7

The mixture of 1-ethoxycarbonylmethyl-5-(4-nitrobenzoyl)- 1,3,4,5-tetrahydro-1,5-benzodiazepin-2(2H)-one (667 mg), iron powder (469 mg), methanol (10 ml) and acetic acid (1 ml) was refluxed for 1 hour. The reaction mixture was cooled to ambient temperature and it was filtered through a bed of celite followed by the removal of methanol. The residue was diluted with chloroform and to the mixture was added saturated sodium bicarbonate aqueous solution followed by stirring for 10 minutes. The resulting mixture was filtered through a bed of celite and the organic layer was washed with brine. Drying the filtrate, and the removal of chloroform obtained a crude product. The crude product was triturated with a mixture of diisopropyl ether and n-hexane (1:1) to give 5-(4-aminobenzoyl)- 1-ethoxycarbonylmethyl- 1,3,4,5-tetrahydro- 1,5-benzodiazepin-2(2H)-one (610 mg) as a slightly brown powder.

mp: 80°–83° C.

NMR (CDCl$_3$, δ): 1.31 (3H, t, J=7Hz), 2.56–2.88 (2H, m), 3.78–3.90 (3H, br s), 4.15–4.35 (3H, m), 4.60–4.80 (1H, m), 4.83 (1H, d, J=16Hz), 6.39 (2H, d, J=9Hz), 6.80 (1H, d, J=9Hz), 6.95–7.05 (2H, m ), 7.03 (1H, d, J=9Hz), 7.26 (2H, s)

PREPARATION 8

The following compounds were obtained according to a similar manner to that of Preparation 7.

1) 5-(4-Aminobenzoyl)-1-dimethylaminoethyl-1,3,4,5-tetrahydro- 1,5-benzodiazepin-2(2H)-one NMR (CDCl$_3$, δ): 2.39 (6H, s), 2.50–2.75 (4H, m), 3.77–3.90 (3H, br), 3.92–4.15 (2H, m), 4.56–4.78 (1H, m), 6.40 (1H, d, J=9Hz), 6.79 (1H, d, J=9Hz), 6.99 (1H, dt, J=1, 8Hz), 7.12–7.26 (1H, m), 7.15 (1H, d, J=9Hz), 7.29 (1H, dd, J=1, 8Hz), 7.42 (1H, dd, J=1, 8Hz)

2) 5-(4-Aminobenzoyl)-1,3,4,5-tetrahydro-1,5-benzodiazepin- 2(2H)-one mp: 216°–221° C.

3) 5-(4-Amino-3-methoxy)-1-dimethylaminoethyl-1,3,4,5-benzodiazepin- 2(2H)-one

Slightly yellow oil 4) 5-(4-Amino-3-methoxybenzoyl)-1,3,4,5-tetrahydro-1,5-benzodiazepin- 2(2H)-one Slightly yellow oil 5) 5-(4-Aminobenzoyl)-1,3,4,5-tetrahydro-1,5-benzodiazepin- 2(2H)-one NMR (CDCl$_3$, δ): 2.67 (2H, br), 3.90–4.80 (2H, br), 6.38 (2H, d, J=8.5Hz), 6.78 (1H, dd, J=1, 8Hz), 6.90–7.24 (5H, m)

6) 5-(4-Aminobenzoyl)-1-(2-ethoxycarbonylethyl)-1,3,4,5-tetrahydro- 1,5-benzodiazepin-2(2H)-one NMR (CDCl$_3$, δ): 1.26 (3H, t, J=7Hz), 2.45–2.77 (2H, m), 2.78–3.00 (2H, m), 3.71–4.05 (2H, m), 4.05–4.37 (5H, m), 4.50–4.80 (1H, m), 6.43 (1H, d, J=9Hz), 6.82 (1H, br d, J=9Hz), 6.94–7.20 (3H, m), 7.20–7.46 (3H, m)

7) 5-(4-Aminobenzoyl)-1-(3-ethoxycarbonylpropyl)- 1,3,4, 5-tetrahydro-1,5-benzodiazepin-2(2H)-one NMR (CDCl$_3$, δ): 1.23 (3H, t, J=7Hz), 1.63–2.81 (6H, m), 3.68–4.25 (5H, m), 4.52–4.78 (1H, m), 6.41 (2H, d, J=9Hz), 6.80 (1H, d, J=9Hz), 6.90–7.15 (3H, m), 7.21–7.46 (2H, m)

8) 5-(4-Aminobenzoyl)-1-(1-ethoxycarbonylethyl)-1,3,4,5-tetrahydro- 1,5-benzodiazepin-2(2H)-one NMR (CDCl$_3$, δ): 1.13 (⅝×3H, t, J=7Hz), 1.31 (⅔×3H, t, J=7Hz), 1.72 (3H, d, J=7Hz), 2.41–2.83 (2H, m), 3.70–4.85 (7H, m), 6.32–6.53 (2H, m), 6.70–6.91 (1H, m), 6.92–7.53 (5H, m)

9) 4-(4-Aminobenzoyl)-1-(t-butoxycarbonylmethyl)- 1,2,3, 4-tetrahydroquinoxalin-2-one NMR (CDCl$_3$, δ): 1.46 (9H, s), 3.97 (2H, s), 4.58 (2H, s), 4.62 (2H, s), 6.52 (2H, d, J=8.5Hz), 6.77–6.88 (3H, m), 7.09 (1H, m), 7.27 (2H, d, J=8.5Hz)

10) 5-(4-Aminobenzoyl)-1-(3-dimethylaminopropyl)-1,3,4, 5-tetrahydro- 1,5-benzodiazepin-2(2H)-one NMR (CDCl$_3$, δ): 1.87–2.03 (3H, m), 2.23 (6H, s), 2.35–2.46 (2H, m), 2.51–2.64 (2H, m), 3.35–3.89 (3H, m), 4.03 (1H, m), 4.65 (1H, m), 6.40 (2H, d, J=8.5Hz), 6.79 (1H, d, J=8Hz), 6.98 (1H, ddd, J=8, 8, 1Hz), 7.07 (2H, d, J=8.5Hz), 7.20–7.35 (2H, m)

11) 5-(4-Aminobenzoyl)-1-(4-phthaloylaminobutyl)-1,3,4, 5-tetrahydro- 1,5-benzodiazepin-2(2H)-one NMR (CDCl$_3$, δ): 1.70–1.89 (4H, m), 2.48–2.72 (2H, m), 3.68–3.89 (4H, m), 3.80 (2H, s), 4.08 (1H, m), 4.64 (1H, m), 6.40 (2H, d, J=8.5Hz), 6.79 (1H, d, J=8Hz), 6.98 (1H, ddd, J=8, 8, 1Hz), 7.07 (2H, d, J=8.5Hz), 7.19–7.35 (2H, m), 7.65–7.76 (2H, m), 7.79–7.86 (2H, m)

12) 4-(4-Aminobenzoyl)-1-(3-phthaloylaminopropyl)- 1,2,3,4-tetrahydroquinoxalin-2-one 13) 4-(4-Aminobenzoyl)-1-(3-dimethylaminopropyl)-1,2,3,4-tetrahydroquinoxalin- 2-one
NMR (CDCl$_3$, δ): 1.82–1.98 (2H, m), 2.23 (6H, s), 2.38 (2H, t, J=7Hz), 3.96 (2H, s), 4.06 (2H, t, J=7Hz), 4.51 (2H, s), 6.52 (2H, d, J=8.5Hz), 6.78–6.84 (2H, m), 7.06–7.15 (2H, m), 7.72 (2H, d, J=8.5Hz)

14) 4-(4-Aminobenzoyl)-1-(2-dimethylaminoethyl)-1,2,3,4-tetrahydroquinoxalin- 2 -one
NMR (CDCl$_3$, δ): 2.32 (6H, s), 2.61 (2H, t, J=7Hz), 3.94 (2H, s), 4.15 (2H, t, J=7Hz), 4.53 (2H, s), 6.52 (2H, d, J=8.5Hz), 6.74–6.87 (2H, m), 7.09–7.18 (2H, m ), 7.25 (2H, d, J=8.5Hz)

15) 1-(2-Dimethylaminoethyl)-4-(4-amino-3methoxybenzoyl)- 1,2,3,4-tetrahydroquinoxalin-2-one
NMR (CDCl$_3$, δ): 2.31 (6H, s), 2.60 (2H, t, J=7Hz), 3.74 (2H, s), 4.10 (2H, s), 4.14 (2H, t, J=7Hz), 4.54 (2H, s), 6.49 (1H, d, J=8Hz), 6.78–6.85 (3H, m), 6.97 (1H, d, J=1Hz), 7.08–7.19 (2H, m)

16) 4-(4-Aminobenzoyl)-1-(3-piperidinopropyl)-1,2,3,4-tetrahydroquinoxalin- 2-one
NMR (CDCl$_3$, δ): 1.39–1.50 (2H, m), 1.53–1.66 (4H, m), 1.85–2.00 (2H, m), 2.33–2.49 (6H, m), 3.96 (2H, s), 4.06 (2H, t, J=7Hz), 4.50 (2H, s), 6.52 (2H, d, J=S.5Hz), 6.75–6.86 (2H, m), 7.06–7.28 (4H, m)

17) 5-(4-Aminobenzoyl)-7,8-dimethyl-1-ethoxycarbonylmethyl- 1,3,4,5-tetrahydro-1,5-benzodiazepin-2(2H)-one
Rf: 0.60 (10% methanol in chloroform)

18) 5-(4-Aminobenzoyl)-1-ethoxycarbonylmethyl-7-methyl- 1,3,4,5-tetrahydro-1,5-benzodiazepin-2(2H)-one
NMR (CDCl$_3$, δ): 1.29 (3H, t, J=8Hz), 2.13 (3H, s), 2.52–2.83 (2H, m), 3.73–3.88 (2H, br s), 4.10–4.36 (3H, m), 4.50–4.82 (2H, m), 4.80 (1H, d, J=15Hz), 6.30–6.45 (2H, m), 6.59 (1H, s), 7.00–7.16 (4H, m)

19) 5-(4-Aminobenzoyl)-8-chloro-1-ethoxycarbonylmethyl- 1,3,4,5-tetrahydro-1,5-benzodiazepin-2(2H)-one
NMR (CDCl$_3$, δ): 1.32 (3H, t, J=8Hz), 2.62–2.79 (2H, m), 3.72–3.91 (3H, m), 4.15–4.35 (3H, m), 4.54–4.90 (2H, m), 6.43 (2H, d, J=10Hz), 6.73 (1H, d, J=9Hz), 6.98 (1H, dd, J=2, 9Hz), 7.05 (2H, d, J=10Hz), 7.27 (1H, d, J=2Hz)

20) 5-(4-Amino-3-methylbenzoyl)-8-chloro-1-ethoxycarbonylmethyl- 1,3,4,5-tetrahydro-1,5-benzodiazepin- 2(2H)-one
Rf: 0.56 (10% methanol in chloroform)

21) 5-(4-Amino-3-methoxybenzoyl)-8-chloro-1-ethoxycarbonylmethyl- 1,3,4,5-tetrahydro-1,5-benzodiazepin-2(2H)-one
Rf: 0.58 (10% methanol in chloroform)

22) 5-(4-Amino-3-methoxybenzoyl)-1-ethoxycarbonylmethyl- 8-methyl-1,3,4,5-tetrahydro-1,5-benzodiazepin-2(2H)-one
Rf: 0.65 (10% methanol in chloroform)

23) 5-(4-Aminobenzoyl)-1-ethoxycarbonylmethyl-8-methyl- 1,3,4,5-tetrahydro-1,5-benzodiazepin-2(2H)-one
NMR (CDCl$_3$, δ) : 1.30 (3H, t, J=8Hz), 2.32 (3H, s), 2.52–2.85 (2H, m), 3.73–3.88 (2H, br), 4.12–4.43 (4H, m), 4.55–4.90 (2H, m), 6.33–6.45 (2H, m), 6.67 (1H, d, J=8Hz), 6.80 (1H, d, J=8Hz), 7.04–7.13 (3H, m)

24) 5-(4-Amino-3-methylbenzoyl)-1-ethoxycarbonylmethyl-8-methyl- 1,3,4,5-tetrahydro-1,5-benzodiazepin-2(2H)-one
Rf: 0.55 (10% methanol in chloroform)

25) 5-(4-Aminobenzoyl)-1-ethoxycarbonylmethyl-8-methoxy- 1,3,4,5-tetrahydro-1,5-benzodiazepin-2(2H)-one
Rf: 0.52 (10% methanol in chloroform)

26) 5-(4-Amino-2-chlorobenzoyl)-1-ethoxycarbonylmethyl- 1,3,4,5-tetrahydro-1,5-benzodiazepin-2(2H)-one
NMR (CDCl$_3$, δ): 1.32 (3H, t, J=7Hz), 2.49–2.91 (2H, m), 3.70–4.07 (4H, m), 4.20–4.40 (2H, m), 4.74–4.99 (2H, m), 6.28 (1H, d, J=9Hz), 6.46 (1H, br s), 6.72–7.46 (5H, m)

27) 5-(4-Amino-3-methoxybenzoyl)-1-ethoxycarbonylmethyl- 1,3,4,5-tetrahydro-1,5-benzodiazepin-2(2H)-one
NMR (CDCl$_3$, δ): 1.29 (3H, t, J=7Hz), 2.52–2.91 (2H, m), 3.66 (3H, s), 3.77–3.94 (1H, m), 4.00 (2H, br s), 4.13–4.38 (3H, m), 4.59–4.80 (1H, m), 4.82 (1H, d, J=16Hz), 6.37 (1H, d, J=9Hz), 6.63 (1H, d, J=9Hz), 6.78–6.87 (2H, m), 6.96–7.09 (1H, m), 7.22–7.32 (2H, m)

28) 1-(4-Aminobenzoyl)-3-methyl-1,2,3,5-tetrahydro-1,3-benzodiazepin- 4(4H)-one
NMR (CDCl$_3$, δ): 3.06 (3H, s), 3.96 (2H, br s), 4.09 (2H, s), 5.37 (2H, s), 6.44 (2H, d, J=9Hz), 6.71 (1H, d, J=9Hz), 6.91–7.26 (5H, m)

29) 5-(4-Aminobenzoyl)-1,3,4,5-tetrahydro-1,5-benzodiazepine- 2(2H)-thione
NMR (DMSO-d$_6$, δ): 2.91 (2H, m), 3.81–4.45 (2H, m), 5.53 (2H, s), 6.26 (2H, d, J=9Hz), 6.78 (3H, m), 7.05 (1H, dd, J=9, 9Hz), 7.20 (1H, d, J=9Hz), 7.28 (1H, dd, J=9, 9Hz)

30) 1-(4-Aminobenzoyl)-5-ethoxycarbonylmethoxyimino- 2,3,4,5-tetrahydro-1H-1-benzazepine
NMR (CDCl$_3$, δ): 1.26 (3H, t, J=7Hz), 1.60–2.13 (2H, m), 2.77–3.00 (2H, m), 3.68–3.96 (1H, br s), 4.21 (2H, q, J=7Hz), 4.11–4.33 (1H, m), 4.79 (2H, s), 6.37 (2H, d, J=8 Hz), 6.71 (1H, d, J=8HZ), 7.05 (2H, d, J=8Hz), 7.10–7.28 (2H, m), 7.49 (1H, d, J=8 Hz)

31) 5-(4-Aminobenzoyl)-8-methoxy-11-oxo-6,11-dihydrodibenz[ b,e]azepine
NMR (CDCl$_3$, δ): 3.70–3.93 (2H, br s), 3.91 (3H, s), 5.00–5.45 (2H, br), 6.38 (2H, d, J=8Hz), 6.72–7.35 (7H, m), 8.20–8.42 (2H, m)

32) 1-(4-Aminobenzoyl)-5-methyl-2,3,4,5tetrahydropyrido[ 3,2-b][1,4]diazepine
NMR (CDCl$_3$, δ): 1.96–2.18 (2H, br s), 3.15 (3H, s), 2.97–3.52 (2H, m), 3.78 (3H, br s), 4.43–4.80 (1H, m), 6.30–6.48 (3H, m), 6.77 (1H, br d, J=9Hz), 7.12 (2H, d, J=9Hz), 7.96–8.03 (1H, m)

33) 5-(4-Aminobenzoyl)-4,4-dimethyl-1-ethoxycarbonylmethyl- 1,3,4,5-tetrahydro-1,5-benzodiazepin-2(2H)-one
NMR (CDCl$_3$, δ): 1.31 (3H, t, J=8Hz), 1.57 (3H, s), 1.90 (3H, s), 2.27 (1H, d, J=13Hz), 2.53 (1H, d, J=13Hz), 3.70–3.79 (2H, br s), 4.19–4.35 (3H, m), 4.89 (1H, d, J=18 Hz), 6.35 (2H, d, J=9Hz), 6.78 (2H, d, J=10Hz), 7.02–7.20 (4H, m)

34) 5-(4-Aminobenzoyl)-4-methyl-1-ethoxycarbonylmethyl- 1,3,4,5-tetrahydro-1,5-benzodiazepin-2(2H)-one
Rf: 0.58 (10% methanol in chloroform)

35) 5-(4-Aminobenzoyl)-1-(3,4-dimethoxybenzenesulfonyl)- 2,3,4,5-tetrahydro-1H-1,5-benzodiazepine
Rf: 0.58 (10% methanol in chloroform)

36) 5-(4-Aminobenzoyl)-1-ethoxycarbonylmethyl-8-trifluoromethyl- 1,3,4,5-tetrahydro-1,5-benzodiazepin-( 2(2H)-one
NMR (CDCl$_3$, d): 1.32 (3H, t, J=8Hz), 2.65–2.75 (2H, br), 3.86–3.90 (2H, s), 4.22–4.34 (4H, m), 6.41 (2H, d, J=8 Hz), 6.93 (1H, d, J=9Hz), 7.06 (2H, d, J=8 Hz), 7.26 (1H, d, J=9Hz), 7.53 (1H, s)

37) 5-(4-Aminobenzoyl)-1-(3-pyridylmethyl)-1,3,4,5-tetrahydro- 1,5-benzodiazepin-2(2H)-one
NMR (CDCl$_3$, δ): 2.61–2.80 (2H, m), 3.74–3.90 (3H, m), 4.67 (1H, m), 4.79 (1H, d, J=15Hz), 5.60 (1H, d, J=15Hz), 6.19 (2H, d, J=8.5Hz), 6.44 (1H, d, J=8.5Hz), 6.69 (1H, dd, J=7.5, 1.5Hz), 6.97 (1H, dt, J=l.5, 7.5Hz), 7.14–7.31 (2H, m), 7.41 (1H, dd, J=7.5, 1.5Hz), 7.86 (1H, m), 8.43–8.53 (2H, m)

38) 5-(4-Aminobenzoyl)-7,8-dimethyl-1-ethoxycarbonylmethyl- 1,3,4,5-tetrahydro-1,5-benzodiazepine-2(2H)-one NMR (CDCl$_3$, δ): 1.28 (3H, t, J=7.5Hz), 2.01 (3H, s), 2.20 (3H, s), 2.50–2.83 (2H, m), 3.26 (1H, m), 3.32 (2H, br), 4.57 (1H, m), 4.80 (1H, d, J=15.5Hz), 6.39 (2H, d, J=8.5Hz), 6.53 (1H, s), 6.99 (1H, s), 7.08 (2H, d, J=8.5Hz)

39) 5-(4-Aminobenzoyl)-1-ethoxycarbonylmethyl-2,3,4,5-tetrahydro- 1H-1,5-benzodiazepine NMR (CDCl$_3$, δ): 1.31 (3H, t, J=7.5Hz), 2.01 (2H, m), 3.20 (2H, m), 3.60–3.80 (3H, m), 4.06 (2H, m), 4.25 (2H, q, J=7.5Hz), 4.67 (1H, m), 6.38 (2H, d, J=8.5Hz), 6.53–6.62 (2H, m), 6.71 (1H, d, J=7.5Hz), 7.00 (1H, m), 7.15 (2H, d, J=8.5Hz)

40) 5-(4-Aminobenzoyl)-1-(6-phthalimidohexyl)-1,3,4,5-tetrahydro- 1,5-benzodiazepin-2(2H)-one This product was used for next step without purification.

41) 1-Ethoxycarbonylmethyl-5-(4-amino-3-methylbenzoyl)- 1,3,4,5-tetrahydro-1,5-benzodiazepin-2(2H)-one NMR (CDCl$_3$, δ): 1.30 (3H, t, J=7.5Hz), 2.02 (3H, s), 2.53–2.87 (2H, m), 3.69–3.90 (3H, m), 4.12–4.33 (3H, m), 4.69 (1H, m), 4.88 (1H, d, J=17Hz), 6.43 (1H, d, J=7.5Hz), 6.80 (1H, d, J=7.5Hz), 6.99 (1H, m), 7.08 (1H, m), 7.16–7.27 (3H, m)

42) 1-(4-Aminobenzoyl)-7-chloro-5-ethoxycarbonylmethyl- 2,3,4,5-tetrahydro-1H-1-benzazepine NMR (CDCl$_3$, δ): 1.26 (3H, t, J=7.5Hz), 1.31–2.14 (4H, m), 2.59–3.01 (2H, m), 3.12 (1H, m), 3.78 (2H, br), 4.03–4.27 (3H, m), 4.52 (1H, m), 6.38 (2H, d, J=8.5Hz), 6.68 (1H, d, J=7.5Hz), 6.95 (1H, m), 7.03–7.20 (3H, m)

43) 1-(4-Aminobenzoyl)-5-ethoxycarbonylmethyl-2,3-dihydro- 1H-1-benzazepine

NMR (CDCl$_3$, δ): 1.23 (3H, t, J=7.5Hz), 2.37 (1H, m), 2.58 (1H, m), 3.34–3.50 (2H, m), 3.68–3.82 (3H, m), 4.11 (2H, m), 4.77 (1H, m), 6.24 (1H, d, J=5Hz), 6.38 (2H, d, J=8.5Hz), 6.72 (1H, dd, J=1.5, 7.5Hz), 6.97 (1H, dt, J=1.5, 7.5Hz), 7.10 (2H, d, J=8.5Hz), 7.16 (1H, dt, J=1.5, 7.5Hz), 7.38 (1H, dd, J=1.5, 7.5Hz)

44) 5-(4-Aminobenzoyl)-2-(4-methyl-1-piperazinyl)-3,4-dihydro- 5H-1,5-benzodiazepine NMR (CDCl$_3$, δ): 2.33 (3H, s), 2.68 (2H, m), 3.58–3.91 (5H, m), 4.62 (2H, m), 6.38 (2H, d, J=8.5Hz), 6.61–6.72 (2H, m), 7.01 (1H, d, J=7.5Hz), 7.05–7.17 (3H, m)

45) 1-(4-Aminobenzoyl)-2,3-dimethylindoline

NMR (CDCl$_3$, δ): 1.10 (3H, d, J=6.5Hz), 1.27 (3H, d, J=6.5Hz), 3.55 (1H, dq, J=6.5, 6.5Hz), 3.94 (2H, br), 4.74 (1H, dq, J=6.5, 6.5Hz), 6.66 (2H, d, J=8.5Hz), 6.93–7.03 (3H, m), 7.14 (1H, m), 7.47 (2H, d, J=8.5Hz)

46) 5-(4-Aminobenzoyl)-1-methoxycarbonylmethyl-1,3,4, 5-tetrahydro- 1,5-benzodiazepin-2(2H)-one NMR (DMSO-d$_6$, δ): 2.35–2.70 (2H, m), 3.60 (3H, s), 3.60 (1H, m), 4.40 (1H, m), 4.47 (1H, d, J=16.6Hz), 4.75 (1H, d, J=16.6Hz), 5.50 (2H, s), 6.27 (2H, d, J=8.6Hz), 6.82 (1H, m), 6.88 (2H, d, J=8.6Hz), 7.04 (1H, m), 7.25–7.38 (2H, m)

PREPARATION 9

A mixture of N-ethoxycarbonylmethyl-N-( 4-nitrobenzoyl)-2-nitroaniline (500 mg) and iron powder (374 mg) in a mixture of ethanol (10 ml) and acetic acid (1 ml) was heated at 80° C. for 3 hours and the solution was cooled to ambient temperature. The mixture was filtered through celite and the filtrate was evaporated in vacuo. The residue was dissolved in chloroform (20 ml) and the solution was neutralized with aqueous sodium hydrogen carbonate. The solution was filtered through celite and the organic filtrate was washed with brine. The solution was dried over magnesium sulfate and the solvent was evaporated in vacuo to give a crude oil. The oil was purified by silica gel column (10 g, 2% methanol in chloroform) to give 4-(4-aminobenzoyl)-1,2,3,4-tetrahydroquinoxalin- 2-one (58 mg) as a pale yellow powder.

NMR (DMSO-d$_6$, δ): 4.31 (2H, s), 5.71 (2H, br), 6.43 (2H, d, J=8.5Hz), 6.69–6.83 (2H, m), 6.98–7.09 (4H, m)

PREPARATION 10

A mixture of N-(2-ethoxycarbonylethyl)-4-methyl-2-nitroaniline (11.25 g) and iron powder (12.45 g) in a mixture of methanol (70 ml) and acetic acid (7 ml) was refluxed for 1 hour and the solution was cooled to ambient temperature. The mixture was filtered through celite and the filtrate was evaporated in vacuo. The residue was dissolved with chloroform (50 ml) and the solution was basified with saturated sodium bicarbonate aqueous solution. The solution was filtered through celite and the organic layer was washed with brine. The solution was dried over magnesium sulfate and the solvent was removed. A mixture of the residue (8.00 g) in a mixture of concentrated hydrochloric acid (16 ml) and water (12 ml) was refluxed for 1 hour and the solution was cooled to ambient temperature. The mixture was basified with concentrated ammonium hydroxide and then the resulting solution was extracted with chloroform. Drying over magnesium sulfate, filtering and the removal of solvents afforded a crude product. The crude product was triturated with diethyl ether - isopropyl ether (1:1) to give 8-methyl-1,3,4,5-tetrahydro-1,5-benzodiazepin- 2(2H)-one (1.26 g) as a brown powder.

NMR (CDCl$_3$, δ): 2.26 (3H, s), 2.70 (2H, t, J=7Hz), 3.58–3.70 (1H, br), 3.66 (2H, t, J=7Hz), 6.63–6.69 (2H, m), 6.80 (1H, dd, J=1, 8Hz), 7.52–7.60 (1H, br)

PREPARATION 11

The following compounds were obtained according to a similar manner to that of Preparation 10.

1) 7-Methyl-1,3,4,5-tetrahydro-1,5-benzodiazepin-2(2H)-one

NMR (CDCl$_3$, δ): 2.27 (3H, s), 2.72 (2H, t, J=6Hz), 3.67 (2H, t, J=6Hz), 3.69–3.82 (1H, br), 6.56 (1H, s), 6.62 (1H, dd, J=1, 8Hz), 6.74 (1H, d, J=8 Hz), 7.58–7.67 (1H, br)

2) 8-Chloro-1,3,4,5-tetrahydro-1,5-benzodiazepin-2(2H)-one (CDCl$_3$, δ): 2.71 (2H, t, J=6Hz), 3.67 (2H, t, J=6Hz), 3.70–3.95 (1H, br), 6.68 (1H, d, J=9Hz), 6.88 (1H, d, J=9Hz), 6.95 (1H, s), 7.82–7.94 (1H, br)

3) 8-Methoxy-1,3,4,5-tetrahydro-1,5-benzodiazepin-2 (2H)-one

Rf: 0.29 (ethyl acetate)

4) 8-Trifluoromethyl-1,3,4,5-tetrahydro-1,5-benzodiazepin-2(2H)-one

NMR (CDCl$_3$, δ): 2.79 (2H, t, J=5Hz), 3.69 (2H, dd, J=5, 10Hz), 4.21–4.29 (1H, br), 6.73 (1H, d, J=8 Hz), 7.05 (1H, s), 7.18 (1H, d, J=8 Hz), 7.58–7.64 (1H, br s)

PREPARATION 12

To a solution of 4,4-dimethyl-1,3,4,5-tetrahydro-1,5-benzodiazepin- 2(2H)-one (1.0 g) in N,N-dimethylaniline (20 ml) was added 4-nitrobenzoyl chloride (0.98 g) at ambient temperature. The mixture was stirred at 150° C. for 9 hours. The resulting mixture was diluted with chloroform and the organic layer was washed successively with 1N hydrochloric acid and saturated aqueous sodium bicarbonate. Drying, filtering and the removal of solvents afforded a crude product. The crude product was chromatographed on silica gel (1% methanol in chloroform) to give 4,4-dimethyl-5-(4- nitrobenzoyl)-1,3,4,5-tetrahydro- 1,5-benzodiazepin-2(2H)-one (195 mg) as a slightly yellow solid.

NMR (CDCl$_3$, δ): 1.65 (3H, s), 2.02 (3H, s), 2.29 (1H, dd, J=1, 19Hz), 2.70 (1H, d, J=19Hz), 6.70–6.90 (2H, m), 7.03–7.20 (2H, m), 7.35 (2H, d, J=9Hz), 7.96 (2H, d, J=9Hz)

PREPARATION 13

To a solution of 1,3,4,5-tetrahydro-1,5-benzodiazepin-2(2H)-one (700 mg) in pyridine (10 ml) was added 3,4-dimethoxybenzenesulfonyl chloride (1.07 g) and the mixture was stirred at ambient temperature for 2 hours. The resulting mixture was diluted with ethyl acetate, and then the organic solution was washed successively with 0.5N hydrochloric acid, saturated aqueous sodium bicarbonate solution and brine. Drying, filtering and the removal of solvents afforded a crude product. The crude product was triturated with a mixture of diethyl ether and n-hexane (1:1) to give 5-(3,4-dimethoxybenzenesulfonyl)- 1,3,4,5-tetrahydro-1,5-benzodiazepin- 2(2H)-one (1.33 g) as a yellow powder.

NMR (CDCl$_3$, δ): 2.51 (2H, t, J=8Hz), 3.77 (3H, s), 3.87 (3H, s), 4.32 (2H, t, J=8Hz), 6.80 (1H, d, J=8 Hz), 6.88 (2H, dd, J=3, 10Hz), 7.20 (2H, dd, J=2, 10Hz), 7.25–7.39 (2H, m), 7.67 (1H, dd, J=1, 8Hz)

PREPARATION 14

To a mixture of 2,3-dimethylindoline (736 mg) and triethylamine (0.836 ml) in dichloromethane (20 ml) was added p-nitrobenzoyl chloride (928 mg) and the solution was stirred at ambient temperature for 4 hours. The solution was washed successively with 1N hydrochloric acid, saturated aqueous sodium hydrogen carbonate, water and brine, and dried over magnesium sulfate. The solvent was evaporated in vacuo and the residue was solidified with n-hexane to give 2,3-dimethyl-1-(4-nitrobenzoyl)indoline (83.2 g).

NMR (CDCl$_3$, δ): 1.18 (3H, d, J=6.5Hz), 1.31 (3H, d, J=6.5Hz), 3.59 (1H, dq, J=6.5, 6.5Hz), 4.77 (1H, dq, J=6.5, 6.5Hz), 7.15–7.45 (6H, m), 7.63 (1H, d, J=8.5Hz)

PREPARATION 15

The following compounds were obtained according to a similar manner to that of Preparation 14.

1) 3-Methyl-1-(4-nitrobenzoyl)-1,2,3,5-tetrahydro-1,3-benzodiazepin- 4(4H)-one

NMR (CDCl$_3$, δ): 3.15 (3H, s), 4.13 (2H, s), 5.43 (2H, s), 6.54 (1H, d, J=9Hz), 6.94 (1H, t, J=9Hz), 7.14 (1H, t, J=9Hz), 7.25 (1H, d, J=9Hz), 7.42 (2H, d, J=9Hz), 8.10 (2H, d, J=9Hz)

2) 1-(3,4-Dimethoxybenzenesulfonyl)-5-(4-nitrobenzoyl)-2,3,4,5-tetrahydro-1H-1,5-benzodiazepin Rf: 0.67 (10% methanol in chloroform)

3) 1-Ethoxycarbonylmethyl-5-(4-nitrobenzoyl)-2,3,4,5-tetrahydro- 1H-1,5-benzodiazepine NMR (CDCl$_3$, δ) : 1.36 (3H, t, J=7.5Hz), 1.98 (1H, m), 2.16 (1H, m), 3.04–3.23 (2H, m), 3.61 (1H, m), 3.98 (1H, d, J=17Hz), 4.19 (1H, d, J=17Hz), 4.28 (2H, q, J=7.5Hz), 4.70 (1H, m), 6.59 (2H, d, J=5Hz), 6.77(1H, d, J=7.5Hz), 7.08 (1H, m), 7.51 (2H, d, J=8.5Hz), 8.00 (2H, d, J=8.5Hz)

4) 7-Chloro-5-ethoxycarbonylmethyl-1-(4-nitrobenzoyl)-2,3,4,5-tetrahydro-1H-1-benzazepine NMR (CDCl$_3$, δ): 1.26 (3H, t, J=7.5Hz), 2.72 (2H, dd, J=6, 16Hz), 2.98 (2H, dd, J=6, 16Hz), 4.22 (2H, q, J=7.5Hz), 1.20–4.52 (7H, m), 6.75 (1H, d, J=7.5Hz), 6.95 (1H, m), 7.13 (1H, m), 7.52 (2H, d, J=8.5Hz), 8.02 (2H, d, J=8.5Hz)

5) 2-(4-Methyl-1-piperazinyl)-5-(4-nitrobenzoyl)-3,4-dihydro- 5H-1,5-benzodiazepine NMR (CDCl$_3$, δ): 1.83 (1H, m), 2.33 (3H, s), 2.50 (4H, m), 2.73 (1H, m), 3.62–3.92 (5H, m), 4.77 (1H, m), 6.55 (1H, d, J=7.5Hz), 6.64 (1H, t, J=7.5Hz), 7.02 (1H, d, J=7.5Hz), 7.15 (1H, t, J=7.5Hz), 7.40 (2H, d, J=8.5Hz), 8.00 (2H, d, J=8.5Hz)

PREPARATION 16

To a solution of 2,3,4,5-tetrahydro-1H-1,5-benzodiazepine (300 mg) and triethylamine (615 mg) in dichloromethane (5 ml) was added dropwise a solution of 4-nitrobenzoyl chloride (789 mg) in dichloromethane (5 ml) at ambient temperature, and then the mixture was stirred at ambient temperature for 18 hours. The resulting solution was diluted with dichloromethane and the organic layer was washed successively with 0.5N hydrochloric acid solution, saturated aqueous sodium bicarbonate solution and brine. Drying, filtering and the removal of solvents afforded a crude product. The crude product was triturated with diethyl ether - n-hexane (1:1) to give 1,5-bis(4-nitrobenzoyl)-1,3,4,5-tetrahydro-1H-1,5-benzodiazepine (790 mg) as a yellow powder.

Rf: 0.68 (10% methanol in chloroform)

PREPARATION 17

To a solution of 8-methoxy-11-oxo-6,11- dihydrodibenz[b,e]azepine (150 mg) in N,N-dimethylaniline (1 ml) was added 4-nitrobenzoyl chloride (140 mg) at 110° C. The mixture was stirred for 1 hour at the same temperature and diluted with ethyl acetate. The solution was washed successively with diluted hydrochloric acid and brine. The organic phase was dried over magnesium sulfate, and evaporated in vacuo to give crude 8-methoxy -5-(4-nitrobenzoyl)-11-oxo-6,11-dihydrodibenz[b,e]azepine (240 mg).

NMR (CDCl$_3$, δ): 3.93 (3H, s), 4.80–5.90 (2H, br s), 6.70 (1H, br d, J=8Hz), 6.91–7.08 (2H, m), 7.20–7.46 (4H, m), 8.03 (2H, d, J=8Hz), 8.23–8.35 (1H, m), 8.43 (1H, d, J=8Hz)

Preparation 18

The following compounds were obtained according to a similar manner to that of Preparation 3.

1) 5-(3-Benzyloxy-4-nitrobenzoyl)-1,3,4,5-tetrahydro -1,5-benzodiazepin-2(2H)-one NMR (CDCl$_3$, δ): 2.54–2.66 (1H, m), 2.71–2.88 (1H, m), 3.76–3.91 (1H, m), 4.71–4.92 (1H, m), 4.94–5.17 (2H, m), 6.66 (1H, d, J=9Hz), 6.78 (1H, d, J=9Hz), 6.92 (1H, m), 6.99–7.11 (2H, m), 7.20–7.29 (1H, m), 7.33–7.45 (5H, m), 7.60 (1H, d, J=9Hz)

2) 5-(3-Methyl-4-nitrobenzoyl)-8-methyl-1,3,4,5 -tetrahydro-1,5-benzodiazepin-2(2H)-one NMR (CDCl$_3$, δ): 2.32 (3H, s), 2.49 (3H, s), 2.60–2.89 (2H, m), 3.78–3.92 (1H, m), 4.74–4.93 (1H, m), 6.60 (1H, d, J=8Hz), 6.72 (1H, d, J=8Hz), 6.94 (1H, s), 6.99 (1H, d, J=10Hz), 7.33 (1H, s), 7.69 (1H, d, J=10Hz), 8.22–8.27 (1H, br s)

3) 5-(3-Methoxy-4-nitrobenzoyl)-8-methyl-1,3,4,5 -tetrahydro-1,5-benzodiazepin-2(2H)-one NMR (CDCl$_3$, δ): 2.32 (3H, s), 2.58–2.90 (2H, m), 3.75–3.93 (1H, m), 3.81 (3H, s), 4.73–4.92 (1H, m), 6.63 (1H, d, J=9Hz), 6.70–6.80 (2H, m), 6.94 (1H, s), 7.03 (1H, d, J=1Hz), 7.58 (1H, d, J=8Hz), 8.31 (1H, s 4) 8-Chloro-5-(3-methoxy-4-nitrobenzoyl)-1,3,4,5-tetrahydro-1,5-benzodiazepin-2(2H)-one Rf:0.44 (10% methanol in chloroform)

5) 8-Chloro-5-(3-methyl-4-nitrobenzoyl)-1,3,4,5-tetrahydro-1,5-benzodiazepin-2(2H)-one NMR (CDCl$_3$, δ): 2.50 (3H, s), 2.60–2.84 (2H, m), 3.78–3.93 (1H, m), 4.76–4.90 (1H, m), 6.69 (1H, d, J=9Hz), 6.92 (1H, d, J=9Hz), 7.00 (1H, d, J=9Hz), 7.16 (1H, s), 7.35 (1H, s), 7.73 (1H, d, J=9Hz), 8.45–8.52 (1H, br s)

Preparation 19

To a solution of 2-(2-methylphenyl)benzoic acid (2.12 g) in dichloromethane (20 ml) were added oxalyl chloride (1.7 ml) and two drops of N,N-dimethylformamide at 0° C. and the solution was stirred at ambient temperature for 1 hour. Dichloromethane was evaporated in vacuo to give an acid chloride and the oil was added to a mixture of ethyl 4-amino-3-chlorobenzoate (1.99 g) and pyridine (1.58 g) in dichloromethane (15 ml). The mixture was stirred at ambient temperature for 1 day, washed successively with diluted hydrochloric acid, water and brine, and dried over magnesium sulfate. The solvent was evaporated in vacuo to give ethyl 3-chloro-4-[2-(2-methylphenyl)benzoylamino]-benzoate (4.0 g).

NMR (CDCl$_3$, δ): 1.37 (3H, t, J=7Hz), 2.18 (3H, s), 4.34 (2H, q, J=7Hz), 7.17–7.37 (5H, m), 7.45–7.64 (2H, m), 7.82 (1H, br s), 7.85–7.95 (2H, m), 8.02 (1H, d, J=9Hz), 8.59 (1H, d, J=9Hz)

Preparation 20

The following compounds were obtained according to a similar manner to that of Preparation 19.

1) Ethyl 3-chloro-4-[2-(2,4-dimethylphenyl)-benzoylamino] benzoate

NMR (CDCl$_3$, δ): 1.38 (3H, t, J=7Hz), 2.14 (3H, s), 2.33 (3H, s), 4.34 (2H, q, J=7Hz), 7.02–7.13 (2H, m), 7.15–7.36 (2H, m), 7.43–7.65 (2H, m), 7.82–7.96 (3H, m), 8.02 (1H, d, J=8Hz), 8.63 (1H, d, J=8Hz)

2) Ethyl 4-[2-(2-methylphenyl)benzoylamino]-3-nitrobenzoate

NMR (CDCl$_3$, δ): 1.40 (3H, t, J=7Hz), 2.24 (3H, s), 4.38 (2H, q, J=7Hz), 7.11–7.30 (4H, m), 7.37 (1H, d, J=8Hz), 7.45–7.66 (2H, m), 7.86 (1H, d, J=8Hz), 8.21 (1H, d, J=8Hz), 8.73 (1H, s), 8.86 (1H, d, J=8Hz), 10.16 (1H, br s)

3) Ethyl 4-[2-(2,4-dimethylphenyl)benzoylamino]-2-nitrobenzoate

NMR (CDCl$_3$, δ): 1.32 (3H, t, J=7Hz), 2.06 (3H, s), 2.45 (3H, s), 4.33 (2H, q, J=7Hz), 6.94–7.13 (1H, m), 7.16–7.40 (5H, m), 7.42–7.73 (4H, m), 8.16 (1H, d, J=9Hz)

Preparation 21

To a solution of 2-(4-methylphenyl)benzoic acid (2.12 g) in dichloromethane (20 ml) were added oxalyl chloride (2.02 g) and a few drops of N,N-dimethylformamide and the mixture was stirred at ambient temperature for 1 hour. The solvent was evaporated in vacuo to give an acid chloride and the acid chloride was added to a mixture of methyl 6-aminonicotinate (761 mg) and triethylamine (2.09 ml) in dichloromethane (30 ml). After being stirred at ambient temperature for 6 hours, the solution was washed with water and brine, and dried over magnesium sulfate. The solvent was evaporated in vacuo to give a syrup and the syrup was solidified with diethyl ether to give methyl 6-{N,N-di-[2-(4-methylphenyl)benzoyl]amino}nicotinate (2.22 g).

NMR (CDCl$_3$, δ): 2.41 (6H, s), 3.87 (3H, s), 6.77 (2H, d, J=7.5Hz), 7.06 (2H, dt, J=1.5, 7.5Hz), 7.15–7.34 (9H, m), 7.43 (4H, d, J=8.5Hz), 8.22 (1H, m), 8.78 (1H, m)

Preparation 22

To a mixture of 2-nitroaniline (1.38 g) and triethylamine (1.67 ml) in dichloromethane (30 ml) were added 4-nitrobenzoyl chloride (1.85 g) and the solution was stirred at ambient temperature for 4 hours. The solution was washed successively with 1N hydrochloric acid, saturated aqueous sodium hydrogencarbonate, water and brine, and the organic layer was dried over magnesium sulfate. The solvent was evaporated in vacuo and the residue was solidified with n-hexane to give 2-nitro-N-(4nitrobenzoyl)aniline (1.82 g).

NMR (CDCl$_3$, δ): 7.64–7.83 (2H, m), 8.01 (2H, d, J=8.5Hz), 8.17–8.44 (4H, m)

Preparation 23

The following compound was obtained according to a similar manner to that of Preparation 22.

2-Chloro-3-(4-nitrobenzoyl)aminopyridine

NMR (CDCl$_3$, δ): 7.36 (1H, m), 8.10 (2H, d, J=9Hz), 8.20 (1H, m), 8.40 (2H, d, J=9Hz), 8.43 (1H, br s), 8.88 (1H, d, J=9Hz)

Preparation 24

A mixture of 4-methyl-2-nitroaniline (10.0 g) and ethyl acrylate (9.87 g) in a mixture of concentrated hydrochloric acid (10 ml) and water (8.5 ml) was refluxed for 2 hours and the mixture was cooled to ambient temperature. The solution was basified with concentrated ammonium hydroxide and the resulting solution was extracted with chloroform. Drying over magnesium sulfate, filtering and the removal of solvents afforded N-(2-ethoxycarbonyl- ethyl)-4-methyl-5-nitroaniline (11.3 g) as a red oil.

Rf: 0.79 (10% methanol in chloroform)

Preparation 25

The following compounds were obtained according to a similar manner to that of Preparation 24.

1) 4-Chloro-N-(2-ethoxycarbonylethyl)-2-nitroaniline Rf: 0.78 (10% methanol in chloroform)

2) N-(2-Ethoxycarbonylethyl)-4-methoxy-2-nitroaniline Rf: 0.85 (10% methanol in chloroform)

3) N-(4-Ethoxycarbonylethyl)-2-nitro-4-trifluoromethylaniline Rf: 0.75 (10% methanol in chloroform)

Preparation 26

A mixture of 5-methyl-2-nitroaniline (3.00 g), ethyl bromopropionate (5.35 g) and potassium carbonate (8.18 g) in N,N-dimethylformamide (20 ml) was stirred at 150° C. for 4 hours and the suspension was cooled to ambient temperature. After being filtered, the filtrate was diluted with ethyl acetate and the solution was washed successively with saturated sodium bicarbonate aqueous solution and brine. Drying over magnesium sulfate, filtering and the removal of solvents afforded a crude product. The crude product was triturated with diethyl ether-n-hexane (1:1) to give N-(2- ethoxycarbonylethyl)-5-methyl-2-nitroaniline (2.83 g) as a yellow prisms.

NMR (CDCl$_3$, δ): 1.30 (3H, t, J=8Hz), 2.37 (3H, s), 2.70 (2H, t, J=7Hz), 3.64 (2H, q, J=7Hz), 4.21 (2H, q, J=8Hz), 6.49 (1H, dd, J=1, 9Hz), 6.64 (1H, d, J=1Hz), 8.07 (1H, d, J=9Hz), 8.18–8.28 (1H, br)

Preparation 27

To a solution of 2-nitro-N-(4-nitrobenzoyl)aniline (910 mg) in N,N-dimethylformamide (20 ml) was added sodium hydride (60% in oil, 127 mg) and the solution was stirred at ambient temperature for 30 minutes. Ethyl bromoacetate (0.351 ml) was added to the solution and the mixture was stirred at ambient temperature overnight. The solution was diluted with ethyl acetate (30 ml) and the solution was washed successively with 1N hydrochloric acid, water and brine. The organic phase was dried over magnesium sulfate and the solvent was evaporated in vacuo to give an oil. The oil was solidified with diethyl ether to give [N-ethoxycarbonylmethyl-N-(4-nitrobenzoyl)]-2-nitroaniline (565 mg).

NMR (CDCl$_3$, δ): 1.28 (3H, t, J=7Hz), 3.93 (1H, d, J=17.5Hz), 4.24 (2H, m), 5.15 (1H, d, J=17.5Hz), 7.38–7.52 (4H, m), 7.60 (1H, ddd, J=1, 8, 8Hz), 7.88 (1H, dd, J=1, 8Hz), 8.04 (2H, d, J=8.5Hz)

Preparation 28

To a solution of 2-chloro-3-(4-nitrobenzoyl)aminopyridine (1.93 g) in N,N-dimethylformamide (13 ml) was added sodium hydride (60 % in oil, 585 mg) and the solution was stirred at 0° C. for ten minutes. 3-Dimethylaminopropyl chloride hydrochloride (1.16 g) was added to the solution and the mixture was stirred for 3 hours at 150° C. The solution was diluted with ethyl acetate and the solution was washed with successively with water, saturated aqueous sodium hydrogen carbonate and brine. The organic phase was dried over sodium sulfate and the solvent was evaporated in vacuo. The residue was purified by silica gel column chromatography (80 g, ethyl acetate:n-hexane = 1:3) to give 1-(4-nitrobenzoyl)-5-methyl-2,3,4,5-tetrahydropyrido [3,2-b][1,4]diazepine (450 mg).

NMR (CDCl$_3$, δ): 2.01–2.28 (2H, br s), 3.17 (3H, s), 3.11–3.40 (2H, m), 3.73–3.96 (1H, m), 4.58–4.82 (1H, m), 6.35 (1H, dd, J=9, 9Hz), 6.71 (1H, d, J=9Hz), 7.38 (2H, d, J=9Hz), 7.34–7.56 (1H, m), 8.03 (2H, d, J=9Hz)

Preparation 29

A solution of 1-(4-nitrobenzoyl)-2,3,4,5-tetrahydro-1H-2-benzazepin-5-one (465 mg), hydroxylamine hydrochloride (209 mg) and pyridine (237 mg) in ethanol (10 ml) was stirred for 1.5 hours at 90° C. The solvent was evaporated and diluted with ethyl acetate and the solution was washed with successively water and brine. The organic phase was dried over magnesium sulfate and the solvent was evaporated in vacuo to give crude 5-hydroxyimino-1-(4-nitrobenzoyl)-2,3,4,5-tetrahydro-1H-1-benzazepine (500 mg).

NMR (CDCl$_3$, δ): 1.60–2.23 (2H, m), 2.80–3.05 (2H, m), 3.31–3.56 (1H, m), 4.42–4.73 (1H, m), 6.69 (1H, d, J=8Hz), 7.04–7.20 (1H, m), 7.20–7.33 (1H, m), 7.38 (2H, d, J=8Hz), 7.51 (1H, d, J=8Hz), 7.98 (2H, d, J=8Hz), 9.09 (1H, br s)

Preparation 30

A solution of 5-hydroxyimino-1-(4-nitrobenzoyl)-2,3,4,5-tetrahydro-1H-1-benzazepine (500 mg) in N,N-dimethylformamide (10 ml) was treated with sodium hydride (72 mg, 60% w/w in mineral oil) at 0° C. The reaction mixture was stirred at 0° C. for 5 minutes and then at ambient temperature for 30 minutes. Ethyl bromoacetate (301 mg) was added, and the reaction mixture was stirred for 2 hours. The reaction was quenched with aqueous hydrochloric acid and the mixture was diluted with ethyl acetate. The organic phase was washed with 0.5N hydrochloric acid, water, saturated aqueous sodium hydrogen carbonate, and brine. The organic solution was dried over magnesium sulfate and concentrated to give crude 5-ethoxycarbonylmethoxyimino-1-(4-nitrobenzoyl) -2,3,4,5-tetrahydro-1H-1-benzazepine. This product was taken on without further purification (700 mg).

NMR (CDCl$_3$, δ): 1.31 (3H, t, J=7Hz), 1.62–2.18 (2H, m), 2.86–3.02 (2H, m), 3.28–3.61 (1H, m), 4.25 (2H, q, J=7Hz), 4.46–4.76 (1H, m), 4.80 (2H, s), 6.68 (1H, d, J=8Hz), 7.04–7.32 (2H, m), 7.39 (2H, d, J=8Hz), 7.40–7.56 (1H, m), 7.99 (2H, d, J=8Hz)

Preparation 31

To a solution of 1-ethoxycarbonylmethyl-1,3,4,5-tetrahydro-1,5-benzodiazepin-2(2H)-one (173 mg) in tetrahydrofuran (5 ml) was added diborane dimethylsulfide complex (10 mol solution, 0.5 ml) and the mixture was stirred at ambient temperature for 8 hours. The solution was washed with water and brine, dried over magnesium sulfate. The solvent was evaporated in vacuo and a residue was purified by silica gel column to give 1-ethoxycarbonylmethyl-2,3,4,5-tetrahydro-1H-1,5-benzodiazepine (125 mg) as a pale brown oil.

NMR (CDCl$_3$, δ): 1.30 (3H, t, J=7.5Hz), 1.86 (2H, m), 3.16 (2H, t, J=5Hz), 3.27 (2H, t, J=5Hz), 3.97 (2H, s), 4.24 (2H, q, J=7.5Hz), 6.62–6.82 (4H, m)

Preparation 32

To a solution of naphthalene (15.5 g) in dimethoxyethane (100 ml) was added sodium metal (2.79 g) in portions at 0° C. and the solution was stirred at the same temperature for 1 hour. The naphthilide was added to a solution of 7-chloro -5-ethoxycarbonylmethyl-1-(p-toluenesulfonyl)-2,3,4,5-tetrahydro-1H-1-benzazepine (9.89 g) in dimethoxyethane (400 ml) at −60° C. and the solution was stirred at the same temperature for 30 minutes. The reaction mixture was quenched with water and the solution was extracted with chloroform. The extract was washed with brine and dried over magnesium sulfate. The solvent was evaporated in vacuo to give an oil and the crude oil was purified by silica gel column to give 7-chloro-5-ethoxycarbonylmethyl -2,3,4,5-tetrahydro-1H-1-benzazepine (2.31 g).

NMR (CDCl$_3$, δ): 1.18 (3H, t, J=7.5Hz), 1.51–2.04 (4H, m), 2.67–2.90 (3H, m), 3.26 (1H, m), 3.44 (1H, m), 4.04 (2H, q, J=7.5Hz), 6.70 (1H, d, J=7.5Hz), 6.82 (1H, dt, J=1.5, 7.5Hz), 7.04 (1H, dt, J=1.5, 7.5Hz), 7.14 (1H, dd, J=1.5, 7.5Hz)

Preparation 33

To a solution of ethyl diethylphosphonoacetate (6.10 g) in tetrahydrofuran (50 ml) was added sodium hydride (60% in oil, 599 mg) and the solution was stirred at ambient temperature for 30 minutes. To the solution was added a solution of 1-(4-nitrobenzoyl)-2,3,4,5-tetrahydro -1H-1-benzazepine (3.10 g) in tetrahydrofuran (10 ml) dropwise and the mixture was stirred at ambient temperature for 5 hours. The solution was poured into water and the aqueous solution was extracted with ethyl acetate. The organic phase was washed with water and brine, and dried over magnesium sulfate. The solvent was evaporated in vacuo and the crude product was purified by silica gel column (100 g, 1% methanol in chloroform) to give 5-ethoxycarbonylmethylene-1-(4-nitrobenzoyl) -2,3,4,5-tetrahydro-1H-1-benzazepine (689 mg) and 5-ethoxycarbonylmethyl-1-(4-nitrobenzoyl)-2,3-dihydro -1H-1-benzazepine (905 mg).

5-Ethoxycarbonylmethylene-1-(4-nitrobenzoyl)-2,3,4,5 -tetrahydro-1H-1-benzazepine NMR (CDCl$_3$, δ): 1.37 (3H, t, J=7.5Hz), 1.72–2.20 (2H, m), 2.39–2.80 (1H, m), 3.02 (1H, m), 3.36 (1H, m), 4.06–4.26 (2H, m), 4.50–4.98 (1H, m), 6.10 (1H, d, J=15Hz), 6.63 (1H, d, J=7.5Hz), 7.04 (1H, m), 7.18–7.37 (3H, m), 7.59 (1H, d, J=8Hz), 8.00 (2H, d, J=8.5Hz)

5-Ethoxycarbonylmethyl-1-(4-nitrobenzoyl)-2,3 -dihydro-1H-1-benzazepine

NMR (CDCl$_3$, δ): 1.27 (3H, t, J=7.5Hz), 2.41 (1H, m), 2.68 (1H, m), 3.94 (1H, d, J=17Hz), 3.55 (1H, m), 3.84 (1H, d, J=17Hz), 4.16 (2H, m), 4.80 (1H, m), 6.26 (1H, t, J=5Hz), 6.63 (1H, d, J=7.5Hz), 6.93 (1H, t, J=7.5Hz), 7.21 (1H, t, J=7.5Hz), 7.36 (1H, d, J=7.5Hz), 7.53 (2H, d, J=8.5Hz), 8.01 (2H, d, J=8.5Hz)

Preparation 34

To a mixture of 5-ethoxycarbonylmethylene-1-(4 -nitrobenzoyl)-2,3,4,5-tetrahydro-1H-1-benzazepine (671 mg) and nickel chloride hexahydrate (419 mg) in a mixture of methanol (25 ml) and tetrahydrofuran (25 ml) was added sodium borohydride (601 mg) in portions at 0° C. and the mixture was stirred at the same temperature for 30 minutes. The solution was filtered through a bed of celite and the filtrate was evaporated in vacuo. The residue was dissolved in chloroform and the solution was washed with water and brine, and dried over magnesium sulfate. The solvent was evaporated in vacuo to give a crude oil and the oil was subjected to silica gel column (30 g, 1% methanol in chloroform) to give 1-(4 -aminobenzoyl)-5-ethoxycarbonylmethyl-2,3,4,5-tetrahydro -1H-1-benzazepine (500 mg).

FAB-MASS (m/z): 353 (M+1)

Preparation 35

To a suspension of lithium aluminum hydride (168 mg) in tetrahydrofuran (10 ml) was added dropwise a solution of 5-(3,4-dimethoxybenzenesulfonyl)-1,3,4,5-tetrahydro -1,5-benzodiazepin-2(2H)-one (800 mg) at 0° C. The mixture was refluxed for 2.5 hours, and then the reaction was quenched with methanol. To the resulting mixture was added dropwise 2N sodium hydroxide solution (5 ml), and the mixture was stirred at ambient temperature for 30 minutes. The suspension was filtered through a bed of celite, and then the filtrate was diluted with ethyl acetate. The organic layer was washed with brine. Drying, filtering and the removal or solvents afforded a crude product. The crude product was chromatographed on silica gel (1% methanol in chloroform) to give 1-(3,4 -dimethoxybenzenesulfonyl)-2,3,4,5-tetrahydro-1H-1,5-benzodiazepine (435 mg) as a yellow powder.

NMR (CDCl$_3$, δ): 1.80 (2H, q, J=6Hz), 2.94 (2H, t, J=6Hz), 3.50–3.54 (1H, br), 3.74 (3H, s), 3.75–3.82 (2H, br), 3.92 (3H, s), 6.65 (1H, d, J=8Hz), 6.84 (1H, d, J=8Hz), 6.86 (1H, t, J=8Hz), 6.95 (1H, d, J=4Hz), 7.08 (1H, dd, J=6, 8Hz), 7.35 (1H, dd, J=4, 8Hz), 7.41 (1H, d, J=8Hz)

Preparation 36

A mixture of 1,5-bis(4-nitrobenzoyl)-2,3,4,5 -tetrahydro-1H-1,5-benzodiazepine (737 mg) and iron powder (738 mg) in a mixture of ethanol (10 ml) and acetic acid (1 ml) was refluxed for 2 hours and the solution was cooled to ambient temperature. The mixture was filtered through a bed of celite and the filtrate was evaporated in vacuo. The residue was dissolved in chloroform and the solution was basified with saturated aqueous sodium bicarbonate solution. The solution was filtered through a bed of celite, and then the filtrate was washed with brine. Drying, filtering and the removal of solvents afforded a crude product. The crude product was chromatographed on silica gel (eluent: 2% methanol in chloroform) to give 1,5-bis(4-aminobenzoyl)-2,3,4,5 -tetrahydro-1H-1,5-benzodiazepine as a slightly yellow powder.

NMR (CDCl$_3$, δ): 1.60–1.65 (4H, br s), 1.84–1.98 (2H, br), 3.80–3.88 (4H, br s), 6.49 (4H, d, J=8Hz), 7.02–7.10 (4H, br s), 7.26 (4H, d, J=8Hz)

Preparation 37

A solution of 5-(3-benzyloxy-4-nitrobenzoyl)-1 -ethoxycarbonylmethyl-1,3,4,5-tetrahydro-1,5 -benzodiazepin-2(2H)-one (2.2 g), 10% palladium on carbon (220 mg) in ethanol (30 ml) and 1,4-dioxane (15 ml) was stirred under 4 atmospheric pressure of hydrogen at ambient temperature for 7 hours. The reaction mixture was filtered through a bed of celite, concentrated and purified by silica gel column chromatography (SiO$_2$ 60 g, ethyl acetate:n-hexane = 2:1) to give 5-(4-amino-3 -hydroxybenzoyl)-1-ethoxycarbonylmethyl-1,3,4,5 -tetrahydro-1,5-benzodiazepin-2(2H)-one (1.5 g).

NMR (CDCl$_3$, δ): 1.28 (3H, t, J=7Hz), 2.54–2.67 (1H, m), 2.69–2.84 (1H, m), 3.78–4.03 (3H, m), 4.16–4.32 (3H, m), 4.41 (1H, d, J=10Hz), 4.60–4.77 (1H, m), 4.79 (1H, d, J=10Hz), 6.30 (1H, d, J=7Hz), 6.38 (1H, d, J=7Hz), 6.83 (1H, d, J=7Hz), 6.95–7.06 (1H, m), 7.16–7.33 (3H, m)

Preparation 38

The mixture of ethyl 3-chloro-4-[2-(2-methylphenyl)-benzoylamino] benzoate (4.0 g), 1N sodium hydroxide aqueous solution (15 ml) and ethanol (30 ml) was stirred for 5 hours at ambient temperature. Ethanol was removed in vacuo and the residue was washed with diethyl ether and the aqueous layer was acidified with 1N hydrochloric acid and diluted with ethyl acetate. The solution was washed with brine and dried over magnesium sulfate. Filtering and the removal of solvent afforded crude 3-chloro-4 [2-(2-methylphenyl)benzoylamino]benzoic acid (3.1 g).

NMR (CDCl$_3$+CD$_3$OD, δ): 2.19 (3H, s), 3.06 (2H, br s), 7.19–7.37 (5H, m), 7.45–7.66 (2H, m), 7.85–8.05 (3H, m), 8.57 (1H, d, J=9Hz)

Preparation 39

The following compounds were obtained according to a similar manner to that of Preparation 38.

1 ) 3 -Chloro-4-[ 2-(2,4-dimethylphenyl) benzoylamino] -benzoic acid

NMR (CDCl$_3$, δ): 2.16 (3H, s), 2.33 (3H, s), 6.99–7.14 (2H, m), 7.15–7.36 (2H, m), 7.43–7.66 (2H, m), 7.89–8.11 (4H, m), 8.67 (1H, d, J=8Hz)

2) 4-[2-(2-Methylphenyl)benzoylamino]-3-nitrobenzoic acid

NMR (DMSO-d$_6$, δ): 2.10 (3H, s), 3.13–3.60 (2H, br s), 7.08–7.26 (4H, m), 7.28–7.40 (1H, m), 7.52–7.87 (4H, m), 8.18 (1H, d, J=8Hz), 8.37 (1H, s)

3) 4-[2-(2,4-Dimethylphenyl)benzoylamino]-2-nitrobenzoic acid

NMR (CDCl$_3$+CD$_3$OD, δ): 2.06 (3H, s), 2.42 (3H, s), 7.12–7.25 (3H, m), 7.26–7.38 (2H, m), 7.46 (1H, d, J=2Hz), 7.49–7.66 (2H, m), 7.75 (1H, d, J=9Hz), 8.06 (1H, dd, J=2, 9Hz)

Preparation 40

A solution of methyl 6-{N,N-di[2-(4-methylphenyl)benzoyl] amino}nicotinate (2.10 g) in a mixture of 1N sodium hydroxide solution (40 ml) and methanol (40 ml) was heated at 70° C. for 6 hours and methanol was removed under reduced pressure. The aqueous solution was adjusted to pH 5 with 1N hydrochloric acid and the precipitated solid was filtered. The solid was washed with water and diethyl ether to give 6-(4-methylphenyl)benzoylaminonicotinic acid (831 mg).

NMR (CDCl$_3$+CD$_3$OD, δ): 2.43 (3H, s), 6.80 (1H, d, J=7.5Hz), 7.08 (1H, dt, J=1.5, 7.5Hz), 7.15–7.60 (7H, m), 8.20 (1H, m), 8.77 (1H, m)

Preparation 41

A mixture of 1-(6-chlorohexyl)-5-(4-nitrobenzoyl)-1,3,4,5-tetrahydro-1,5-benzodiazepin-2(2H)-one (675 mg) and potassium phthalimido (291 mg) in N,N-dimethylformamide (15 ml) was stirred at ambient temperature for 8 hours. The mixture was diluted with ethyl acetate and washed successively with 1N hydrochloric acid, aqueous sodium hydrogen carbonate and brine, and dried over magnesium sulfate. The solvent was evaporated in vacuo to give 5-(4-nitrobenzoyl)-1-(6-phthalimidohexyl)-1,3,4,5-tetrahydro-1,5-benzodiazepin-2(2H)-one (758 mg).

NMR (CDCl$_3$, δ): 1.36–1.52 (4H, m), 1.63–1.89 (4H, m), 2.55–2.80 (2H, m), 3.67 (2H, t, J=7.5Hz), 3.77–3.97 (3H, m), 4.78 (1H, m), 6.69 (1H, d, J=7.5Hz), 6.91 (1H, m), 7.24–7.40 (4H, m), 7.65–7.75 (2H, m), 7.78–7.90 (2H, m), 8.04 (2H, d, J=8.5Hz)

Example 1

To a solution of 2-(4-methylphenyl)benzoic acid (140 mg) in dichloromethane (5 ml) were added oxalyl chloride (133 mg) and a few drop of N,N-dimethylformamide and the solution was stirred at ambient temperature for 2 hours. Dichloromethane was evaporated in vacuo to give an acid chloride as an oil and the oil was added to a mixture of 1-(4-aminobenzoyl)-1,2,3,4-tetrahydroquinoline (166 mg) and triethylamine (0.14 ml) in dichloromethane (20 ml). The mixture was stirred at ambient temperature for 2 hours, washed successively with diluted hydrogen chloride, water and brine and dried over magnesium sulfate. The solvent was evaporated in vacuo to give an oil and the oil was subjected to silica gel column (30 g, 1% methanol in chloroform) to give 1-{4-[2-(4-methylphenyl)benzoylamino]benzoyl}-1,2,3,4-tetrahydroquinoline (202 mg) as an amorphous solid.

NMR (CDCl$_3$, δ): 2.03 (2H, tt, J=7, 7Hz), 2.36 (3H, s), 2.82 (2H, t, J=7Hz), 3.88 (2H, t, J=7Hz), 6.67 (1H, d, J=8Hz), 6.87 (1H, dt, J=15, 8Hz), 6.95–7.60 (14H, m), 7.86 (1H, d, J=1.5, 8Hz)

Example 2

The following compounds were obtained according to a similar manner to that of Example 1.

1) 5-Dimethylamino-1-{4-[2-(4-methylphenyl)benzoylamino] benzoyl}-2,3,4,5-tetrahydro-1H-benzazepine NMR (CDCl$_3$, δ): 1.30–3.05 (6H, m), 2.09 (3H, s), 2.32 (3H, s), 2.37 (3H, s), 4.07 (1H, m), 6.54 (1H, d, J=8Hz), 6.83–7.58 (15H, m), 7.83 (1H, d, J=8Hz)

2) 1-{ 4-[ 2-(4-Methylphenyl) benzoylamino]benzoyl} -2,3,4,5-tetrahydro-1H-benzazepine NMR (CDCl$_3$, δ): 1.49 (1H, m), 1.81–2.17 (3H, m), 2.33 (3H, s), 2.64–3.10 (3H, m), 5.00 (1H, m), 6.61 (1H, d, J=8Hz), 6.82–7.55 (15H, m), 7.84 (1H, d, J=8Hz)

3) 1-{4-[2-(4-Trifluoromethylphenyl)benzoylamino]benzoyl} -1,2,3,4-tetrahydroquinoline NMR (CDCl$_3$, δ): 1.99 (2H, tt, J=7, 7Hz), 2.81 (2H, t, J=7Hz), 3.86 (2H, t, J=7Hz), 6.65 (1H, d, J=8Hz), 6.85 (1H, dt, J=1.5, 8Hz), 6.99 (1H, dt, J=1, 8Hz), 7.04–7.26 (6H, m), 7.39–7.65 (7H, m), 7.78 (1H, dt, J=1, 8Hz)

4) 1-{4-[2-(4-Methylphenyl)benzoylamino]benzoyl}-1,2,3,4-tetrahydroquinoxalin-3-one NMR (CDCl$_3$, δ): 2.36 (3H, s), 4.56 (2H, s), 6.68 (1H, d, J=8Hz), 6.79 (1H, ddd, J=1, 8, 8Hz), 7.93 (1H, dd, J=1, 8Hz), 7.00–7.13 (3H, m), 7.19–7.59 (9H, m), 7.88 (1H, dd, J=1, 8Hz), 8.57 (1H, br)

5) 1-{4-[2-(4-Chlorophenyl)benzoylamino]benzoyl}-1,2,3,4-tetrahydroquinoline

NMR (CDCl$_3$, δ): 2.03 (2H, tt, J=7, 7Hz), 2.81 (2H, t, J=7Hz), 3.86 (2H, t, J=7Hz), 6.67 (1H, d, J=8Hz), 6.89 (1H, dd, J=8, 8Hz), 7.00 (1H, dd, J=8, 8Hz), 7.06–7.20 (4H, m), 7.21–7.32 (2H, m), 7.33–7.61 (6H, m), 7.77 (1H, dd, J=8, 2Hz)

6) 1-{4-[2-(4-Methoxyphenyl)benzoylamino]benzoyl}-1,2,3,4-tetrahydroquinoline

NMR (CDCl$_3$, δ): 2.02 (2H, tt, J=7, 7Hz), 2.82 (2H, t, J=7Hz), 3.81 (3H, s), 3.88 (2H, t, J=7Hz), 6.69 (1H, d, J=8Hz), 6.81–7.20 (8H, m), 7.25 (2H, d, J=8Hz), 7.33–7.65 (5H, m), 7.85 (1H, dd, J=8, 2Hz)

7) 1-{4-[4-Methoxy-2-(4-methylphenyl)benzoylamino] benzoyl} -1,2,3,4-tetrahydroquinoline NMR (CDCl$_3$, δ): 2.02 (2H, tt, J=7, 7Hz), 2.48 (3H, s), 2.81 (2H, t, J=7Hz), 3.87 (3H, s), 3.87 (2H, t, J=7Hz), 6.67 (1H, d, J=8Hz), 6.80–7.08 (7H, m), 7.09–7.38 (7H, m), 7.88 (1H, d, J=8Hz)

8) 1-{4-[2-(2,4-Dimethylphenyl)benzoylamino]benzoyl} -1,2,3,4-tetrahydroquinoline NMR (CDCl$_3$, δ): 2.03 (2H, tt, J=7, 7Hz), 2.06 (3H, s), 2.37 (3H, s), 2.83 (2H, t, J=7Hz), 3.86 (2H, t, J=7Hz), 6.66 (1H, d, J=8Hz), 6.78–7.06 (4H, m), 7.07–7.31 (8H, m), 7.42–7.63 (2H, m), 8.12 (1H, dd, J=8, 2Hz)

9) 1-{4-[2-(3,4-Dimethylphenyl)benzoylamino]benzoyl} -1,2,3,4-tetrahydroquinoline NMR (CDCl$_3$, δ): 2.04 (2H, tt, J=7, 7Hz), 2.23 (3H, s), 2.27 (3H, s), 2.83 (2H, t, J=7Hz), 2.88 (2H, t, J=7Hz), 6.65 (1H, d, J=8Hz), 6.86 (1H, dd, J=8, 8Hz), 6.92–7.06 (4H, m), 7.10–7.30 (5H, m), 7.34–7.60 (3H, m), 7.89 (1H, dd, J=8, 2Hz)

10) 1-{4-[2-(4-Hydroxyphenyl)benzoylamino]benzoyl}-1,2,3,4-tetrahydroquinoline

NMR (CDCl$_3$, δ): 2.02 (2H, tt, J=7, 7Hz), 2.30 (1H, br s), 2.83 (2H, t, J=7Hz), 3.86 (2H, t, J=7Hz), 6.68 (1H, d, J=8Hz), 6.77–7.33 (12H, m), 7.35–7.58 (3H, m), 7.81 (1H, d, J=8Hz)

11) 1-{4-[2-(1-Naphthyl)benzoylamino]benzoyl}-1,2,3,4-tetrahydroquinoline

NMR (CDCl$_3$, δ): 1.98 (2H, tt, J=7, 7Hz), 2.78 (2H, t, J=7Hz), 3.82 (2H, t, J=7Hz), 6.51–6.68 (3H, m), 6.81 (1H, dd, J=8, 8Hz), 6.89–7.20 (5H, m), 7.37–7.76 (8H, m), 7.85–8.00 (2H, m), 8.05–8.19 (1H, m)

12) 1-{4-[3-Methoxy-2-(4-methylphenyl)benzoylamino]benzoyl}-1,2,3,4-tetrahydroquinoline NMR (CDCl$_3$, δ): 2.03 (2H, tt, J=7, 7Hz), 2.35 (3H, s), 2.82 (2H, t, J=7Hz), 3.78 (3H, s), 3.86 (2H, t, J=7Hz), 6.66 (1H, d, J=8Hz), 6.80–7.52 (14H, m)

13) 1-{4-[2-(2-Pyridyl)benzoylamino]benzoyl}-1,2,3,4-tetrahydroquinoline

NMR (CDCl$_3$, δ): 2.04 (2H, tt, J=7, 7Hz), 2.83 (2H, t, J=7Hz), 3.89 (2H, t, J=7Hz), 6.72 (1H, d, J=7Hz), 6.87 (1H, dd, J=8, 8Hz), 7.00 (1H, dd, J=8, 8Hz), 7.16 (1H, d, J=8Hz), 7.21–7.65 (9H, m), 7.66–7.88 (2H, m), 8.55–8.66 (1H, m), 8.96 (1H, br s)

14) 1-{4-[2-(4-Ethylphenyl)benzoylamino]benzoyl}-1,2,3,4-tetrahydroquinoline

NMR (CDCl$_3$, δ): 1.22 (3H, t, J=8Hz), 2.04 (2H, tt, J=7, 7Hz), 2.67 (2H, q, J=8Hz), 2.72 (2H, t, J=7Hz), 3.88 (2H, t, J=7Hz), 6.67 (1H, d, J=8Hz), 6.81–7.08 (5H, m), 7.09–7.63 (10H, m), 7.90 (1H, d, J=8Hz)

15) 1-{4-[2-(4-Propylphenyl)benzoylamino]benzoyl}-1,2,3,4-tetrahydroquinoline

NMR (CDCl$_3$, δ): 0.93 (3H, t, J=8Hz), 1.63 (2H, tq, J=8, 8Hz), 2.04 (2H, tt, J=7, 7Hz), 2.61 (2H, t, J=8Hz), 2.84 (2H, t, J=7Hz), 3.88 (2H, t, J=7Hz), 6.67 (1H, d, J=8Hz), 6.81–7.06 (5H, m), 7.11–7.61 (10H, m), 7.92 (1H, d, J=8Hz)

16) 5-Dimethylamino-1-{4-[2-(2,4-dimethylphenyl)benzoylamino]benzoyl}-2,3,4,5-tetrahydro-1H-benzazepine NMR (CDCl$_3$, δ): 1.10–2.50 (16H, m), 2.53–3.62 (2H, m), 3.90–5.25 (1H, m), 6.40–7.62 (15H, m), 8.00–8.15 (1H, m)

17) 5-Dimethylamino-1-{4-[2-(2-pyridyl)benzoylamino]benzoyl}-2,3,4,5-tetrahydro-1H-benzazepine NMR (CDCl$_3$, δ): 1.11–2.54 (10H, m), 2.56–3.68 (2H, m), 3.94–5.25 (1H, m), 6.50–8.97 (17H, m)

18) 1-{4-[2-(2-Azidomethylphenyl)benzoylamino]benzoyl}-1,2,3,4-tetrahydroquinoline NMR (CDCl$_3$, δ): 2.02 (2H, tt, J=7, 7Hz), 2.82 (2H, t, J=7Hz), 3.86 (2H, t, J=7Hz), 4.34 (1H, d, J=12Hz), 4.60 (1H, d, J=12Hz), 6.66 (1H, d, J=8Hz), 6.79–7.47 (11H, m), 7.49–7.60 (2H, m), 7.74 (1H, br s), 7.88–7.98 (1H, m)

19) 1-{4-[2-Phenoxybenzoylamino]benzoyl}-1,2,3,4-tetrahydroquinoline

NMR (CDCl$_3$, δ): 2.05 (2H, tt, J=7, 7Hz), 2.82 (2H, t, J=7Hz), 3.90 (2H, t, J=7Hz), 6.69 (1H, d, J=8Hz), 6.79–6.93 (2H, m), 6.98 (1H, dd, J=8, 8Hz), 7.06–7.62 (12H, m), 8.32 (1H, dd, J=8, 2Hz), 9.73 (1H, br s)

20) 1-{4-[2-(2-Methylphenyl)benzoylamino]benzoyl}-1,2,3,4-tetrahydroquinoline

NMR (CDCl$_3$, δ): 2.04 (2H, tt, J=7, 7Hz), 2.10 (3H, s), 2.80 (2H, t, J=7Hz), 3.86 (2H, t, J=7Hz), 6.68 (1H, d, J=8Hz), 6.79–7.05 (4H, m), 7.08–7.45 (9H, m), 7.46–7.63 (2H, m), 8.11 (1H, dd, J=8, 2Hz)

21) 5-Dimethylamino-1-{4-[2-(2-methylphenyl)benzoylamino]benzoyl}-2,3,4,5-tetrahydro-1H-benzazepine NMR (CDCl$_3$, δ): 1.10–2.80 (13H, m), 2.95–3.65 (2H, m), 3.95–5.20 (1H, m), 6.48–6.77 (1H, m), 6.77–7.80 (15H, m), 8.07 (1H, br d, J=8Hz)

22) 1-Ethoxycarbonylmethyl-5-{4-[2-(4-methylphenyl)benzoylamino]benzoyl}-1,3,4,5-tetrahydro-1,5-benzodiazepin-2(2H)-one mp: 120°–125° C.

NMR (CDCl$_3$, δ): 1.32 (3H, t, J=8Hz), 2.37 and 2.40 (total 3H, s), 2.25–2.90 (2H, m), 3.83 (1H, dd, J=6, 13Hz), 4.18–4.35 (3H, m), 4.60–4.90 (2H, m), 6.75 (1H, d, J=8Hz), 6.95 (4H, d, J=9Hz), 7.08–7.58 (11H, m), 7.82 (1H, dd, J=1, 9Hz)

23) 1-Ethoxycarbonylmethyl-5-{4-[2-(2-methylphenyl)benzoylamino]benzoyl}-1,3,4,5-tetrahydro-1,5-benzodiazepin-2(2H)-one mp: 127°–130° C.

NMR (CDCl$_3$, δ): 1.33 (3H, t, J=7Hz), 2.08 (3H, s), 2.55–2.88 (2H, m), 3.85 (1H, dd, J=5, 11Hz), 4.17–4.35 (3H, m), 4.60–4.83 (1H, m), 4.70 (1H, d, J=17Hz), 6.73 (1H, d, J=9Hz), 6.85–7.04 (1H, m), 6.86 (2H, d, J=9Hz), 7.03–7.19 (3H, m), 7.20–7.43 (6H, m), 7.52 (1H, dt, J=6, 13Hz), 7.53 (1H, dt, J=6, 13Hz), 8.08 (1H, dd, J=1, 8Hz)

24) 1-(2-Dimethylaminoethyl)-5-{4-[2-(4-methylphenyl)benzoylamino]benzoyl}-1,3,4,5-tetrahydro-1,5-benzodiazepin-2(2H)-one mp 178°–181° C.

NMR (CDCl$_3$, δ) 2.29 (6H, s), 2.36 (3H, s), 2.50–2.75 (4H, m), 3.80 (1H, dd, J=5, 13Hz), 3.90–4.19 (2H, m), 4.68 (1H, dt, J=5, 13Hz), 6.70 (1H, d, J=7Hz), 6.90–7.12 (4H, br s), 7.18–7.60 (10H, m), 7.85 (1H, d, J=7Hz)

25) 1-(2-Dimethylaminoethyl)-5-{4-[2-(2-methylphenyl)benzoylamino]benzoyl}-1,3,4,5-tetrahydro-1,5-benzodiazepin-2(2H)-one mp: 210°–213° C.

NMR (CDCl$_3$, δ): 2.10 and 2.11 (total 3H, s), 2.29 (6H, s), 2.50–2.75 (4H, m), 3.70–4.20 (3H, m), 4.65 (1H, dt, J=5, 12Hz), 6.60–6.72 (1H, br), 6.80–7.00 (3H, m), 7.10–7.52 (12H, m), 8.08 (1H, dd, J=1, 7Hz)

26) 5-{4-[2-(2-Methylphenyl)benzoylamino]benzoyl}-1,3,4,5-tetrahydro-1,5-benzodiazepin-2(2H)-one mp: 155°–160° C.

NMR (CDCl$_3$, δ): 2.10 (3H, s), 2.60–2.80 (2H, m), 3.75–3.95 (1H, m), 4.65–4.83 (1H, m), 6.70 (1H, d, J=8Hz), 6.78–6.92 (3H, m), 7.00–7.15 (3H, m), 7.17–7.40 (6H, m), 7.53 (1H, dt, J=1, 8Hz), 7.56 (1H, dt, J=1, 7Hz), 8.02 (1H, dd, J=1, 7Hz)

27) 1-(2-Dimethylaminoethyl)-5-{3-methoxy-4-[2-(4-methylphenyl)benzoylamino]benzoyl}-1,3,4,5-tetrahydro-1,5-benzodiazepin-2(2H)-one mp: 93°–95° C.

NMR (CDCl$_3$, δ): 2.29 (6H, s), 2.39 (3H, s), 2.50–2.78 (4H, m), 3.50 (3H, s), 3.80 (1H, dd, J=5, 13Hz), 3.92–4.05 (2H, m), 4.69 (1H, dt, J=5, 12Hz), 6.60–6.80 (2H, m), 6.90–7.05 (2H, m), 7.15 (2H, d, J=9Hz), 7.23–7.58 (6H, m), 7.78 (2H, dd, J=7, 10Hz), 8.18 (1H, d, J=9Hz)

28) 1-(2-Dimethylaminoethyl)-5-{3-methoxy-4-[2-(2-methylphenyl)benzoylamino]benzoyl}-1,3,4,5-tetrahydro-1,5-benzodiazepin-2(2H)-one mp: 173°–175° C.

NMR (CDCl$_3$, δ): 2.10 and 2.18 (total 3H, s), 2.30 (6H, s), 2.50–2.78 (4H, m), 3.54 (3H, s), 3.80 (1H, dd, J=5, 12Hz), 3.90–4.03 (2H, m), 4.68 (1H, dt, J=5, 12Hz), 6.55–6.76 (2H, m), 6.87–7.00 (8H, m), 7.15–7.33 (5H, m), 7.40–7.58 (3H, m), 7.78–7.87 (1H, br), 7.95 (1H, dd, J=1, 8Hz), 8.15 (1H, d, J=9Hz)

29) 5-(3-Methoxy-4-[2-(4-methylphenyl)benzoylamino]benzoyl}-1,3,4,5-tetrahydro-1,5-benzodiazepin-2(2H)-one mp: 126°–129° C.

NMR CDCl$_3$, δ): 2.35 (3H, s), 2.62–2.80 (2H, br), 3.40 (3H, s), 3.75–4.40 (1H, m), 4.65–4.90 (1H, m), 6.68

(1H, d, J=8Hz), 6.75 (2H, d, J=8Hz), 6.92 (1H, dd, J=1, 9Hz), 7.07–7.58 (7H, m), 7.68 (1H, s), 7.80 (1H, dd, J=1, 6Hz), 7.96 (1H, s), 8.20 (1H, d, J=9Hz)

30) 1-Ethoxycarbonylmethyl-5-{4-[2-(2,4-dimethylphenyl)-benzoylamino]benzoyl}-1,3,4,5-tetrahydro-1,5-benzodiazepin-2(2H)-one NMR (CDCl$_3$, δ): 1.39 (3H, t, J=7.5Hz), 2.00 and 2.03 (total 3H, s), 3.37 (3H, s), 2.52–2.85 (2H, m), 3.81 (1H, m), 4.18–4.34 (3H, m), 4.62–4.83 (2H, m), 6.71 (1H, m), 6.86 (2H, d, J=8.5Hz), 6.97 (1H, m), 7.08–7.28 (8H, m), 7.44–7.59 (2H, m), 8.07 (1H, dd, J=8, 1Hz)

31) 5-{4-[2-(4-Methylphenyl)benzoylamino]benzoyl}-1,3,4,5-tetrahydro-1,5-benzodiazepin-2(2H)-one NMR (CDCl$_3$, δ): 2.33 (3H, s), 2.69 (2H, br), 3.73–4.01 (1H, br), 4.53–4.94 (1H, br), 6.72 (1H, d, J=8Hz), 6.85–7.54 (14H, m), 7.80 (1H, dd, J=8, 1Hz), 8.22 (1H, s)

32) 1-(2-Ethoxycarbonylethyl)-5-{4-[2-(2-methylphenyl)benzoylamino] benzoyl}-1,3,4,5-tetrahydro-1,5-benzodiazepin-2 (2H)-one NMR (CDCl$_3$, δ): 1.27 (3H, t, J=7Hz), 2.00–2.17 (3H, m), 2.43–2.75 (2H, m), 2.76–2.97 (2H, m), 3.67–3.95 (1H, m), 4.05–4.38 (4H, m), 4.48–4.80 (1H, m), 6.60–7.70 (16H, m), 8.09 (1H, br d, J=9Hz)

33) 1-(3-Ethoxycarbonylpropyl)-5-{4-[2-(2-methylphenyl)benzoylamino] benzoyl}-1,3,4,5-tetrahydro-1,5-benzodiazepin-2(2H)-one NMR (CDCl$_3$, δ): 1.26 (3H, t, J=7Hz), 1.82–2.80 (9H, m), 3.80–4.23 (5H, m), 4.50–4.83 (1H, m), 6.60–7.75 (16H, m), 8.07 (1H, br d, J=9Hz)

34) 1-(1-Ethoxycarbonylethyl)-5-{4-[2-(2-methylphenyl)benzoylamino] benzoyl}-1,3,4,5-tetrahydro-1,5-benzodiazepin-2(2H)-one NMR (CDCl$_3$, δ): 1.13 (⅓×3H, t, J=7Hz), 1.31 (⅔×3H, t, J=7Hz), 1.72 (3H, d, J=7Hz), 2.00–2.16 (3H, m), 2.43–2.80 (2H, m), 3.68–4.85 (5H, m), 6.55–7.68 (16H, m), 8.09 (1H, br d, J=9Hz)

35) 1-(t-Butoxycarbonylmethyl)-4-{4-[2-(4-methylphenyl)benzoylamino] benzoyl}-1,2,3,4-tetrahydroquinoxalin-2-one NMR (CDCl$_3$, δ): 1.50 (9H, s), 2.38 (3H, s), 4.59 (2H, s), 4.64 (2H, s), 6.69–6.89 (3H, m), 7.02–7.57 (13H, m), 7.86 (1H, dd, J=8, 1Hz)

36) 1-(3-Dimethylaminopropyl)-5-{4-[2-(2-methylphenyl)benzoylamino] benzoyl}-1,3,4,5-tetrahydro-1,5-benzodiazepin-2(2H)-one NMR (CDCl$_3$, δ): 1.87–1.99 (2H, m), 2.05 and 2.08 (total 3H, s), 2.23 (6H, s), 2.35–2.47 (2H, m), 2.53–2.73 (2H, m), 3.73–4.00 (3H, m), 4.66 (1H, m), 6.70 (1H, br), 6.82–6.99 (2H, m), 7.04–7.15 (2H, m), 7.21–7.38 (8H, m), 7.45–7.61 (2H, m), 8.08 (1H, d, J=8Hz)

37) 5-{ 4-[ 2-(2-Methylphenyl)benzoylamino]benzoyl }-1-(4phthaloylaminobutyl) -1,3,4,5-tetrahydro-1,5-benzodiazepin-2 (2H)-one NMR (CDCl$_3$, δ): 1.73–1.89 (4H, m), 2.06 and 2.08 (total 3H, s), 2.45–2.72 (2H, m), 3.67–4.01 (5H, m), 4.65 (1H, m), 6.69 (1H, br), 6.86 (2H, d, J=8.5Hz), 6.94 (1H, m), 7.02–7.13 (3H, m), 7.19–7.35 (7H, m), 7.45–7.59 (2H, m), 7.66–7.73 (2H, m), 7.78–7.85 (2H, m), 8.07 (1H, dd, J=8, 1Hz)

38) 4-{4-[2-(4-Methylphenyl)benzoylamino]benzoyl}-1-(3-phthaloylaminopropyl)-1,2,3,4-tetrahydroquinoxalin-2-one NMR (CDCl$_3$, δ): 2.16 (2H, tt, J=7.5, 7.5Hz), 2.33 (3H, s), 3.81 (2H, t, J=7.5Hz), 4.12 (2H, t, J=7.5Hz), 4.51 (2H, s), 6.71 (1H, d, J=8Hz), 6.80 (1H, dt, J=1, 8Hz), 7.01–7.55 (3H, m), 7.73 (2H, m), 7.80–7.88 (4H, m)

39) 1-(3-Dimethylaminopropyl)-4-{ 4-[ 2-(4-methylphenyl)benzoylamino] benzoyl} -1,2,3,4 -tetrahydroquinoxalin-2-one NMR (CDCl$_3$, δ): 1.86 (2H, tt, J=7.5, 7.5Hz), 2.22 (6H, s), 2.36 (3H, s), 2.39 (2H, t, J=7.5Hz), 4.05 (2H, t, J=7.5Hz), 4.54 (2H, s), 6.69–6.87 (2H, m), 7.01–7.57 (14H, m), 7.86 (1H, d, J=8Hz)

40) 1-(3-Dimethylaminopropyl)-4-{2-(2-methylphenyl)benzoylamino] benzoyl}-1,2,3,4-tetrahydroquinoxalin-2-one NMR (CDCl$_3$, δ): 1.80–1.95 (2H, m), 2.10 (3H, s), 2.24 (6H, s), 2.37 (2H, t, J=7Hz), 4.06 (2H, t, J=7Hz), 4.51 (2H, s), 6.67–6.84 (2H, m), 6.98 (2H, d, J=8.5Hz), 7.08–7.40 (10H, m), 7.48–7.61 (2H, m), 8.12 (1H, dd, J=2, 8Hz)

41) 1-(2-Dimethylaminoethyl)-4-{4-[2-(4-methylphenyl)benzoylamino] benzoyl}-1,2,3,4-tetrahydroquinoxalin-2-one NMR (CDCl$_3$, δ): 2.30 (6H, s), 2.37 (3H, s), 2.59 (2H, t, J=7Hz), 4.15 (2H, t, J=7Hz), 4.52 (2H, s), 6.70 (1H, d, J=8Hz), 6.81 (1H, m), 7.02–7.58 (14H, m), 7.88 (1H, dd, J=1, 8Hz)

42) 1 -(2 -Dimethylaminoethyl)-4 -{ 4 -[ 2 -(2 -methylphenyl)benzoylamino] benzoyl } -1,2,3,4-tetrahydroquinoxalin -2 -one NMR (CDCl$_3$, δ): 2.11 (3H, s), 2.30 (6H, s), 2.60 (2H, t, J=7Hz), 4.15 (2H, t, J=7Hz), 4.52 (2H, s), 6.67–6.84 (2H, m), 6.98 (2H, d, J=8.5Hz), 7.12–7.40 (10H, m), 7.48–7.61 (2H, m), 8.12 (1H, dd, J=8, 2Hz)

43) 1-(2-Dimethylaminoethyl)-4-{3-methoxy-4-[2-(4methylphenyl)benzoylamino] benzoyl}-1,2,3,4-tetrahydroquinoxalin-2-one NMR (CDCl$_3$, δ): 2.15 (3H, s), 2.32 (6H, s), 2.61 (2H, t, J=7Hz), 3.53 (3H, s), 4.15 (2H, t, J=7Hz), 4.53 (2H, m), 6.68–6.86 (3H, m), 6.93 (1H, d, J=1Hz), 7.13–7.17 (2H, m), 7.21–7.30 (4H, m), 7.43–7.57 (2H, m), 7.87 (1H, s), 7.99 (1H, dd, J=8, 1Hz), 8.31 (1H, d, J=8Hz)

44) 4-{ 4-[ 2-(2-Methylphenyl) benzoylamino]benzoyl}-1-(3piperidinopropyl) -1,2,3,4-tetrahydroquinoxalin-2-one NMR (CDCl$_3$, δ): 1.40–1.50 (2H, m), 1.55–1.72 (4H, m), 1.84–2.00 (2H, m), 2.09 (3H, s), 2.35–2.46 (6H, m), 4.04 (2H, t, J=7Hz), 4.52 (2H, s), 6.68–6.82 (2H, m), 6.98 (2H, d, J=8.5Hz), 7.01–7.41 (9H, m), 7.48–7.61 (2H, m), 8.12 (1H, dd, J=1, 8Hz)

45) 1-{4-[2-(4-Fluoro-2-methylphenyl)benzoylamino] benzoyl} -1,2,3,4-tetrahydroquinoline NMR (CDCl$_3$, δ): 1.96–2.11 (2H, m), 2.11 (3H, s), 2.84 (2H, t, J=7Hz), 3.88 (2H, t, J=7Hz), 6.67 (1H, d, J=8Hz), 6.86 (1H, dd, J=8, 8Hz), 6.94–7.42 (11H, m), 7.45–7.65 (2H, m), 7.98–8.10 (1H, m)

46) 1-{4-[2-(2-Ethylphenyl)benzoylamino]benzoyl}-1,2,3,4tetrahydroquinoline

NMR (CDCl$_3$, δ): 1.00 (3H, t, J=8Hz), 2.02 (2H, tt, J=7, 7Hz), 2.44 (2H, q, J=8Hz), 2.82 (2H, t, J=7Hz), 3.87 (2H, t, J=7Hz), 6.66 (1H, d, J=9Hz), 6.77–7.06 (5H, m), 7.07–7.64 (10H, m), 8.06–8.23 (1H, m)

47) 1-{4-[2-Fluoro-6-(2-methylphenyl)benzoylamino] benzoyl} -1,2,3,4-tetrahydroquinoline NMR (CDCl$_3$, δ): 2.03 (2H, tt, J=7, 7Hz), 2.16 (3H, s), 2.81 (2H, t, J=7Hz), 3.86 (2H, t, J=7Hz), 6.68 (1H, d, J=8Hz), 6.88 (1H, dd, J=8, 8Hz), 7.00 (1H, dd, J=8, 8Hz), 7.05–7.63 (13H, m)

48) 1-{4-[2-(2,6-Dimethylphenyl)benzoylamino]benzoyl} -1,2,3,4-tetrahydroquinoline NMR (CDCl$_3$, δ): 2.03 (6H, s), 1.95–2.14 (2H, m), 2.82 (2H, t, J=7Hz), 3.85 (2H, t, J=7Hz), 6.68 (1H, d, J=8Hz), 6.80–7.05 (4H, m), 7.10–7.40 (7H, m), 7.42–7.68 (3H, m), 8.31 (1H, d, J=8Hz)

49) 1-{4-[2-(2-Cyanophenyl)benzoylamino]benzoyl}-1,2,3,4tetrahydroquinoline

NMR (CDCl₃, δ): 1.90–2.14 (2H, m), 2.84 (2H, t, J=7Hz), 3.87 (2H, t, J=7Hz), 6.71 (1H, d, J=8Hz), 6.88 (1H, dd, J=8, 8Hz), 7.00 (1H, dd, J=8, 8Hz), 7.14 (1H, d, J=8Hz), 7.20–7.85 (13H, m)

50) 7,8-Dimethyl-1-ethoxycarbonylmethyl-5-{4-[2-(4methylphenyl)benzoylamino] benzoyl}-1,3,4,5 -tetrahydro-1,5-benzodiazepin-2(2H)-one Rf: 0.64 (10% methanol in chloroform)

51) 1-Ethoxycarbonylmethyl-7-methyl-5-{4-[2-(4methylphenyl)benzoylamino] benzoyl}-1,3,4,5 -tetrahydro-1,5-benzodiazepin-2(2H)-one NMR (CDCl₃, δ): 1.30 (3H, t, J=8Hz), 2.10 (3H, s), 2.38 (3H, s), 2.53–2.85 (2H, m), 3.80 (1H, dd, J=5, 12Hz), 4.13–4.33 (3H, m), 4.59–4.78 (1H, m), 4.77 (1H, d, J=17Hz), 6.50–6.59 (1H, br), 6.90–7.33 (10H, m), 7.38–7.59 (3H, m), 7.83 (1H, dd, J=1, 8Hz)

52) 8-Chloro-1-ethoxycarbonylmethyl-5-{4-[2-(4methylphenyl)benzoylamino] benzoyl}-1,3,4,5 -tetrahydro-1,5-benzodiazepin-2(2H)-one NMR (CDCl₃, δ): 1.32 (3H, t, J=8Hz), 2.38 (3H, s), 2.60–2.80 (2H, m), 3.74–3.88 (1H, m), 4.15–4.36 (3H, m), 4.56–4.80 (1H, m), 4.76 (1H, d, J=17Hz), 6.68 (1H, d, J=8Hz), 6.92–7.04 (4H, m), 7.12 (2H, d, J=8Hz), 7.18–7.37 (4H, m), 7.38–7.58 (3H, m), 7.84 (1H, dd, J=1, 8Hz)

53) 8-Chloro-1-ethoxycarbonylmethyl-5-{3-methyl-4-[2-(4methylphenyl)benzoylamino] benzoyl}-1,3,4,5 -tetrahydro-1,5-benzodiazepin-2(2H)-one Rf: 0.74 (10% methanol in chloroform)

54) 8-Chloro-1-ethoxycarbonylmethyl-5-{3-methoxy-4-[2-(4methylphenyl)benzoylamino] benzoyl}-1,3,4,5 -tetrahydro-1,5-benzodiazepin-2(2H)-one Rf: 0.68 (10% methanol in chloroform)

55) 1-Ethoxycarbonylmethyl-5-{3-methoxy-4-[2-(4methylphenyl)benzoylamino] benzoyl}-8-methyl-1,3,4,5 -tetrahydro-1,5-benzodiazepin-2(2H)-one NMR (CDCl₃, δ): 1.32 (3H, t, J=8Hz), 2.33 (3H, s), 2.36 (3H, s), 2.54–2.89 (2H, m), 3.49 (3H, s), 3.80 (1H, dd, J=5, 13Hz), 4.15–4.36 (3H, m), 4.60–4.82 (1H, m), 4.77 (1H, d, J=17Hz), 6.52–6.66 (2H, m), 6.78 (1H, d, J=8Hz), 6.94 (1H, s), 7.06 (1H, s), 7.11–7.34 (3H, m), 7.37–7.57 (3H, m), 7.73–7.85 (2H, m), 8.17 (1H, d, J=9Hz)

56) 5-{ 4-[ 2-(2,4-Dimethylphenyl)benzoylamino]-3methoxybenzoyl) -1 -ethoxycarbonylmethyl-8 -methyl 1,3,4,5-tetrahydro-1,5-benzodiazepin-2 (2H)-one NMR (CDCl₃, δ): 1.30 (3H, t, J=8Hz), 2.05 and 2.13 (total 3H, s), 2.30 (3H, s), 2.32 (3H, s), 2.54–2.82 (2H, m), 3.53 (3H, s), 3.72–3.86 (1H, m), 4.14–4.33 (3H, s), 4.60–4.82 (1H, m), 4.76 (1H, d, J=16Hz), 6.45–6.66 (2H, m), 6.76 (1H, d, J=8Hz), 6.89–7.30 (4H, m), 7.42–7.55 (3H, m), 7.86–8.02 (2H, m), 8.18 (1H, d, J=8Hz)

57) 1-Ethoxycarbonylmethyl-8-methyl-5-{4-[2-(4methylphenyl)benzoylamino] benzoyl}-1,3,4,5 -tetrahydro-1,5-benzodiazepin-2(2H)-one NMR (CDCl₃, δ): 1.30 (3H, t, J=8Hz), 2.32 (3H, s), 2.36 (3H, s), 2.55–2.84 (2H, m), 3.72–3.87 (1H, m), 4.15–4.34 (3H, m), 4.60–4.83 (1H, m), 4.79 (1H, d, J=17Hz), 6.56–6.65 (1H, m), 6.72–6.81 (1H, m), 6.90–7.58 (12H, m), 7.84 (1H, dd, J=1, 8Hz)

58) 1-Ethoxycarbonylmethyl-8-methyl-5-{3-methyl-4-[2-(4methylphenyl)benzoylamino] benzoyl}-1,3,4,5 -tetrahydro-1,5-benzodiazepin-2(2H)-one Rf: 0.64 (10% methanol in chloroform)

59) 1-Ethoxycarbonylmethyl-8-methoxy-5-{4-[2-(4methylphenyl)benzoylamino] benzoyl}-1,3,4,5 -tetrahydro-1,5-benzodiazepin-2(2H)-one NMR (CDCl₃, δ): 1.31 (3H, t, J=8Hz), 2.38 (3H, s), 2.55–2.84 (2H, m), 3.63–3.80 (1H, m), 3.75 (3H, s), 4.10–4.32 (3H, m), 4.60–4.82 (1H, m), 4.80 (1H, d, J=17Hz), 6.45–6.70 (2H, m), 6.78 (1H, s), 6.92–7.57 (11H, m), 7.83 (1H, dd, J=1, 8Hz)

60) 5-{2-Chloro-4-[2-(2,4-dimethylphenyl)benzoylamino]benzoyl} -1-ethoxycarbonylmethyl-1,3,4,5-tetrahydro -1,5-benzodiazepin-2(2H)-one NMR (CDCl₃, δ): 1.34 (3H, t, J=7Hz), 2.02 and 2.06 (total 3H, s), 2.40 (3H, s), 2.52–2.89 (2H, m), 3.72–3.88 (1H, m), 4.00 (1H, d, J=16Hz), 4.30 (2H, q, J=7Hz), 4.84 (1H, d, J=16Hz), 4.77–5.01 (1H, m), 6.68–7.68 (14H, m), 8.01–8.11 (1H, m)

61) 1-Ethoxycarbonylmethyl-5-{3-methoxy-4-[2-(4methylphenyl)benzoylamino] benzoyl}-1,3,4,5 -tetrahydro-1,5-benzodiazepin-2(2H)-one NMR (CDCl₃, δ): 1.30 (3H, t, J=7Hz), 2.34 (3H, s), 2.52–2.92 (2H, m), 3.45 (3H, s), 3.74–3.95 (1H, m), 4.15–4.37 (3H, m), 4.57–4.89 (2H, m), 6.61 (1H, d, J=9Hz), 6.76 (1H, d, J=9Hz), 6.91 (1H, s), 6.94–7.07 (1H, m), 7.09–7.67 (9H, m), 7.74 (1H, br s), 7.81 (1H, d, J=9Hz), 8.19 (1H, d, J=9Hz)

62) 1-Ethoxycarbonylmethyl-5-{3-methoxy-4-[2-(2methylphenyl)benzoylamino] benzoyl}-1,3,4,5 -tetrahydro-1,5-benzodiazepin-2(2H)-one NMR (CDCl₃, δ): 1.31 (3H, t, J=7Hz), 2.08 and 2.13 (total 3H, s), 2.52–2.90 (2H, m), 3.48 (3H, s), 3.74–3.92 (1H, m), 4.10–4.37 (3H, m), 4.57–4.89 (2H, m), 6.43–7.59 (13H, m), 7.81 (1H, br s), 7.96 (1H, d, J=9Hz), 8.18 (1H, d, J=9Hz)

63) 1-Ethoxycarbonylmethyl-5-{3-methoxy-4-[2-(2,4dimethylphenyl)benzoylamino] benzoyl}-1,3,4,5 -tetrahydro-1,5-benzodiazepin-2(2H)-one NMR (CDCl₃, δ): 1.30 (3H, t, J=7Hz), 2.04 and 2.10 (total 3H, s), 2.34 (3H, s), 2.50–2.92 (2H, m), 3.49 (3H, s), 3.74–3.94 (1H, m), 4.13–4.40 (3H, m), 4.57–4.91 (2H, m), 6.46–6.68 (1H, m), 6.68–7.34 (8H, m), 7.34–7.59 (3H, m), 7.88 (1H, s), 7.97 (1H, d, J=9Hz), 8.22 (1H, d, J=9Hz)

64) 5-{ 4-[ 2-(2,6-Dimethylphenyl) benzoylamino]benzoyl }-1 -ethoxycarbonylmethyl-1,3,4,5-tetrahydro-1,5 -benzodiazepin-2 (2H )-one Rf: 0.57 (10% methanol in chloroform)

65) 3-Methyl-1-{4-[2-(2-methylphenyl)benzoylamino] benzoyl} -1,2,3,5-tetrahydro-1,3-benzodiazepin-4(4H)-one NMR (CDCl₃, δ): 2.08 (3H, s), 3.06 (3H, s), 4.07 (2H, s), 5.35 (2H, s), 6.60 (1H, d, J=9Hz), 6.84–7.00 (3H, m), 7.04–7.44 (10H, m), 7.45–7.65 (2H, m), 8.11 (1H, d, J=9Hz)

66) 3-Methyl-1-{4-[2-(4-methylphenyl)benzoylamino] benzoyl} -1,2,3,5-tetrahydro-1,3-benzodiazepin-4(4H)one NMR (CDCl₃, δ): 2.36 (3H, s), 3.08 (3H, s), 4.08 (2H, s), 5.36 (2H, s), 6.62 (1H, d, J=9Hz), 6.89–7.60 (15H, m), 7.85 (1H, d, J=9Hz)

67) 5 -{ 4 -[ 2 -(4 -Methylphenyl) benzoylamino] benzoyl } -2,3,4,5-tetrahydro-1,5-benzodiazepine-2 (2H)-thione NMR (CDCl₃, δ): 2.35 (3H, s), 2.94–3.23 (2H, m), 3.70–3.83 (1H, m), 4.66–4.90 (1H, m), 6.68–6.80 (1H, m), 6.85–7.62 (15H, m), 7.79 (1H, d, J=9Hz)

68) 5-Ethoxycarbonylmethoxyimino-1-{4-[2-(4 -methylphenyl)benzoylamino]benzoyl}-2,3,4,5 -tetrahydro-1H-1-benzazepine NMR (CDCl$_3$, δ): 1.28 (3H, t, J=7Hz), 1.61–2.17 (2H, m), 2.36 (3H, s), 2.74–3.06 (2H, m), 3.15–3.50 (1H, br s), 4.23 (2H, q, J=7Hz), 4.31–4.63 (1H, br s), 4.78 (2H, s), 6.65 (1H, d, J=8Hz), 6.79–7.63 (15H, m), 7.82 (1H, d, J=8Hz)

69) 8-Methoxy-5-{4-[2-(4-methylphenyl)benzoylamino] benzoyl} -11-oxo-6,11-dihydrodibenz[b,e]azepine NMR (CDCl$_3$+CD$_3$OD, δ): 2.32 (3H, s), 3.92 (3H, s), 4.75–5.90 (2H, br s), 6.72 (1H, d, J=8Hz), 6.90–7.20 (8H, m), 7.23–7.59 (8H, m), 7.78 (1H, d, J=8Hz), 8.27 (1H, d, J=8Hz), 8.38 (1H, d, J=8Hz)

70) 1-Ethoxycarbonylmethyl-5-{3-hydroxy-4-[2-(4methylphenyl)benzoylamino] benzoyl}-1,3,4,5 -tetrahyro-1,5-benzodiazepin-2(2H)-one NMR (CDCl$_3$, δ): 1.30 (3H, t, J=7Hz), 2.38 (3H, s), 2.54–2.66 (1H, m), 2.66–2.84 (1H, m), 2.86–2.97 (1H, m), 3.72–3.89 (1H, m), 4.18–4.36 (3H, m), 4.60–4.77 (1H, m), 4.81 (1H, d, J=10Hz), 6.26 (1H, d, J=8Hz), 6.56–7.06 (4H, m), 7.12–7.88 (11H, m)

71) 5-Methyl-1-{4-[2-(4-methylphenyl)benzoylamino] benzoyl} -2,3,4,5-tetrahydropyrido[3,2-b][1,4]diazepine NMR (CDCl$_3$, δ): 1.96–2.19 (2H, m), 2.36 (3H, s), 3.14 (3H, s), 2.98–3.38 (2H, m), 3.70–3.96 (1H, m), 4.38–4.78 (1H, m), 6.30–6.39 (1H, m), 6.66–6.75 (1H, m), 6.85–7.01 (3H, m), 7.06–7.23 (4H, m), 7.24–7.35 (2H, m), 7.36–7.56 (3H, m), 7.85 (1H, d, J=9Hz), 7.97–8.03 (1H, m)

72) 4,4-Dimethyl-1-ethoxycarbonylmethyl-5-{4-[2-(4methylphenyl)benzoylamino] benzoyl}-1,3,4,5 -tetrahydro-1,5-benzodiazepin-2(2H)-one Rf: 0.78 (10% methanol in chloroform)

73) 1-Ethoxycarbonylmethyl-4-methyl-5-{4-[2-(4methylphenyl)benzoylamino] benzoyl}-1,3,4,5 -tetrahydro-1,5-benzodiazepin-2(2H)-one Rf: 0.70 (10% methanol in chloroform)

74) 1-(3,4-Dimethoxybenzenesulfonyl)-5-{4-[2-(4methylphenyl)benzoylamino] benzoyl}-2,3,4,5 -tetrahydro-1H-1,5-benzodiazepine NMR (CDCl$_3$, δ): 1.81–1.92 (2H, m), 1.86 (3H, s), 2.81–2.92 (2H, m), 3.76 (3H, s), 3.93 (3H, s), 4.02–4.18 (2H, m), 6.68–6.73 (1H, br), 6.87–7.03 (6H, m), 7.17–7.60 (12H, m), 7.83 (1H, d, J=8Hz)

75) 1-Ethoxycarbonylmethyl-5-{4-[2-(4-methylphenyl)benzoylamino] benzoyl}-8-trifluoromethyl-1,3,4,5 -tetrahydro-1,5-benzodiazepin-2(2H)-one Rf: 0.76 (10% methanol in chloroform)

76) 1-Ethoxycarbonylmethyl-5-{4-[2-(3-methylphenyl)benzoylamino] benzoyl}-1,3,4,5-tetrahydro-1,5 -benzodiazepin-2(2H)-one NMR (CDCl$_3$, δ): 1.30 (3H, t, J=7.5Hz), 2.30 (3H, s), 2.56–2.89 (2H, m), 3.82 (1H, m), 4.17–4.33 (3H, m), 4.62–4.84 (2H, m), 6.72 (1H, d, J=7.5Hz), 6.89–7.01 (4H, m), 7.08–7.57 (11H, m), 7.85 (1H, dd, J=7.5, 1.5Hz)

77) 5-{ 4-[ 2-(2-Methylphenyl) benzoylamino]benzoyl}-1-(3-pyridylmethyl) -1,3,4,5-tetrahydro-1,5-benzodiazepin -2(2H)-one NMR (CDCl$_3$, δ): 2.07 (3H, s), 2.58–2.83 (2H, m), 3.82 (1H, m), 4.69 (1H, m), 4.92 (1H, dd, J=9, 15Hz), 5.42 (1H, dd, J=5, 15Hz), 6.49–6.72 (4H, m), 6.92 (1H, t, J=7.5Hz), 7.10 (1H, s), 7.17–7.40 (9H, m), 7.48–7.61 (2H, m), 7.78 (1H, d, J=7.5Hz), 8.08 (1H, dd, J=1.5, 7.5Hz), 8.46 (1H, m), 8.57 (1H, m)

78) 7,8-Dimethyl-5-{ 4-[ 2-(2,6-dimethylphenyl)benzoylamino ] benzoyl}-1-ethoxycarbonylmethyl-1,3,4,5 -tetrahydro-1,5-benzodiazepin-2(2H)-one NMR (CDCl$_3$, δ): 1.29 (3H, t, J=7.5Hz), 1.96 (3H, s), 1.99 (3H, s), 2.02 (3H, s), 2.20 (3H, s), 2.47–2.82 (2H, m), 3.76 (1H, m), 4.12–4.33 (3H, m), 4.65 (1H, m), 4.78 (1H, d, J=15Hz), 6.46 (1H, br), 6.85 (2H, d, J=8.5Hz), 6.98 (1H, s), 7.08–7.36 (6H, m), 7.43 (1H, s), 7.48–7.62 (2H, m), 8.27 (1H, dd, J=1.5, 7.5Hz)

79) 1-Ethoxycarbonylmethyl-5-{4-[2-(4-methylphenyl)benzoylamino] benzoyl}-2,3,4,5-tetrahydro-1H-1,5benzodiazepine NMR (CDCl$_3$, δ): 1.31 (3H, t, J=7.5Hz), 1.95 (1H, m), 2.09 (1H, m), 2.33 (3H, s), 3.08–3.23 (2H, m), 3.65 (1H, m), 3.98 (1H, d, J=17.5Hz), 4.12 (1H, d, J=17.5Hz), 4.26 (2H, q, J=7.5Hz), 4.68 (1H, m), 6.54 (2H, m), 6.71 (1H, d, J=7.5Hz), 6.86–6.93 (3H, m), 7.03 (1H, m), 7.14–7.55 (10H, m), 7.82 (1H, dd, J=1.5, 7.5Hz)

80) 1-(3 -Dimethylaminopropyl)-5-{ 4-[ 2-(4-methylphenyl) benzoylamino ]benzoyl}-1,3,4,5 -tetrahydro-1,5 -benzodiazepin-2 (2H )-one NMR (CDCl$_3$, δ): 1.86–2.05 (2H, m), 2.23 (6H, s), 2.37 (3H, s), 2.37–2.42 (2H, m), 2.50–2.76 (2H, m), 3.23–4.02 (3H, m), 4.57 (1H, m), 6.72 (1H, br), 6.90–7.02 (3H, m), 7.02–7.56 (13H, m), 7.84 (1H, dd, J=1.5, 7.5Hz)

81) 5-{4-[2-(2,6-Dimethylphenyl)benzoylamino]benzoyl}-1 -ethoxycarbonylmethyl-1,3,4,5-tetrahydro-1,5 -benzodiazepin-2(2H)-one NMR (CDCl$_3$, δ): 1.27 (3H, t, J=7.5Hz), 2.05 (3H, s), 2.21 (3H, s), 2.47–2.85 (2H, m), 3.77 (1H, m), 4.15–4.37 (3H, m), 4.66 (1H, m), 4.76 (1H, d, J=15Hz), 6.46 (1H, br), 6.87 (2H, d, J=8.5Hz), 6.98 (1H, s), 7.11–7.35 (6H, m), 7.44 (1H, s), 7.50–7.63 (2H, m), 8.25 (1H, dd, J=1.5, 7.5Hz)

82) 5-{ 4-[ 2-(4-Methylphenyl) benzoylamino]benzoyl }-1-(6 -phthalimidohexyl)-1, 3,4,5-tetrahydro-1,5 -benzodiazepin-2(2H)-one NMR (CDCl$_3$, δ): 1.32–1.47 (4H, m), 1.57–1.78 (4H, m), 2.33 (3H, s), 2.50–2.72 (2H, m), 3.60–3.99 (4H, m), 4.63 (1H, m), 4.65 (1H, m), 6.74 (1H, d, J=7.5Hz), 6.95 (1H, m), 7.06–7.64 (11H, m), 7.72–7.89 (4H, m)

83) 1-(2-Acetoxyethyl)-5-{ 4-[ 2-(4-methylphenyl)benzoylamino ]benzoyl} -1,3,4,5-tetrahydro-1,5 -benzodiazepin-2 (2H )-one NMR (CDCl$_3$, δ): 2.03 (3H, s), 2.36 (3H, s), 2.50–2.78 (2H, m), 3.80 (1H, dd, J=6, 12.5Hz), 4.15 (2H, m), 4.41 (2H, m), 4.69 (1H, dt, J=6, 12.5Hz), 6.76 (1H, d, J=7.5Hz), 6.92–7.03 (4H, m), 7.10–7.57 (11H, m), 7.82 (1H, dd, J=1.5, 7.5Hz)

84) 1-Ethoxycarbonylmethyl-5-{4-[2-(2 -trifluoromethylphenyl)benzoylamino]benzoyl}-1,3,4,5 -tetrahydro-1,5-benzodiazepin-2(2H)-one NMR (CDCl$_3$, δ): 1.31 (3H, t, 7.5Hz), 2.52–2.88 (2H, m), 3.81 (1H, m), 4.15–4.82 (3H, m), 4.68 (1H, m), 4.78 (1H, d, J=17Hz), 6.70 (1H, d, J=7.5Hz), 6.90–7.36 (7H, m), 7.43–7.58 (4H, m), 7.77 (2H, m)

85) 1-Ethoxycarbonylmethyl-5-{4-[2-(2,4,6trimethylphenyl)benzoylamino] benzoyl}-1,3,4,5 -tetrahydro-1,5-benzodiazepin-2(2H)-one NMR (CDCl$_3$, δ): 1.31 (3H, t, J=7.5Hz), 1.93 (3H, s), 1.97 (3H, s), 2.37 (3H, s), 2.52–2.89 (2H, m), 3.82 (1H, m), 4.14–4.33 (3H, m), 4.70 (1H, m), 4.81 (1H, d, J=17Hz), 6.72 (1H, d, J=7.5Hz), 6.85 (1H, d, J=8.5Hz), 6.97 (1H, m), 7.01–7.17 (4H, m), 7.26 (2H, d, J=8.5Hz), 7.27 (1H, s), 7.44–7.60 (3H, m), 8.27 (1H, m)

86) 1-{4-[2-(2-Methylphenyl)benzoylamino]benzoyl} -2,3,4,5-tetrahydro-1H-1-benzazepin-5-one NMR (CDCl₃, δ): 2.06 (3H, s), 2.06–2.21 (3H, m), 2.77–2.96 (3H, m), 6.68 (1H, d, J=7.5Hz), 6.81 (2H, d, J=8.5Hz), 7.07 (2H, d, J=8.5Hz), 7.12–7.37 (7H, m), 7.43–7.62 (2H, m), 7.83 (1H, m), 8.10 (1H, m)

87) 1-Ethoxycarbonylmethyl-5-{3-methyl-4-[2-(4methylphenyl)benzoylamino] benzoyl}-1,3,4,5-tetrahydro-1,5-benzodiazepin-2(2H)-one NMR (CDCl₃, δ): 1.33 (3H, t, J=7.5Hz), 1.43 (3H, s), 2.35 (3H, s), 2.53–2.88 (2H, m), 3.82 (1H, m), 4.15–4.34 (3H, m), 4.70 (1H, m), 4.82 (1H, d, J=17Hz), 6.70–6.85 (3H, m), 6.97 (1H, m), 7.11–7.55 (9H, m), 7.83 (1H, dd, J=1.5, 7.5Hz), 8.02 (1H, d, J=7.5Hz)

88) 7-Chloro-5-ethoxycarbonylmethyl-1-{4-[2-(4methylphenyl)benzoylamino] benzoyl}-2,3,4,5-tetrahydro-1H-1-benzazepine NMR (CDCl₃, δ): 1.27 (3H, t, J=7.5Hz), 2.33 (3H, s), 2.71 (1H, dd, J=6, 17.5Hz), 9.91 (1H, dd, J=6, 17.5Hz), 4.19 (1H, q, J=7.5Hz), 1.3–4.5 (7H, m), 6.53 (1H, d, J=7.5Hz), 6.86–6.95 (4H, m), 7.07–7.56 (10H, m), 7.84 (1H, d, J=7.5Hz)

89) 5-Ethoxycarbonylmethyl-1-{4-[2-(4-methylphenyl)benzoylamino] benzoyl}-2,3,4,5-tetrahydro-1H-1benzazepine NMR (CDCl₃, δ): 1.25 (3H, t, J=7.5Hz), 1.37 (1H, m), 1.78–2.09 (2H, m), 2.35 (3H, s), 2.64–3.00 (3H, m), 3.13 (1H, m), 3.51–3.79 (1H, m), 4.17 (2H, m), 4.51 (1H, m), 6.60 (1H, d, J=7.5Hz), 6.84–6.98 (4H, m), 7.10–7.55 (11H, m), 7.82 (1H, d, J=7.5Hz)

90) 5-Ethoxycarbonylmethyl-1-{4-[2-(2-methylphenyl)benzoylamino] benzoyl}-2,3,4,5-tetrahydro-1H-1benzazepine NMR (CDCl₃, δ): 1.27 (3H, t, J=7.5Hz), 2.08 (3×½H, s), 2.11 (3×½H, s), 2.67–3.01 (2H, m), 4.17 (2H, q, J=?.5Hz), 1.25–4.55 (7H, m), 6.59 (1H, d, J=7.5Hz), 6.81 (2H, d, J=8.5Hz), 6.91 (1H, m), 7.03–7.32 (10H, m), 7.44–7.59 (2H, m), 8.07 (1H, d, J=7.5Hz)

91) 5-Ethoxycarbonylmethyl-1-{ 4-[ 2-(4-methylphenyl)benzoylamino ]benzoyl} -2,3-dihydro-1H-1-benzazepine NMR (CDCl₃, δ): 1.23 (3H, t, J=7.5Hz), 2.32 (3H, s), 2.37 (1H, m), 2.60 (1H, m), 3.40 (1H, d, J=17.5Hz), 3.46 (1H, m), 3.75 (1H, d, J=17.5Hz), 4.14 (2H, m), 4.75 (1H, m), 6.22 (1H, t, J=5Hz), 6.64 (1H, d, J=7.5Hz), 6.84–6.97 (3H, m), 7.10–7.57 (12H, m), 7.81 (1H, dd, J=1.5, 7.5Hz)

92) 2-Dimethylamino-5-{4-[2-(4-methylphenyl)benzoylamino] benzoyl}-3,4-dihydro-5H-1,5-benzodiazepine NMR (CDCl₃, δ): 2.36 (3H, s), 2.57–2.69 (2H, m), 3.16 (6H, s), 3.85 (1H, dd, J=6, 16Hz), 4.67 (1H, dt, J=6, 16Hz), 6.55 (1H, d, J=7.5Hz), 6.64 (1H, t, J=7.5Hz), 6.86–6.93 (3H, m), 6.53 (1H, d, J=7.5Hz), 7.60–7.68 (5H, m), 7.29 (2H, d, J=8.5Hz), 7.39 (1H, t, J=7.5Hz), 7.05 (1H, d, J=7.5Hz), 7.52 (1H, t, J=7.5Hz), 7.84 (1H, d, J=7.5Hz)

93) 5-{ 4-[ 2-(4-Methylphenyl)benzoylamino]benzoyl }-2-(4-methyl-1-piperazinyl)-3,4-dihydro-5H-1,5benzodiazepine NMR (CDCl₃, δ): 2.32 (3H, s), 2.36 (3H, s), 2.49 (4H, m), 2.69 (2H, m), 3.54–3.90 (5H, m), 4.66 (1H, m), 6.56 (1H, d, J=7.5Hz), 6.67 (1H, d, J=7.5Hz), 6.85–7.51 (12H, m), 7.84 (1H, d, J=7.5Hz)

94) 1-{4-[1-(4-Methylphenyl)-2-naphthoylamino]benzoyl} -1,2,3,4-tetrahydroquinoline NMR (CDCl₃, δ): 2.03 (2H, tt, J=7, 7Hz), 2.44 (3H, s), 2.83 (2H, t, J=7Hz), 3.86 (2H, t, J=7Hz), 6.66 (1H, d, J=8Hz), 6.86 (1H, dd, J=8, 8Hz), 6.93–7.07 (3H, m), 7.10–7.28 (4H, m), 7.35 (4H, s), 7.44 (1H, dd, J=8, 8Hz), 7.56 (1H, dd, J=8, 8Hz), 7.66 (1H, d, J=8Hz), 7.84–8.02 (3H, m)

95) 2,3-Dimethyl-1-{4-[2-(4-methylphenyl)benzoyl] -aminobenzoyl } indoline

NMR (CDCl₃, δ): 1.05 (3H, d, J=6.5Hz), 1.09 (3H, d, J=6.5Hz), 2.38 (3H, s), 3.58 (1H, dq, J=6.5, 6.5Hz), 4.72 (1H, dq, J=6.5, 6.5Hz), 6.97–7.59 (16H, m), 7.99 (1H, dd, J=1.5, 7.5Hz)

96) 5-Dimethylamino-1-{ 6-[ 2-(4-methylphenyl) benzoyl ] aminonicotinoyl }-2,3,4,5-tetrahydro-1H-benzazepine NMR (CDCl₃, δ): 1.30–3.00 (6H, m), 2.08 (3H, s), 2.30 (3H, s), 2.37 (3H, s), 4.06 (1H, m), 6.56 (1H, d, J=8Hz), 6.95–8.20 (16H, m)

97) 1-Methoxycarbonylmethyl-5-{ 4-[ 2-(4-methylphenyl)benzoylamino] benzoyl}-1,3,4,5-tetrahydro-1,5-benzodiazepin-2(2H)-one NMR (DMSO-d₆, δ): 2.2 8 (3H, s), 2.40–2.75 (2H, m), 3.68 (3H, s), 3.72 (1H, m), 4.48 (1H, m), 4.51 (1H, d, J=17.1Hz), 4.76 (1H, d, J=17.1Hz), 6.80–7.40 (16H, m), 10.3 (1H, s)

Example 3

To a solution of 2-(1-pyrrolyl)benzoic acid (206 mg), diphenyl chlorophosphate (325 mg), 1-(4-aminobenzoyl}-1,2,3,4-tetrahydroquinoline (277 mg) in tetrahydrofuran (10 ml) was added triethylamine (333 mg) at 0° C. The resulting mixture was allowed to warm to ambient temperature where it was maintained for 5 hours. The solvent was evaporated and diluted with ethyl acetate and washed with water, saturated sodium bicarbonate aqueous solution and brine. The organic layer was dried over sodium sulfate and concentrated to give 1-{4-[2-(1-pyrrolyl)benzoylamino] benzoyl}-1,2,3,4tetrahydroquinoline (280 mg).

NMR (DMSO-d₆, δ): 1.94 (2H, tt, J=7, 7Hz), 2.81 (2H, t, J=7Hz), 3.74 (2H, t, J=7Hz), 6.17 (2H, dd, J=2, 2Hz), 6.77 (1H, d, J=8Hz), 6.86–7.10 (4H, m), 7.21 (1H, d, J=8Hz), 7.28 (2H, d, J=8Hz), 7.40–7.70 (6H, m)

Example 4

To a solution of 1-(carboxymethyl)-4-{4-[2-(4methylphenyl)benzoylamino] benzoyl}-1,2,3,4-tetrahydro -quinoxalin-2-one (100 mg) in dichloromethane (10 ml) were added triethylamine (0.030 ml) and diphenylphosphinic chloride (54.7 mg) and the solution was stirred at ambient temperature for 30 minutes. Triethylamine (0.030 ml) and 1-methylpiperazine (0.032 ml) were added to the solution and the mixture was stirred at ambient temperature for 3 hours. The solution was washed with water and brine and dried over magnesium sulfate. The organic solution was evaporated in vacuo and the residue was subjected to a silica gel column (10 g, 2% methanol in chloroform). The object fractions were evaporated in vacuo and the residue was solidified with diethyl ether to give 1-[(4-methyl-1-piperazinyl)carbonylmethyl]-4-{4-[2-(4methylphenyl)benzoylamino] benzoyl}-1,2,3,4-tetrahydro -quinoxalin-2-one (77.0 mg) as a white powder.

NMR (CDCl₃, δ): 2.32 (3H, s), 2.34 (3H, s), 2.43 (2H, t, J=5Hz), 2.51 (2H, t, J=5Hz), 3.58–3.70 (4H, m), 4.62 (2H, s), 4.77 (2H, s), 6.68–6.88 (2H, m), 7.00–7.58 (14H, m), 7.86 (1H, dd, J=1, 8Hz)

Example 5

A mixture of 5-{4-[2-(2-methylphenyl)benzoylamino] benzoyl} -1-(4-phthaloylaminobutyl)-1,3,4,5-tetrahydro-1,5

-benzodiazepin-2(2H)-one (800 mg) and hydrazin monohydrate (296 mg) in ethanol (20 ml) was stirred at ambient temperature for 6 hours. After removal of insoluble material by filtration, the filtrate was evaporated in vacuo and the residue was subjected to a silica gel column (20 g, 2% methanol in chloroform) to give 1-(4-aminobutyl)-5-{4-[2-(2-methylphenyl)benzoylamino] -benzoyl}-1,3,4,5-tetrahydro-1,5-benzodiazepin-2(2H)-one (434 mg) as a pale yellow amorphous.

NMR (CDCl$_3$, δ): 1.33–1.59 (4H, m), 1.67–1.85 (2H, m), 2.06 and 2.09 (total 3H, s), 2.44–2.77 (4H, m), 3.71–3.87 (2H, m), 4.00 (1H, m), 4.65 (1H, m), 6.69 (1H, br), 6.81–6.95 (3H, m), 7.03–7.36 (9H, m), 7.40–7.60 (2H, m), 8.07 (1H, dd, J=8, 1Hz)

Example 6

The following compounds were obtained according to a similar manner to that of Example 5.

1) 1-(3-Aminopropyl)-4-{4 -[2-(4-methylphenyl)benzoylamino] benzoyl}-1,2,3,4 -tetrahydroquinoxalin-2-one NMR (CDCl$_3$+ CD$_3$OD, δ): 2.00 (2H, tt, J=7.5, 7.5Hz), 2.35 (3H, s), 2.86 (2H, t, J=7.5Hz), 3.41 (3H, s), 4.1 2 (2H, t, J=7.5Hz), 4.55 (2H, s), 6.72–6.90 (2H, m), 7.17–7.58 (12H, m), 7.73–7.84 (2H, m), 8.21 (1H, m)

2) 1-{[4-(3-Aminopropyl)-1-piperazinyl]carbonylmethyl} -5-{4-[2-(4-methylphenyl)benzoylamino]benzoyl} -1,3,4,5-tetrahydro-1,5-benzodiazepin-2(2H)-one Rf: 0.13 (10% methanol in chloroform)
FAB-MASS (m/z): 659 (M$^+$1)

3) 1-(6-Aminohexyl)-5-{4-[2-(4-methylphenyl)benzoylamino] benzoyl}-1,3,4,5-tetrahydro-1,5 -benzodiazepin-2(2H)-one This product was used for next step without purification.

Example 7

A solution of 1-[4-[2-(2-azidomethylphenyl)benzoylamino] benzoyl}-1,2,3,4-tetrahydroquinoline (535 mg) in a mixture of methanol (35 ml) and dioxane (4 ml) containing catalytic palladium on carbon (60 mg) was stirred under atmospheric pressure of hydrogen at ambient temperature. After 3 hours, the reaction mixture was filtered through a bed of celite, and then concentrated to give 1-{4-[2-(2-aminomethylphenyl)benzoylamino]benzoyl} -1,2,3,4-tetrahydroquinoline (395 mg) which was purified by recrystallization from a mixture of ethyl acetate and diethyl ether.

NMR (CDCl$_3$, δ): 1.68 (2H, br s), 2.01 (2H, tt, J=7, 7Hz), 2.80 (2H, t, J=7Hz), 3.77 (1H, d, J=13Hz), 3.85 (2H, t, J=7Hz), 4.04 (1H, d, J=13Hz), 6.71 (1H, d, J=8Hz), 6.87 (1H, dd, J=8, 8Hz), 6.98 (1H, dd, J=8, 8Hz), 7.05–7.37 (11H, m), 7.40–7.59 (2H, m), 7.73–7.87 (1H, m)

Example 8

To a solution of 1-{4-[2-(2-aminomethylphenyl)benzoylamino] benzoyl}-1,2,3,4-tetrahydroquinoline (100 mg) in dichloromethane (5 ml) were added pyridine (45 mg), acetic anhydride (23 N1) and catalytic amount of 4-dimethylaminopyridine. The reaction mixture was stirred for 1 hour at ambient temperature and washed with water and brine and the organic phase was dried over magnesium sulfate. The solvent was evaporated in vacuo and the residue was triturated with diethyl ether to give 1-{4-[2-(2-acetylaminomethyl)benzoylamino]benzoyl} -1,2,3,4-tetrahydroquinoline (90 mg).

NMR (CDCl$_3$, δ): 1.81 (3H, s), 2.02 (2H, tt, J=7, 7Hz), 2.83 (2H, t, J=7Hz), 3.86 (2H, dt, J=3, 7Hz), 4.20 (1H, dd, J=15, 6 Hz), 4.32 (1H, dd, J=15, 6 Hz), 6.55–6.76 (2H, m), 6.87 (1H, dd, J=8, 8Hz), 6.98 (1H, dd, J=8, 8Hz), 7.06–7.65 (12H, m), 7.73–7.86 (1H, m), 8.30 (1H, br s)

Example 9

To a solution of 1-{4-[2-(2-aminomethylphenyl)benzoylamino] benzoyl}-1,2,3,4-tetrahydroquinoline (180 mg), 37% formaldehyde (75 μl) and methanol (5 ml) containing acetic acid (0.1 ml) was added sodium cyanoborohydride (54 mg). The resulting mixture was stirred for 5 hours at ambient temperature and added sodium bicarbonate aqueous solution. The solution was evaporated and the residue was extracted with ethyl acetate and washed with brine, dried over sodium sulfate. The solvent was evaporated in vacuo and triturated with diethyl ether to give 1-{4-[2-(2-dimethylaminomethylphenyl)benzoylamino] benzoyl}-1,2,3,4-tetrahydroquinoline (90 mg).

NMR (CDCl$_3$, δ): 1.96 (6H, s), 2.00 (2H, tt, J=7, 7Hz), 2.81 (2H, t, J=7Hz), 2.85 (1H, d, J=13Hz), 3.84 (2H, t, J=7Hz), 3.88 (1H, d, J=13Hz), 6.75 (1H, d, J=8Hz), 6.82–7.05 (2H, m), 7.73–7.87 (1H, m), 10.10 (1H, br s)

Example 10

The following compounds were obtained according to a similar manner to that of Example 9.

1) 1-(4-Dimethylaminobutyl)-5-{4-[2-(2-methylphenyl)benzoylamino] benzoyl}-1,3,4,5-tetrahydro-1,5 -benzodiazepin-2(2H)-one NMR (CDCl$_3$, δ): 1.59 (2H, m), 1.68 (2H, m), 2.05 and 2.07 (total 3H, s), 2.28 (6H, s), 2.38 (2H, t, J=7Hz), 2.48–2.70 (2H, m), 3.72–4.03 (3H, m), 4.63 (1H, m), 6.71 (1H, br), 6.86 (2H, d, J=8.5Hz), 6.93 (1H, m), 7.05–7.16 (3H, m), 7.21–7.38 (7H, m), 7.46–7.59 (2H, m), 8.07 (1H, d, J=8Hz)

2) 1-(3-Dimethylaminopropyl-4-{4-[2-(4-methylphenyl)benzoylamino] benzoyl}-1,2,3,4-tetrahydroquinoxalin -2-one NMR (CDCl$_3$, δ): 1.86 (2H, tt, J=7.5, 7.5Hz), 2.22 (6H, s), 2.36 (3H, s), 2.39 (2H, t, J=7.5Hz), 4.05 (2H, t, J=7.5Hz), 4.54 (2H, s), 6.69–6.87 (2H, m), 7.01–7.57 (14H, m), 7.86 (1H, d, J=8Hz)

3) 1-(6-Dimethylaminohexyl)-5-{4-[2-(4-methylphenyl)benzoylamino] benzoyl}-1,3,4,5-tetrahydro-1,5 -benzodiazepin-2(2H)-one NMR (CDCl$_3$, δ): 1.29–1.55 (6H, m), 1.60–1.81 (2H, m), 2.20–2.37 (2H, m), 2.21 (6H, s), 2.35 (3H, s), 2.49–2.74 (2H, m), 3.71–3.86 (2H, m), 4.01 (1H, m), 4.65 (1H, m), 6.22 (1H, d, J=7.5Hz), 6.91–7.03 (3H, m), 7.08–7.57 (12H, m), 7.82 (1H, dd, J=1.5, 7.5Hz)

Example 11

To a solution of 1-{4-[4-methoxy-2-(4-methylphenyl)benzoylamino] benzoyl}-1,2,3,4-tetrahydroquinoline (380 mg) in dichloromethane (15 ml) at −78° C. was added a solution of 1.0M boron tribromide in dichloromethane (2.4 ml). The resulting solution was allowed to warm to ambient temperature where it was maintained for 12 hours. The mixture was cooled to 0° C., and added water. The organic layer was washed with saturated sodium bicarbonate aqueous solution and filtered through a bed of celite, and concentrated. The residue was triturated with diethyl ether to give 1-{4-[4-hydroxy-2-(4-methylphenyl)benzoylamino]benzoyl}-1,2,3,4-tetrahydroquinoline (30 mg).

NMR (CDCl₃, δ): 2.02 (2H, tt, J=7, 7Hz), 2.36 (3H, s), 2.82 (2H, t, J=7Hz), 3.88 (2H, t, J=7Hz), 6.49 (1H, br s), 6.68 (1H, d, J=8Hz), 6.77–6.93 (3H, m), 6.92–7.06 (4H, m), 7.09–7.35 (7H, m), 7.78 (1H, d, J=8Hz)

Example 12

The mixture of 1-ethoxycarbonylmethyl-5-{4-[2-(4-methylphenyl)benzoylamino] benzoyl}-1,3,4,5-tetrahydro-1,5-benzodiazepin-2(2H)-one (240 mg), 1N sodium hydroxide aqueous solution (2 ml) and ethanol (5 ml) was stirred for 1 hour at ambient temperature. The reaction was quenched with 1N hydrochloric acid (2 ml) and ethanol was removed. The residue was diluted with ethyl acetate and the solution was washed with brine, and the solution was dried over magnesium sulfate. Filtering and the removal of solvents afforded a crude product. The crude product was triturated with a mixture of diisopropyl ether and diethyl ether (1:1) to give 1-carboxymethyl-5-{4-[2-(4methylphenyl)benzoylamino] benzoyl}-1,3,4,5-tetrahydro-1,5 -benzodiazepin-2(2H)-one (217 mg) as a white powder.

mp: 175°–183° C.

NMR (CDCl₃, δ): 2.36 (3H, s), 2.52–2.82 (2H, m), 3.82 (1H, dd, J=6, 13Hz), 4.42 (1H, d, J=17Hz), 4.55–4.86 (2H, m), 6.65–6.80 (1H, m), 6.90–7.58 (14H, m), 7.75 (1H, d, J=8Hz)

Example 13

The following compounds were obtained according to a similar manner to that of Example 12.

1) 1-Carboxymethyl-5-{ 4-[ 2-(2-methylphenyl) benzoylamino ] benzoyl }-1,3,4,5-tetrahydro-1,5-benzodiazepin -2 (2H)-one mp: 200°–205° C.

NMR (CDCl₃, δ): 2.10 (3H, s), 2.58–2.85 (2H, m), 3.80 (1H, dd, J=5, 11Hz), 4.38 (1H, d, J=17Hz), 4.60–4.90 (3H, m), 6.65–6.75 (1H, br s), 6.80–7.60 (14H, m), 8.00 (1H, d, J=8Hz)

2) 1-Carboxymethyl-5-{4-[2-(2,4-dimethylphenyl)benzoylamino] benzoyl}-1,3,4,5-tetrahydro-1,5 -benzodiazepin-2(2H)-one NMR (CDCl₃, δ): 2.00 and 2.04 (total 3H, s), 2.35 (3H, s), 2.54–2.86 (2H, m), 3.80 (1H, m), 4.32 (1H, d, J=17.5Hz), 4.68 (1H, m), 4.82 (1H, d, J=17.5Hz), 6.28 (2H, br), 6.72 (1H, m), 6.87 (2H, d, J=8.5Hz), 6.95 (1H, m), 7.02–7.39 (8H, m), 7.42–7.58 (2H, m), 7.99 (1H, d, J=8Hz)

3) 1-(2-Carboxyethyl)-5-{4-[2-(2-methylphenyl)benzoylamino] benzoyl}-1,3,4,5-tetrahydro-1,5 -benzodiazepin-2(2H)-one NMR (CDCl₃, δ): 2.08 (3H, br s), 2.42–2.76 (2H, m), 2.78–3.01 (2H, m), 3.70–4.83 (4H, m), 6.63–7.68 (16H, m), 8.05 (1H, br d, J=9Hz)

4) 1-(3-Carboxypropyl)-5-{4-[2-(2-methylphenyl)benzoylamino] benzoyl}-1,3,4,5-tetrahydro-1,5 -benzodiazepin-2(2H)-one NMR (CDCl₃, δ): 1.68–2.80 (9H, m), 3.60–4.16 (3H, m), 4.45–4.80 (1H, m), 6.60–7.65 (16H, m), 8.06 (1H, br d, J=9Hz)

5) 1-(1-Carboxyethyl)-5-{4-[2-(2-methylphenyl)benzoylamino] benzoyl}-1,3,4,5-tetrahydro-1,5 -benzodiazepin-2(2H)-one NMR (CDCl₃, δ): 1.56–1.80 (3H, m), 1.96–2.15 (3H, m), 2.51–2.78 (2H, m), 3.65–5.04 (3H, m), 6.00–7.68 (16H, m), 7.95–8.15 (1H, m)

6) 1-Carboxymethyl-7,8-dimethyl-5-{4-[2-(4methylphenyl)benzoylamino] benzoyl} -1,3,4,5 -tetrahydro-1,5-benzodiazepin-2(2H)-one NMR (CDCl₃, δ): 1.99 (3H, s), 2. 20 (3H, s), 2.34 (3H, s), 2.48–2.79 (2H, m), 3 .55–3.80 (1H, m), 4.39 (1H, d, J=1, 8Hz), 4.52–4. 75 (1H, m), 4.68 (1H, d, J=1, 8Hz), 6.43–6.52 (1H, br), 7.01 (3H, s), 7.08–7.57 (10H, m), 7.78 (1H, d, J=8Hz)

7) 1-Carboxymethyl-7-methyl-5-{ 4-[ 2-(4-methylphenyl) benzoylamino ]benzoyl} -1,3,4,5-tetrahydro-1,5 -benzodiazepin-2 (2H )-one NMR (CDCl₃, δ): 2.10 (3H, s), 2.35 (3H, s), 2.50–2.75 (2H, m), 3.15–3.34 (1H, br), 3.78 (1H, dd, J=5, 13Hz), 4.38 (1H, d, J=16Hz), 4.54–4.72 (1H, m), 4.70 (1H, d, J=16Hz), 6.49–6.58 (1H, br s), 6.95–7.32 (10H, m), 7.36–7.56 (3H, m), 7.77 (1H, d, J=8Hz)

8) 1-Carboxymethyl-8-chloro-5-{4-[2-(4-methylphenyl)benzoylamino] benzoyl}-1,3,4,5-tetrahydro-1,5 -benzodiazepin-2 (2H )-one NMR (CDCl₃, δ): 2.39 (3H, s), 2.55–2.76 (2H, m), 3.79 (1H, dd, J=5, 13Hz), 4.42 (1H, d, J=17Hz), 4.52–4.73 (1H, m), 4.67 (1H, d, J=17Hz), 6.63–6.73 (1H, m), 6.92–7.33 (10H, m), 7.35–7.55 (3H, m), 7.78 (1H, d, J=7Hz)

9) 1-Carboxymethyl-8-chloro-5-{3-methyl-4-[2-(4methylphenyl)benzoylamino] benzoyl}-1,3,4,5 -tetrahydro-1,5-benzodiazepin-2(2H)-one Rf: 0.75 (chloroform:methanol:acetic acid = 8:2:1)

10) 1-Carboxymethyl-8-chloro-5-{3-methoxy-4-[2-(4methylphenyl)benzoylamino] benzoyl}-1,3,4,5 -tetrahydro-1,5-benzodiazepin-2(2H)-one Rf: 0.06 (10% methanol in chloroform)

11) 1- Carboxymethyl-5 -{ 3 -methoxy-4 -[ 2 -(4 -methylphenyl) benzoylamino ]benzoyl }-8-methyl-1,3,4,5-tetrahydro -1,5-benzodiazepin-2 (2H)-one NMR (CDCl₃, δ): 2.32 (3H, s), 2.33 (3H, s), 2.55–2.80 (2H, m), 3.47 (3H, s), 3.80 (1H, dd, J=5, 13Hz), 4.29 (1H, d, J=1, 8Hz), 4.58–4.78 (1H, m), 4.82 (1H, d, J=1, 8Hz), 6.54–6.68 (2H, m), 6.79 (1H, d, J=8Hz), 6.90 (1H, s), 7.07 (1H, s), 7.15 (2H, d, J=8Hz), 7.25–7.59 (4H, m), 7.74–7.83 (2H, m), 8.18 (1H, d, J=9Hz)

12) 1-Carboxymethyl-5-{4-[2-(2,4-dimethylphenyl)benzoylamino] -3-methoxybenzoyl-8-methyl-1,3,4,5 -tetrahydro-1,5-benzodiazepin-2(2H)-one Rf: 0.09 (10% methanol in chloroform) 0.89 (chloroform:methanol:acetic acid = 8:2:1)

13) 1-Carboxymethyl-8-methyl-5-{4-[2-(4-methylphenyl)benzoylamino] benzoyl}-1,3,4,5 -tetrahydro-1,5 -benzodiazepin-2(2H)-one NMR (CDCl₃, δ): 2.36 (3H, s), 2.39 (3H, s), 2.55–2.86 (2H, m), 3.70–3.85 (1H, m), 4.40 (1H, d, J=17Hz), 4.56–4.76 (1H, m), 4.73 (1H, d, J=17Hz), 6.55–6.67 (1H, m), 6.74–6.82 (1H, m), 6.95–7.54 (12H, m), 7.79 (1H, d, J=7Hz)

14) 1-Carboxymethyl-8-methyl-5-{3-methyl-4-[2-(4methylphenyl)benzoylamino] benzoyl}-1,3,4,5 -tetrahydro-1,5-benzodiazepin-2(2H)-one Rf: 0.06 (10% methanol in chloroform) 0.79 (chloroform:methanol:acetic acid = 8:2:1)

15) 1-Carboxymethyl-8-methoxy-5-{4-[2-(4-methylphenyl)benzoylamino] benzoyl}-1,3,4,5-tetrahydro-1,5 -benzodiazepin-2(2H)-one NMR (CDCl₃, δ): 2.36 (3H, s), 2.53–2.79 (2H, m), 3.05–3.25 (1H, m), 3.68–3.84 (1H, m), 3.78 (3H, s), 16) 1-Carboxymethyl-5-{3-chloro-4-[2-(2-methylphenyl)benzoylamino] benzoyl}-1,3,4,5-tetrahydro-1,5 -benzodiazepin-2(2H)-one NMR (CDCl$_3$, δ): 2.13 and 2.15 (total 3H, s), 2.56–2.90 (2H, m), 3.75–3.92 (1H, m), 4.32 (1H, d, J=17Hz), 4.69 (1H, dt, J=5, 13Hz), 4.87 (1H, d, J=17Hz), 6.67–6.84 (1H, m), 6.86–7.12 (2H, m), 7.16–7.40 (7H, m), 7.42–7.63 (3H, m), 7.68 (1H, br s), 7.94 (1H, d, J=8Hz), 8.10–8.45 (2H, m)

17) 1-Carboxymethyl-5-{3-chloro-4-[2-(2,4-dimethylphenyl)benzoylamino] benzoyl}-1,3,4,5-tetrahydro-1,5 -benzodiazepin-2(2H)-one NMR (CDCl$_3$, δ): 2.07 and 2.15 (total 3H, s), 2.32 (3H, s), 2.55–2.90 (2H, m), 3.75–3.92 (1H, m), 4.32 (1H, d, J=17Hz), 4.58–4.80 (1H, m), 4.88 (1H, d, J=17Hz), 6.68–6.85 (1H, m), 6.86–7.48 (8H, m), 7.50–7.62 (2H, m), 7.74 (1H, br s), 7.88–8.00 (2H, m), 8.20–8.36 (1H, m)

18) 1-Carboxymethyl-5-{2-chloro-4-[2-(2,4dimethylphenyl)benzoylamino] benzoyl}-1,3,4,5 -tetrahydro-1,5-benzodiazepin-2(2H)-one NMR (CDCl$_3$, δ): 1.99 and 2.05 (total 3H, s), 2.40 (3H, s), 2.52–2.88 (2H, m), 3.69–3.88 (1H, m), 3.97–4.16 (1H, m), 4.85 (1H, d, J=16Hz), 4.77–4.98 (1H, m), 6.39–7.68 (15H, m), 7.96–8.12 (1H, m)

19) 1-Carboxymethyl-5-{4-[2-(2-methylphenyl)benzoylamino] -3-nitrobenzoyl}-1,3,4,5 -benzodiazepin-2(2H)-one NMR (CDCl$_3$, δ): 2.17 and 2.22 (total 3H, s), 2.56–2.92 (2H, m), 3.77–3.95 (1H, m), 4.46 (1H, d, J=16Hz), 4.62–4.85 (1H, m), 4.82 (1H, d, J=16Hz), 6.65–6.82 (1H, m), 6.93–7.68 (11H, m), 7.74–7.90 (2H, m), 8.60 (1H, d, J=9Hz), 10.03 (1H, br s)

20) 1-Carboxymethyl-5-{4-[2-(2,4-dimethylphenyl)benzoylamino] -2-nitrobenzoyl}-1,3,4,5 -benzodiazepin-2(2H)-one NMR (CDCl$_3$, δ): 2.00 and 2.02 (total 3H, s), 2.52–2.86 (2H, m), 3.72–3.90 (1H, m), 4.13–4.30 (1H, m), 4.80 (1H, d, J=16Hz), 4.76–5.00 (1H, m), 6.85–7.63 (15H, m), 8.01 (1H, d, J=9Hz)

21) 1-Carboxymethyl-5-{3-methoxy-4-[2-(4-methylphenyl)benzoylamino] benzoyl}-1,3,4,5-tetrahydro-1,5 -benzodiazepin-2(2H)-one NMR (CDCl$_3$, δ): 2.34 (3H, s), 2.55–2.91 (2H, m), 3.42 (3H, s), 3.76–3.95 (1H, m), 4.30 (1H, d, J=16Hz), 4.60–4.82 (1H, m), 4.84 (1H, d, J=16Hz), 6.58–7.08 (3H, m), 7.10–7.60 (10H, m), 7.71–7.87 (2H, m), 8.19 (1H, d, J=9Hz)

22) 1-Carboxymethyl-5-{ 3-methoxy-4-[ 2-(2-methylphenyl) benzoylamino] benzoyl} -1,3,4,5-tetrahydro-1,5 -benzodiazepin-2 (2H)-one NMR (CDCl$_3$, δ): 2.07 and 2.12 (total 3H, s), 2.53–2.88 (2H, m), 3.47 (3H, s), 3.75–3.94 (1H, m), 4.27 (1H, d, J=16Hz), 4.59–4.80 (1H, m), 4.84 (1H, d, J=1, 6Hz), 6.50–7.06 (4H, m), 7.12–7.67 (10H, m), 7.84 (1H, br s), 7.96 (1H, d, J=9Hz), 8.20 (1H, d, J=9Hz)

23) 1-Carboxymethyl-5-{3-methoxy-4-[2-(2,4dimethylphenyl)benzoylamino] benzoyl}-1,3,4,5 -tetrahydro-1,5-benzodiazepin-2(2H)-one NMR (CDCl$_3$, δ): 2.04 and 2.09 (total 3H, s), 2.33 (3H, s), 2.56–2.92 (2H, m), 3.47 (3H, s), 3.76–3.94 (1H, m), 4.28 (1H, d, J=16Hz), 4.60–4.84 (1H, m), 4.86 (1H, d, J=16Hz), 6.51–6.70 (1H, m), 6.71–6.94 (2H, m), 6.94–7.40 (6H, m), 7.40–7.65 (3H, m), 7.90 (1H, br s), 7.97 (1H, d, J=9Hz), 8.22 (1H, d, J=9Hz)

24) 1-Carboxymethyl-5-{4-[2-(2,6-dimethylphenyl)benzoylamino] benzoyl}-1,3,4,5-tetrahydro-1,5 -benzodiazepin-2(2H)-one Rf: 0.08 (10% methanol in chloroform) 0.75 (chloroform:methanol:acetic acid = 8:1:1)

25) 5-Carboxymethoxyimino-1-{4-[2-(4-methylphenyl)benzoylamino] benzoyl}-2,3,4,5-tetrahydro-1H-1benzazepine NMR (CDCl$_3$, δ): 1.56–1.84 (1H, br s), 1.89–2.15 (1H, br s), 2.34 (3H, s), 2.71–2.98 (2H, m), 3.12–3.45 (1H, br s), 4.26–5.11 (3H, m), 6.65 (1H, d, J=8Hz), 6.80–7.58 (15H, m), 7.73 (1H, d, J=8Hz)

26) 1-Carboxymethyl-5-{ 3 -hydroxy-4-[ 2-(4-methylphenyl) benzoylamino] benzoyl}-1,3,4,5-tetrahydro-1,5 -benzodiazepin-2 (2H )-one NMR (CDCl$_3$, δ): 2.09 (3H, s), 2.33 (2H, s), 2.43–2.60 (1H, m), 2.62–2.78 (1H, m), 3.69–3.84 (1H, m), 4.34–4.49 (1H, m), 6.52–7.81 (16H, m)

27) 1-Carboxymethyl-4,4-dimethyl-5-{4-[2-(4methylphenyl)benzoylamino] benzoyl}-1,3,4,5 -tetrahydro-1,5-benzodiazepin-2(2H)-one Rf: 0.06 (10% methanol in chloroform)

28) 1-Carboxymethyl-4-methyl-5-{4-[2-(4-methylphenyl)benzoylamino] benzoyl}-1,3,4,5-tetrahydro-1,5 -benzodiazepin-2(2H)-one Rf: 0.09 (10% methanol in chloroform)

29) 1-[(4-Carboxymethyl-1-piperazinyl)carbonylmethyl] -5-{4-[2-(4-methylphenyl)benzoylamino]benzoyl} -1,3,4,5-tetrahydro-1,5-benzodiazepin-2(2H)-one NMR (DMSO-d$_6$, δ): 2.28 (3H, s), 2.43–2.63 (6H, m), 3.20–3.60 (7H, m), 3.70–3.78 (1H, m), 4.45 (1H, d, J=17Hz), 5.00 (1H, d, J=17Hz), 6.80 (1H, d, J=6Hz), 6.96–7.02 (1H, m), 7.12 (4H, d, J=8Hz), 7.26 (4H, d, J=8Hz), 7.35–7.57 (6H, m)

30) 1-Carboxymethyl-5-{4-[2-(4-methylphenyl)benzoylamino] benzoyl}-8-trifluoromethyl-1,3,4,5 -tetrahydro-1,5-benzodiazepin-2(2H)-one Rf: 0.10 (10% methanol in chloroform)

31) 1-Carboxymethyl-5-{2-methoxy-4-[2-(4-methylphenyl)benzoylamino] benzoyl}-1,3,4,5-tetrahydro-1,5 -benzodiazepin-2(2H)-one NMR (CDCl$_3$, δ): 2.30 (3×¾H, s), 2.34 (3×¼H, s), 2.53–2.75 (2H, m), 3.70 (3H, s), 3.70–4.40 (2H, m), 4.87 (2H, m), 6.19 (1H, d, J=7.5Hz), 6.72–7.02 (3H, m), 7.10–7.57 (11H, m), 7.78 (1H, d, J=7.5Hz)

32) 1-Carboxymethyl-5-{6-[2-(4-methylphenyl)benzoylamino] nicotinoyl}-1,3,4,5-tetrahydro-1,5 -benzodiazepin-2(2H)-one NMR (CDCl$_3$, δ): 2.29 (3H, s), 2.52–2.82 (2H, m), 3.75–3.89 (1H, m), 4.41–4.78 (3H, m), 6.74 (1H, d, J=7.5Hz), 7.01 (1H, dt, J=7.5, 1.5Hz), 7.12 (2H, d, J=8.5Hz), 7.18–7.51 (7H, m), 7.57–7.18 (2H, m), 7.90 (1H, d, J=1.5Hz), 8.09 (1H, d, J=7.5Hz), 8.82 (1H, br)

33) 1-Carboxymethyl-5-{ 4-[ 2-(3-methylphenyl)benzoylamino ]benzoyl} -1,3,4,5 -tetrahydro-1,5 -benzodiazepin-2 (2H )-one NMR (CDCl$_3$, δ): 2.27 (3H, s), 2.50–2.82 (2H, m), 3.80 (1H, dd, J=6, 12.5Hz), 4.38 (1H, d, J=17.7Hz), 4.53–4.81 (2H, m), 5.48 (1H, br), 6.71 (1H, d, J=7.5Hz), 6.96 (2H, d, J=8.5Hz), 7.03–7.29 (10H, m), 7.34–7.53 (3H, m), 7.87 (1H, d, J=7.5Hz)

34) 1-Carboxymethyl-7,8-dimethyl-5-{4-[2-(2,6dimethylphenyl)benzoylamino] benzoyl}-1,3,4,5 -tetrahydro-1,5-benzodiazepin-2(2H)-one NMR (CDCl$_3$, δ): 1.98 (3H, s), 2.01 (3H, s), 2.03 (3H, s), 2.20 (3H, s), 2.45–2.82 (2H, m), 3.72 (1H, m), 4.18 (1H, d, J=15Hz), 4.65 (1H, m), 4.72 (1H, d, J=15Hz), 6.85 (2H, d, J=8.5Hz), 6.98 (1H, s), 7.05–7.41 (7H, m), 7.48 (1H, s), 7.48–7.60 (2H, m), 8.21 (1H, dd, J=1.5, 7.5Hz)

35) 1-Carboxymethyl-5-{ 4-[ 2-(4-methylphenyl) benzoylamino] benzoyl} -2,3,4,5-tertrahydro-1H-1,5-benzodiazepine NMR (CDCl$_3$+ CD$_3$OD, δ): 1.95 (1H, m), 2.10 (1H, m), 2.34 (3H, s), 3.06–3.27 (2H, m), 3.65 (1H, m), 3.92 (1H, d, J=17.5Hz), 4.10 (1H, d, J=17.5Hz), 4.51 (1H, m), 6.51 (2H, m), 6.80 (1H, d, J=7.5Hz), 7.01–7.31 (10H, m), 7.39–7.55 (3H, m), 7.65 (1H, dd, J=1.5, 7.5Hz)

36) 1-Carboxymethyl-5-{4-[2-(2,6-dimethylphenyl)benzoylamino] benzoyl}-1,3,4,5-tetrahydro-1,5 -benzodiazepin-2(2H)-one NMR (CDCl$_3$, δ): 2.05 (3H, s), 2.20 (3H, s), 2.48–2.83 (2H, m), 3.71 (1H, m), 4.15 (1H, d, J=15Hz), 4.65 (1H, m), 4.74 (1H, d, J=15Hz), 6.86 (2H, d, J=8.5Hz), 6.96 (1H, s), 7.02–7.48 (7H, m), 7.51 (1H, s), 7.45–7.62 (2H, m), 8.24 (1H, dd, J=1.5, 7.5Hz)

37) 1-Carboxymethyl-5-{4-[N-2-(4-methylphenyl)benzoyl-N-methyl] aminobenzoyl}-1,3,4,5-tetrahydro-1,5 -benzodiazepin-2(2H)-one NMR (CDCl$_3$, δ): 2.39 (3H, s), 2.55–2.82 (2H, m), 3.10 (3H, s), 3.79 (1H, m), 4.28 (1H, d, J=17Hz), 4.66 (1H, m), 4.82 (1H, d, J= 17Hz), 6.01 (2H, d, J=8.5Hz), 6.63–6.85 (4H, m), 6.94–7.09 (4H, m), 7.20–7.34 (5H, m), 7.48 (1H, m)

38) 1-Carboxymethyl-5-{4-[2-(2-trifluoromethylphenyl)benzoylamino] benzoyl}-1,3,4,5-tetrahydro-1,5 -benzodiazepin-2(2H)-one NMR (CDCl$_3$, δ): 2.50–2.80 (2H, m), 3.76 (1H, m), 4.40 (1H, dd, J=4.5, 17.5Hz), 4.59 (1H, m), 4.70 (1H, d, J=17.5Hz), 5.74 (2H, br), 6.72 (1H, m), 6.96 (1H, m), 7.02–7.13 (3H, m), 7.20–7.34 (5H, m), 7.43–7.56 (4H, m), 7.64–7.73 (3H, m)

39) 1-Carboxymethyl-5-{4-[2-(2,4,6-trimethylphenyl) -benzoylamino]benzoyl}-1,3,4,5-tetrahydro-1,5 -benzodiazepin-2(2H)-one NMR (CDCl$_3$, δ): 1.94 (3H, s), 1.99 (3H, s), 2.37 (3H, s), 2.53–2.90 (2H, m), 3.80 (1H, m), 4.39 (1H, d, J=17Hz), 4.57–4.96 (2H, m), 6.72 (1H, d, J=7.5Hz), 6.87 (1H, d, J=8.5Hz), 6.92–7.17 (5H, m), 7.27 (1H, s), 7.29 (2H, d, J=8.5Hz), 7.32–7.60 (3H, m), 8.21 (1H, m)

40) 1-Carboxymethyl-5-{3-methyl-4-[2-(4-methylphenyl)benzoylamino] benzoyl}-1,3,4,5-tetrahydro-1,5 -benzodiazepin-2 (2H )-one NMR (CDCl$_3$, δ): 1.45 (3H, s), 2.37 (3H, s), 2.52–2.86 (2H, m), 3.82 (1H, m), 4.20 (1H, d, J=17Hz), 4.70 (1H, m), 4.83 (1H, d, J=17Hz), 6.69–5.85 (3H, m), 6.95 (1H, m), 7.09–7.56 (9H, m), 7.83 (1H, dd, J=1.5, 7.5Hz), 8.00 (1H, d, J=7.5Hz)

41) 5-Carboxymethyl-7-chloro-1-{4-[2-(4-methylphenyl)benzoylamino] benzoyl}-2,3,4,5-tetrahydro-1H-1benzazepine NMR (CDCl$_3$, δ): 2.33 (3H, s), 2.29 (1H, dd, J=6, 17.5Hz), 3.00 (1H, dd, J=6, 17.5Hz), 1.25–4.50 (7H, m), 6.53 (1H, d, J=7.5Hz), 6.87–7.01 (4H, m), 7.18–7.52 (10H, m), 7.74 (1H, d, J=7.5Hz)

42) 5-Carboxymethyl-1-{4-[2-(4-methylphenyl)benzoylamino] benzoyl}-2,3,4,5-tetrahydro-1H-1-benzazepine NMR (CDCl$_3$, δ): 1.35 (1H, m), 1.78–2.05 (2H, m), 2.35 (3H, s), 2.64–3.80 (5H, m), 4.51 (1H, m), 6.60 (1H, d, J=7.5Hz), 6.84–6.98 (4H, m), 7.10–7.55 (11H, m), 7.82 (1H, d, J=7.5Hz)

43) 5-Carboxymethyl-1-{4-[2-(2-methylphenyl)benzoyl -amino] benzoyl }-2,3,4,5-tetrahydro-1H-1-benzazepine NMR (CDCl$_3$, δ): 2.06 (3H, s), 2.73–3.10 (2H, m), 1.25–4.55 (7H, m), 6.59 (1H, d, J=7.5Hz), 6.82 (2H, d, J=8.5Hz), 6.92 (1H, m), 7.03–7.40 (10H, m), 7.44–7.58 (2H, m), 8.02 (1H, d, J=7.5Hz)

44) 5-Carboxymethyl-1-{4-[2-(4-methylphenyl)benzoylamino] benzoyl}-2,3-dihydro-1H-1-benzazepine NMR (CDCl$_3$, δ): 2.31 (3H, s), 2.37 (1H, m), 2.55 (1H, m), 3.36 (1H, m), 3.44 (1H, d, J=17.5Hz), 3.84 (1H, d, J=17.5Hz), 4.70 (1H, m), 6.20 (1H, t, J=5Hz), 6.59 (1H, d, J=7.5Hz), 6.79–6.94 (3H, m), 7.02–7.54 (12H, m), 7.54 (1H, d, J=7.5Hz)

Example 14

A solution of 1-(t-Butoxycarbonylmethyl)-4-{4-[2-(4methylphenyl)benzoylamino] benzoyl}-1,2,3,4-tetrahydroquinoxalin -2-one (370 mg) in aqueous trifluoroacetic acid (15 ml) was stirred at ambient temperature for 2 hours and the solvent was evaporated in vacuo. The residue was dissolved in chloroform and the solution was washed with water and brine, and dried over magnesium sulfate. The solvent was evaporated in vacuo and the residue was purified by silica gel column (2% methanol in chloroform). The solvent was evaporated in vacuo and the residue was solidified with diethyl ether to give 1-carboxymethyl 4-{4-[2-(4-methylphenyl)benzoylamino]benzoyl}-1,2,3,4 -tetrahydroquinoxalin-2-one (283 mg) as a white powder.

NMR (CDCl$_3$+ CD$_3$OD, δ): 2.36 (3H, s), 4.60 (2H, s), 4.73 (2H, s), 6.70 (1H, d, J=8Hz), 6.82 (1H, t, J=8Hz), 6.97 (1H, d, J=8Hz), 7.10–7.57 (13H, m), 7.76 (1H, d, J=8Hz)

Example 15

To a solution of 1-carboxymethyl-5-{ 4-[ 2-(4 -methylphenyl)benzoylamino]benzoyl}-1,3,4,5-tetrahydro -1,5-benzodiazepin-2(2H)-one (90 mg), N-methylpiperazine (17 mg) and 1-hydroxybenzotriazole (27 mg) in N,N-dimethylformamide (4 ml) was added 1-(3-dimethylaminopropyl)-3-ethylcarbodiimide hydrochloride (39 mg) at ambient temperature and the mixture was stirred at the same temperature for 1.5 hours. The resulting mixture was diluted with ethyl acetate and then the solution was washed with saturated sodium bicarbonate aqueous solution and brine. Drying over magnesium sulfate, filtering and the removal of solvents afforded a crude product. The crude product was triturated with a mixture of diethyl ether and n-hexane (1:1) to give 5-{4-[2-(4-methylphenyl)benzoylamino]benzoyl} -1-[(4-methyl-1-piperazinyl)carbonylmethyl] -1,3,4,5-tetrahydro-1,5-benzodiazepin-2(2H)-one (100 mg) as a white powder.

mp: 161°–163° C.

NMR (CDCl$_3$, δ): 2.35 (3H, s), 2.39 (3H, s), 2.40–2.95 (6H, m), 3.55–3.90 (5H, m), 4.10 (1H, d, J=16Hz), 4.71 (1H, dt, J=5, 10Hz), 5.18 (1H, d, J=16Hz), 6.72 (1H, d, J=8Hz), 6.88–7.60 (14H, m), 7.80 (1H, dd, J=1, 8Hz)

Example 16

The following compounds were obtained according to a similar manner to that of Example 15.

1) 5-{4-[2-(2-Methylphenyl)benzoylamino]benzoyl}-1-[(4 -methyl-1-piperazinyl)carbonylmethyl]-1,3,4,5 -tetrahydro-1,5-benzodiazepin-2(2H)-one mp: 150°–154° C.

NMR (CDCl₃, δ): 2.07 and 2.10 (total 3H, s), 2.38 (3H, s), 2.40–2.68 (4H, m), 2.72–2.95 (1H, m), 3.56–3.88 (6H, m), 4.09 (1H, dd, J=1, 15Hz), 4.60–4.80 (1H, m), 5.18 (1H, dd, J=1, 15Hz), 6.65–6.75 (1H, br), 6.82–7.00 (3H, m), 7.06 (2H, d, J=8Hz), 7.17–7.40 (7H, m), 7.53 (2H, ddt, J=1, 9, 15Hz), 8.10 (1H, d, J=7Hz)

2) 1-(3-Dimethylpropylaminocarbonylmethyl)-5-{4-[2-(2methylphenyl)benzoylamino] benzoyl}-1,3,4,5 -tetrahydro-1,5-benzodiazepin-2(2H)-one mp: 115°–120° C.

NMR (CDCl₃, δ): 1.60–1.75 (2H, m), 2.08 (3H, s), 2.20 (3H, s), 2.38 (2H, t, J=6Hz), 2.55–2.80 (2H, m), 3.30–3.55 (2H, m), 3.80 (1H, dd, J=5, 13Hz), 4.03 (1H, d, J=16Hz), 4.60–4.80 (1H, m), 4.83 (1H, d, J=16Hz), 6.70 (1H, d, J=8Hz), 6.85 (2H, d, J=9Hz), 6.90–7.40 (8H, m), 7.48–7.62 (3H, m), 7.68–7.80 (1H, br), 8.10 (1H, dd, J=1, 8Hz)

3) 5-{4-[2-(2,4-Dimethylphenyl)benzoylamino]benzoyl}-1 -[(4-methyl-1-piperazinyl)carbonylmethyl]-1,3,4,5 -tetrahydro-1,5-benzodiazepin-2 (2H)-one NMR (CDCl₃, δ): 1.97 and 2.01 (total 3H, s), 2.33 (3H, s), 2.38 (3H, s), 2.42–2.56 (5H, m), 2.81 (1H, m), 3.56–3.87 (5H, m), 4.05 (1H, d, J=17.5Hz), 4.71 (1H, m), 5.69 (1H, d, J=17.5Hz), 6.69 (1H, br), 6.85 (1H, d, J=8.5Hz), 6.93 (1H, m), 7.02–7.26 (8H, m), 7.36 (1H, dd, J=8, 1Hz), 7.44–7.60 (2H, m), 8.06 (1H, d, J=8Hz)

4) 5-{4-[2-(2-Methylphenyl)benzoylamino]benzoyl}-1-[ 2-(4-methyl-1-piperazinyl)carbonylethyl]-1,3,4,5 -tetrahydro-1,5-benzodiazepin-2(2H)-one NMR (CDCl₃, δ): 2.08 (3H, br s), 2.30 (3H, s), 2.22–3.02 (8H, m), 3.40–3.90 (5H, m), 4.05–4.33 (2H, m), 4.52–4.82 (1H, m), 6.60–7.22 (5H, m), 7.23–7.67 (11H, m), 8.09 (1H, br d, J=9Hz)

5) 5-{4-[2-(2-Methylphenyl)benzoylamino]benzoyl}-1-{3 -(4-methyl-1-piperazinyl)carbonylpropyl]-1,3,4,5 -tetrahydro-1, 5-benzodiazepin-2 (2H)-one NMR (CDCl₃, δ): 1.89–2.80 (13H, m), 2.28 (3H, s), 3.31–3.51 (2H, m), 3.51–3.68 (2H, m), 3.70–3.87 (1H, m), 3.88–4.10 (2H, m), 4.50–4.80 (1H, m), 6.53–7.66 (16H, m), 8.07 (1H, br d, J=9Hz)

6) 5-{4-[2-(2-Methylphenyl)benzoylamino]benzoyl} -1-[1-(4-methyl-1-piperazinyl)carbonylethyl]-1,3,4,5 -tetrahydro-1,5-benzodiazepin-2 (2H) one NMR (CDCl₃, δ): 1.24–1.43 (3H, m), 1.97–2.15 (3H, m), 2.36 (3H, s), 2.38–2.77 (6H, m), 3.43–4.06 (5H, m), 4.45–4.71 (1H, m), 5.64 (1H, q, J=8Hz), 6.56–7.67 (15H, m), 7.95–8.18 (2H, m)

7) 7,8-Dimethyl-5-{4-[2-(4-methylphenyl)benzoylamino]benzoyl} -1-[(4-methyl-1-piperazinyl)carbonylmethyl] -1,3,4,5-tetrahydro-1,5-benzodiazepin-2(2H)-one NMR (CDCl₃, δ): 1.98 (3H, s), 2.20 (3H, s), 2.36 (3H, s), 2.38 (3H, s), 2.40–2.63 (5H, m), 2.69–2.88 (1H, m), 3.55–3.83 (5H, m), 4.05 (1H, d, J=16Hz), 4.57–4.78 (1H, m), 5.10 (1H, d, J=16Hz), 6.41–6.47 (1H, br s), 6.99 (3H, d, J=8Hz), 7.09–7.36 (7H, m), 7.38–7.59 (3H, m), 7.83 (1H, dd, J=1, 7Hz)

8) 7-Methyl-5-{4-[2-(4-methylphenyl)benzoylamino] benzoyl} -1-[(4-methyl-1-piperazinyl)carbonylmethyl] -1,3,4,5-tetrahydro-1,5-benzodiazepin-2(2H)-one NMR (CDCl₃, δ): 2.09 (3H, s), 2.35 (3H, s), 2.38 (3H, s), 2.40–2.63 (5H, m), 2.72–2.90 (1H, m), 3.56–3.86 (5H, m), 4.06 (1H, d, J=16Hz), 4.60–4.78 (1H, m), 5.12 (1H, d, J=16Hz), 6.48–6.53 (1H, br s), 6.96–7.36 (11H, m), 7.38–7.59 (3H, m), 7.83 (1H, dd, J=1, 8Hz)

9) 8-Chloro-5-{4-[2-(4-methylphenyl)benzoylamino] benzoyl} -1-[(4-methyl-1-piperazinyl)carbonylmethyl] -1,3,4,5-tetrahydro-1,5-benzodiazepin-2(2H)-one NMR (CDCl₃, δ): 2.38 (3H, s), 2.39 (3H, s), 2.44–2.92 (6H, m), 3.58–3.87 (5H, m), 4.06 (1H, d, J=16Hz), 4.59–4.77 (1H, m), 5.03 (1H, d, J=16Hz), 6.65 (1H, d, J=9Hz), 6.89–7.35 (11H, m), 7.39–7.59 (3H, m), 7.83 (1H, dd, J=1, 8Hz)

10) 8-Chloro-5-{3-methyl-4-[2-(4-methylphenyl)benzoylamino] benzoyl}-1-[(4-methyl-1-piperazinyl)carbonylmethyl] -1,3,4,5-tetrahydro-1,5-benzodiazepine-2(2H)one NMR (CDCl₃, δ): 1.46 (3H, s), 2.37 (6H, s), 2.42–2.90 (6H, m), 3.49–3.87 (5H, m), 4.05 (1H, d, J=15Hz), 4.59–4.78 (1H, m), 5.17 (1H, d, J=15Hz), 6.61–6.74 (2H, m), 6.89–6.98 (2H, m), 7.18–7.58 (8H, m), 7.84 (1H, dd, J=1, 8Hz), 8.08 (1H, d, J=8Hz)

11) 8-Chloro-5-{3-methoxy-4-[2-(4-methylphenyl)benzoylamino] benzoyl}-1-[(4-methyl-1-piperazinyl)carbonylmethyl] -1,3,4,5-tetrahydro-1,5-benzodiazepin-2 (2H)-one NMR (CDCl₃, δ): 2.38 (6H, s), 2.40–2.80 (6H, m), 3.50–3.88 (5H, m), 3.54 (3H, s), 4.06 (1H, d, J=15Hz), 4.58–4.76 (1H, m), 5.13 (1H, d, J=15Hz), 6.42 (1H, d, J=8Hz), 6.68 (1H, d, J=9Hz), 6.94 (1H, dd, J=1, 9Hz), 7.04 (1H, s), 7.17 (2H, d, J=8Hz), 7.26–7.59 (5H, m), 7.80 (2H, d, J=8Hz), 8.20 (1H, d, J=9Hz)

12) 5-{3-Methoxy-4-[2-(4-methylphenyl)benzoylamino] benzoyl} -8-methyl-1-[(4-methyl-1-piperazinyl)carbonylmethyl] -1,3,4,5-tetrahydro-1,5-benzodiazepin -2(2H)-one NMR (CDCl₃, δ): 2.29 (3H, s), 2.36 (6H, s), 2.43–2.67 (5H, m), 2.73–2.92 (1H, m), 3.50–3.84 (5H, m), 3.57 (3H, s), 4.04 (1H, d, J=16Hz), 4.60–4.79 (1H, m), 5.14 (1H, d, J=16Hz), 6.39 (1H, d, J=8Hz), 6.60 (1H, d, J=8Hz), 6.75 (1H, d, J=8Hz), 7.08 (1H, d, J=1Hz), 7.16 (3H, d, J=6Hz), 7.25–7.32 (2H, m), 7.38–7.59 (3H, m), 7.77–7.82 (2H, m), 8.16 (1H, d, J=9Hz)

13) 5-{4-[2-(2,4-Dimethylphenyl)benzoylamino]-3-methoxybenzoyl} -8-methyl-1-[(4-methyl-1-piperazinyl)carbonylmethyl] -1,3,4,5-tetrahydro-1,5-benzodiazepin -2(2H)-one NMR (CDCl₃, δ) 2.03 and 2.13 (total 3H, s), 2.29 (3H, s), 2.32 (3H, s), 2.33 (3H, s), 2.43–2.66 (5H, m), 2.72–2.91 (1H, m), 3.50–3.86 (5H, m), 3.57 (3H, s), 4.03 (1H, d, J=15Hz), 4.59–4.78 (1H, m), 5.15 (1H, dd, J=5, 15Hz), 6.26–6.41 (1H, br), 6.58 (1H, d, J=8Hz), 6.72 (1H, d, J=8Hz), 6.99–7.26 (6H, m), 7.40–7.58 (2H, m), 7.88–7.95 (1H, br s), 7.94 (1H, dd, J=1, 6Hz), 8.08 (1H, d, J=8Hz)

14) 8-Methyl-5-{4-[2-(4-methylphenyl)benzoylamino] benzoyl} -1-[(4-methyl-1-piperazinyl)carbonylmethyl] 1,3,4,5-tetrahydro-1,5 -benzodiazepin-2(2H)-one NMR CDCl₃, δ): 2.30 (3H, s), 2.37 (3H, s), 2.39 (3H, s), 2.41–2.6 7 (5H, m), 2.70–2.91 (1H, m), 3.57–3.84 (5H, m), 4.06 (1H, d, J=16Hz), 4.60–4.79 (1H, m) 5.13 (1H, d, J=16Hz), 6.59 (1H, d, J=8Hz), 6 .74 (1H, d, J=8Hz), 6.94–7.04 (3H, m), 7.07–7.3 5 (7H, m), 7.38–7.59 (3H, m), 7.82 (1H, dd, J=1, 7Hz)

15) 8-Methyl-5-{3-methyl-4-[2-(4-methylphenyl)benzoylamino] benzoyl}-1-[(4-methyl-1-piperazinyl)carbonylmethyl] -1,3,4,5-tetrahydro-1,5-benzodiazepin -2(2H)-one NMR (CDCl₃, δ): 1.46 (3H, s), 2.30 (3H, s), 2.37 (6H, s), 2.40–2.68 (6H, m), 3.55–3.86 (5H, m), 4.06 (1H, d, J=15Hz), 4.60–4.78 (1H, m), 5.18 (1H, d, J=15Hz), 6.55–6.80 (3H, m), 6.90 (1H, s), 7.19 (3H, d, J=9Hz), 7.22–7.59 (5H, m), 7.82 (1H, dd, J=1, 8Hz), 8.02 (1H, d, J=9Hz)

16) 8-Methoxy-5-{4-[2-(4-methylphenyl)benzoylamino] -benzoyl}-1-[(4-methyl-1-piperazinyl)carbonylmethyl] -1,3,4,5-tetrahydro-1,5-benzodiazepin-2(2H)-one NMR (CDCl₃, δ): 2.37 (3H, s), 2.39 (3H, s), 2.40–2.67 (5H, m), 2.73–2.92 (1H, m), 3.55–3.82 (5H, m), 3.78 (3H, s), 4.04 (1H, d, J=16Hz), 4.60–4.78 (1H, m), 5.15 (1H, d, J=16Hz), 6.48 (1H, d, J=8Hz), 6.60 (1H, d, J=8Hz), 6.92–7.13 (6H, m), 7.18–7.36 (4H, m), 7.38–7.58 (3H, m), 7.82 (1H, dd, J=1, 8Hz)

17) 5-{3-Chloro-4-[2-(2-methylphenyl)benzoylamino]-benzoyl}-1-[(4-methyl-1-piperazinyl)carbonylmethyl]-1,3,4,5-tetrahydro-1,5-benzodiazepin-2(2H)-one NMR (CDCl₃, δ): 2.13 and 2.15 (total 3H, s), 2.36 (3H, s), 2.41–2.72 (5H, m), 2.84 (1H, dt, J=7, 14Hz), 3.48–3.91 (5H, m), 4.07 (1H, d, J=16Hz), 4.70 (1H, dt, J=7, 14Hz), 5.16 (1H, d, J=16Hz), 6.65–7.11 (3H, m), 7.16–7.64 (10H, m), 7.69 (1H, br s), 7.94 (1H, d, J=8Hz), 8.25 (1H, d, J=8Hz)

18) 5-{3-Chloro-4-[2-(2-methylphenyl)benzoylamino]-benzoyl}-1-[(4-dimethylamino-1-piperidyl)carbonylmethyl]-1,3,4,5-tetrahydro-1,5-benzodiazepin-2(2H)one NMR (CDCl₃, δ): 1.38–2.05 (4H, m), 2.11 and 2.14 (total 3H, s), 2.34 (6H, s), 2.30–2.52 (1H, m), 2.53–2.97 (3H, m), 3.01–3.34 (1H, m), 3.70–4.20 (3H, m), 4.56–4.80 (2H, m), 5.09–5.28 (1H, m), 6.64–7.04 (3H, m), 7.12–7.63 (10H, m), 7.69 (1H, br s), 7.93 (1H, d, J=8Hz), 8.25 (1H, d, J=8Hz)

19) 5-{3-Chloro-4-[2-(2,4-dimethylphenyl)benzoylamino]benzoyl}-1-[(4-methyl-1-piperazinyl)carbonylmethyl]-1,3,4,5-tetrahydro-1,5-benzodiazepin-2(2H)-one NMR (CDCl₃, δ): 2.06 and 2.12 (total 3H, s), 2.33 (3H, s), 2.36 (3H, s), 2.40–2.71 (5H, m), 2.83 (1H, dt, J=13, 6 Hz), 3.48–3.90 (5H, m), 4.08 (1H, d, J=16Hz), 4.70 (1H, dt, J=13, 6 Hz), 5.16 (1H, d, J=16Hz), 6.64–7.61 (12H, m), 7.69–7.80 (1H, m), 7.93 (1H, d, J=8Hz), 8.27 (1H, d, J=8Hz)

20) 5-{2-Chloro-4-[2-(2,4-dimethylphenyl)benzoylamino]-benzoyl}-1-[(4-methyl-1-piperazinyl)carbonylmethyl]-1,3,4,5-tetrahydro-1,5-benzodiazepin-2(2H)-one NMR (CDCl₃, δ): 1.98 and 2.02 (total 3H, s), 2.36 (3H, s), 2.41 (3H, s), 2.27–2.70 (5H, m), 2.82 (1H, dt, J=7, 14Hz), 3.44–3.96 (6H, m), 4.89 (1H, dt, J=7, 14Hz), 5.16 (1H, d, J=16Hz), 6.62–7.03 (4H, m), 7.04–7.33 (8H, m), 7.43–7.63 (2H, m), 8.05 (1H, d, J=9Hz)

21) 5-{4-[2-(2-Methylphenyl)benzoylamino]-3-nitrobenzoyl}-1-[(4-methyl-1-piperazinyl)carbonylmethyl]-1,3,4,5-tetrahydro-1,5-benzodiazepin-2(2H)-one NMR (CDCl₃, δ): 2.16 and 2.18 (total 3H, s), 2.36 (3H, s), 2.39–2.75 (5H, m), 2.87 (1H, dt, J=7, 14Hz), 3.48–3.95 (5H, m), 4.26 (1H, d, J=16Hz), 4.73 (1H, dt, J=7, 14Hz), 5.13 (1H, d, J=16Hz), 6.71 (1H, d, J=9Hz), 6.88–7.42 (8H, m), 7.43–7.69 (3H, m), 7.72–7.91 (2H, m), 8.63 (1H, d, J=9Hz), 10.02 (1H, s)

22) 5-{4-[2-(2,4-Dimethylphenyl)benzoylamino]-2-nitrobenzoyl}-1-[(4-methyl-1-piperazinyl)carbonylmethyl]-1,3,4,5-tetrahydro-1,5-benzodiazepin-2(2H)-one NMR (CDCl₃, δ): 2.00 and 2.03 (total 3H, s), 2.36 (3H, s), 2.42 (3H, s), 2.30–2.70 (5H, m), 2.82 (1H, dt, J=6, 15Hz), 3.46–3.90 (5H, m), 3.95 (1H, d, J=16Hz), 4.94 (1H, dt, J=5, 13Hz), 5.17 (1H, d, J=16Hz), 6.80–7.07 (2H, m), 7.11–7.72 (12H, m), 8.10 (1H, d, J=9Hz)

23) 5-{3-Methoxy-4-[2-(2-methylphenyl)benzoylamino]benzoyl}-1-[(4-methyl-1-piperazinyl)carbonylmethyl]-1,3,4,5-tetrahydro-1,5-benzodiazepin-2(2H)-one NMR (CDCl₃, δ): 2.09 and 2.16 (total 3H, s), 2.37 (3H, s), 2.40–2.72 (5H, m), 2.84 (1H, dt, J=7, 13Hz), 3.57 (3H, s), 3.51–3.91 (5H, m), 4.06 (1H, d, J=16Hz), 4.71 (1H, dt, J=7, 13Hz), 5.21 (1H, d, J=16Hz), 6.29–6.48 (1H, m), 6.65–6.78 (1H, m), 6.86–7.07 (2H, m), 7.14–7.33 (6H, m), 7.35 (1H, d, J=9Hz), 7.43–7.60 (2H, m), 7.85 (1H, br s), 7.95 (1H, d, J=9Hz), 8.16 (1H, d, J=9Hz)

24) 5-{3-Methoxy-4-[2-(4-methylphenyl)benzoylamino]benzoyl}-1-[(4-methyl-1-piperazinyl)carbonylmethyl]-1,3,4,5-tetrahydro-1,5-benzodiazepin-2(2H)-one NMR (CDCl₃, δ): 2.36 (6H, s), 2.41–2.72 (5H, m), 2.85 (1H, dt, J=7, 14Hz), 3.53 (3H, s), 3.55–3.92 (5H, m), 4.06 (1H, d, J=16Hz), 4.72 (1H, dt, J=5, 14Hz), 5.19 (1H, d, J=16Hz), 6.42 (1H, d, J=9Hz), 6.74 (1H, d, J=9Hz), 6.90–7.07 (2H, m), 7.11–7.22 (2H, m), 7.23–7.60 (7H, m), 7.73–7.86 (2H, m), 8.16 (1H, d, J=9Hz)

25) 1-[(4-Dimethylamino-1-piperidyl)carbonylmethyl]-5-{3-methoxy-4-[2-(2-methylphenyl)benzoylamino]benzoyl}-1,3,4,5-tetrahydro-1,5-benzodiazepin-2(2H)-one NMR CDCl₃, δ): 1.36–2.20 (4H, m), 2.09 and 2.16 (total 3H, s), 2.34 (6H, s), 2.30–2.97 (10H, m), 3.02–3.32 (1H, m), 3.53 and 3.56 (total 3H, s), 3.66–4.18 (3H, m), 4.57–4.81 (2H, m), 5.07–5.31 (1H, m), 6.26–6.48 (1H, m), 6.64–6.78 (1H, m), 6.85–7.07 (2H, m), 7.08–7.41 (7H, m), 7.42–7.60 (2H, m), 7.85 (1H, br s), 7.95 (1H, d, J=9Hz), 8.15 (1H, d, J=9Hz)

26) 5-{3-Methoxy-4-[2-(2,4-dimethylphenyl)benzoylamino]benzoyl}-1-[(4-methyl-1-piperazinyl)carbonylmethyl]-1,3,4,5-tetrahydro-1,5-benzodiazepin-2(2H)-one NMR (CDCl₃, δ): 2.03 and 2.12 (total 3H, s), 2.34 (3H, s), 2.36 (3H, s), 2.40–2.72 (5H, m), 2.73–2.96 (1H, m), 3.47–3.92 (5H, m), 3.56 (3H, s), 4.05 (1H, d, J=16Hz), 4.71 (1H, dt, J=5, 14Hz), 5.20 (1H, d, J=16Hz), 6.28–6.46 (1H, m), 6.65–6.79 (1H, m), 6.86–7.30 (7H, m), 7.36 (1H, d, J=9Hz), 7.40–7.58 (2H, m), 7.84–8.00 (2H, m), 8.18 (1H, d, J=9Hz)

27) 1-(Carbamoylmethyl)carbamoylmethyl-5-{4-[2-(2,4dimethylphenyl)benzoylamino]-3-methoxybenzoyl}-1,3,4,5-tetrahydro-1,5-benzodiazepin-2(2H)-one NMR (CDCl₃, δ): 2.04 and 2.10 (total 3H, s), 2.34 (3H, s), 2.47–2.88 (2H, m), 3.48 and 3.50 (total 3H, s), 3.73–3.96 (2H, m), 4.02–4.33 (2H, m), 4.56–4.81 (2H, m), 5.69 (1H, br s), 6.49–6.93 (3H, m), 6.94–7.38 (6H, m), 7.40–7.60 (3H, m), 7.89 (1H, br s), 7.97 (1H, d, J=9Hz), 8.22 (1H, d, J=9Hz)

28) 1-[(4-Dimethylamino-1-piperidyl)carbonylmethyl]-5-{3-methoxy-4-[2-(2,4-dimethylphenyl)benzoylamino]benzoyl}-1,3,4,5-tetrahydro-1,5-benzodiazepin-2(2H)-one NMR (CDCl₃, δ): 1.37–2.15 (4H, m), 2.04 and 2.13 (total 3H, s), 2.34 (9H, s), 2.38–2.99 (4H, m), 3.04–3.32 (1H, m), 3.56 and 3.59 (total 3H, s), 3.72–4.19 (3H, m), 4.56–4.82 (2H, m), 5.09–5.30 (1H, m), 6.25–6.50 (1H, m), 6.64–6.70 (1H, m), 6.88–7.60 (10H, m), 7.83–8.02 (2H, m), 8.18 (1H, d, J=9Hz)

29) 1-[(4-Dimethylamino-1-piperidyl)carbonylmethyl]-5-{4-[2-(2,6-dimethylphenyl)benzoylamino]benzoyl}-1,3,4,5-tetrahydro-1,5-benzodiazepin-2(2H)-one NMR (CDCl₃, δ): 1.43–2.14 (4H, m), 1.99 (3H, s), 2.01 (3H, s), 2.32 (6H, s), 2.35–2.94 (4H, m), 3.04–3.31 (1H, m), 3.80 (1H, dd, J=5, 13Hz), 3.90–4.18 (2H, m), 4.57–4.80 (2H, m), 5.20 dd, J=10, 15Hz), 6.59 (1H, d, J=8Hz), 6.82 (3H, m), 7.03 (2H, d, J=9Hz), 7.12–7.40 7.43–7.65 (3H, m), 8.26 (1H, dd, J=1, 8H 30) 5-{4-[2-(2-Methylphenyl)benzoylamino]benzoymethyl-1-piperazinyl)carbamoylmethyl]-1,3,-tetrahydro-1,5-benzodiazepin-2(2H)-one NMR (CDCl₃, δ): 2.06 (3H, s), 2.31 and 2.36 (total 3H, s), 2.52–2.90 (8H, m), 3.04–3.38 (2H, m), 3.81 (1H, dd, J=5, 11Hz), 4.07 (1H, d, J=16Hz), 4.60–4.78 (1H, m), 5.38 (1H, d, J=16Hz), 6.38–6.43 (1H, br s), 6.63–6.75 (1H, br), 6.82–7.17 (5H, m), 7.18–7.46 (6H, m), 7.48–7.64 (3H, m), 8.02–8.12 (1H, m)

31) 1-[ (2-Dimethylaminoethyl)carbamoylmethyl ]-5-{ 4-[ 2 -(2methylphenylbenzoylamino] benzoyl } -1,3,4,5 -tetrahydro -1,5 -benzodiazepin-2 (2H )-one NMR (CDCl$_3$, δ): 2.08 (3H, s), 2.22 (6H, s), 2.41 (2H, t, J=6Hz), 2.53–2.84 (2H, m), 3.27–3.45 (2H, m), 3.82 (1H, dd, J=5, 12Hz), 4.21 (1H, d, J=15Hz), 4.60–4.77 (1H, m), 4.72 (1H, d, J=15Hz), 6.70 (1H, d, J=7Hz), 6.82–7.12 (7H, m), 7.23–7. 39 (4H, m), 7.48–7.60 (3H, m), 8.08 (1H, dd, J=1, 7Hz)

32) 5-{ 4-[ 2-(2-Methylphenyl)benzoylamino]benzoyl }-1-{ [ 2( -(4-morpholinyl) ethyl ] carbamoylmethyl } -1,3,4,5 -tetrahydro-1,5-benzodiazepin-2(2H)-one NMR (CDCl$_3$, δ): 2.09 (3H, s), 2.35–2.50 (6H, m), 2.56–2.83 (2H, m), 3.20–3.48 (2H, m), 3.70 (4H, t, J=5Hz), 3.82 (1H , dd, J=5, 12Hz), 4.24 (1H, dd, J=3, 15Hz), 4.6 3–4.80 (2H, m), 6.71 (1H, d, J=9Hz), 6.80–7.16 (7H, m), 7.22–7.39 (4H, m), 7.48–7.60 (3H, m), 8.08 (1H, dd, J=1, 7Hz)

33) 5-{4-[2-(2-Methylphenyl)benzoylamino]benzoyl}-1-[(4morpholinyl)carbamoylmethyl]   -1,3,4,5-tetrahydro-1,5 -benzodiazepin-2(2H)-one NMR (CDCl$_3$, δ): 2.03 –2.10 (3H, br s), 2.53–2.88 (5H, m), 3.74–3.9 4 (5H, m), 4.10 (1H, d, J=15Hz), 4.60–4.7 8 (2H, m), 5.38 (1H, d, J=15Hz), 6.43–6.4 8 (1H, br s), 6.65–6.76 (1H, br), 6.90 (2H, d, J=8Hz), 7.00–7.13 (3H, m), 7.16–7.46 (7H, m), 7.50–7.61 (3H, m), 8.07 (1H, dd, J=1, 8Hz)

34) 5-{ 4-[ 2-(2-Methylphenyl) benzoylamino]benzoyl }-1-{ [ 2 -(1-piperidyl) ethyl ]carbamoylmethyl} -1,3,4,5 -tetrahydro-1, 5-benzodiazepin-2(2H)-one NMR (CDCl$_3$, δ) 1.40–1.78 (6H, m), 2.08 (3H, s), 2.35–2.49 (6H, m), 2.57–2.85 (2H, m), 3.30–3.50 (2H, m), 3.80 (1H, dd, J=5, 13Hz), 4.14 (1H, d, J=15Hz), 4.62–4.80 (1H, m), 4.81 (1H, d, J=15Hz), 6.70 (1H, d, J=8Hz), 6.86 (2H, d, J=9Hz), 6.90–7.18 (5H, m), 7.22–7.38 (4H, m), 7.47–7.62 (3H, m), 8.08 (1H, dd, J=1, 7Hz)

35) 5-{ 4-[ 2-(2-Methylphenyl) benzoylamino]benzoyl } -1-[ (1piperidyl) -carbamoylmethyl ] -1,3,4,5-tetrahydro-1,5 -benzodiazepin-2(2H)-one NMR (CDCl$_3$, δ): 1.55–1.80 (6H, m), 2.07 (3H, s), 2.30–2.90 (5H, m), 3.81 (1H, dd, J=8, 14Hz), 4.08 (1H, d, J=16Hz), 4.60–4.80 (2H, m), 5.38 (1H, d, J=16Hz), 6.36 (1H, s), 6.62–6.76 (1H, br), 6.82–7.43 (12H, m), 7.46–7.65 (2H, m), 8.08 (1H, d, J=7Hz)

36) 1-[(4-Dimethylamino-1-piperidyl)carbamoylmethyl]-5-{4 -[2-(2-methylphenyl)benzoylamino]benzoyl}-1,3,4,5 -tetrahydro-1,5-benzodiazepin-2(2H)-one NMR (CDCl$_3$, δ): 1.40–1.70 (2H, m), 1.80–2.05 (2H, m), 2.08 (3H, d, J=7Hz), 2.30 (6H, s), 2.25–2.90 (4H, m), 3.05–3.32 (1H, m), 3.72 (1H, dd, J=5, 13Hz), 3.88–4.20 (2H, m), 4.55–4.70 (2H, m), 5.10–5.30 (1H, m), 6.60–6.75 (1H, br), 6.90 (2H, d, J=8Hz), 7.05 (2H, d, J=8Hz), 7.15–7.41 (8H, m), 7.55 (2H, ddd, J=1, 7, 14Hz), 8.08 (1H, d, J=7Hz)

37) 1-[(4-Dimethylamino-1-piperidyl)carbamoylmethyl]-5-{4 -[2-(4-methylphenyl)benzoylamino]benzoyl}-1,3,4,5 -tetrahydro-1,5-benzodiazepin-2(2H)-one NMR (CDCl$_3$, δ): 1.42–1.73 (2H, m), 1.80–2.11 (2H, m), 2.28–2.50 (1H, m), 2.30 (6H, s), 2.38 (3H, s), 2.56–2.93 (3H, m), 3.05–3.30 (1H, m), 3.82 (1H, dd, J=5, 13Hz), 3.90–4.19 (2H, m), 4.58–4.80 (2H, m), 5.21 (1H, dd, J=10, 16Hz), 6.70 (1H, d, J=9Hz), 6.89–7.04 (4H, m), 7.09 (2H, d, J=8Hz), 7.15–7.60 (8H, m), 7.83 (1H, dd, J=1, 8Hz)

38) 1-[ (2-Dimethylaminoethyl)carbamoylmethyl ]-5-{ 4-[ 2-(4methylphenyl)benzoylamino] benzoyl}-1,3,4,5 -tetrahydro-1,5-benzodiazepin-2(2H)-one NMR (CDCl$_3$, δ): 2.20 (6H, s), 2.32–2.41 (2H, m), 2.36 (3H, s), 2.55–2.86 (2H, m), 3.23–3.41 (2H, m), 3.83 (1H, dd, J=5, 13Hz), 4.22 (1H, d, J=15Hz), 4.60–4.72 (1H, m), 4.70 (1H, d, J=15Hz), 6.72 (1H, d, J=9Hz), 6.80–6.89 (1H, br), 6.92–7.03 (4H, m), 7.08 (2H, d, J=9Hz), 7.16–7.25 (2H, m), 7.26–7.59 (5H, m), 7.82 (1H, dd, J=1, 7Hz)

39) 1-[(N',N'-Dimethylhydrazino)carbonylmethyl]-5-{4-[2 -(4-methylphenyl)benzoylamino]benzoyl}-1,3,4,5 -tetrahydro-1,5-benzodiazepin-2(2H)-one NMR (CDCl$_3$, δ): 2.38 and 2.39 (total 3H, s), 2.55 and 2.65 (total 6H, s), 2.66–2.90 (2H, m), 3.82 (1H, dd, J=6, 13Hz), 4.15 (1H, d, J=17Hz), 4.54–4.81 (2H, m), 5.36 (1H, d, J=17Hz), 6.35 (1H, s), 6.71 (1H, d, J=8Hz), 6.90–7.59 (14H, m), 7.82 (1H, dd, J=1, 8Hz)

40) 5-{4-[2-(4-Methylphenyl)benzoylamino]benzoyl}-1-[(4 -methyl-1-piperazinyl)carbonylmethyl]-1,3,4,5 -tetrahydro-1,5-benzodiazepin-2(2H)-one NMR (CDCl$_3$, δ): 2.30 and 2.32 (total 3H, s), 2.38 and 2.39 (total 3H, s), 2.52–2.91 (8H, m), 3.04–3.08 (2H, m), 3.82 (1H, dd, J=5, 12Hz), 4.09 (1H, d, J=17Hz), 4.60–4.80 (1H, m), 5.37 (1H, d, J=17Hz), 6.38–6.41 (1H, br s), 6.68–6.76 (1H, m), 6.90–7.07 (4H, m), 7.08–7.61 (10H, m), 7.82 (1H, dd, J=1, 8Hz)

41) 5-{ 4-[ 2-(4-Methylphenyl) benzoylamino]benzoyl }-1-{ [ 2 -(4-morpholinyl) ethyl ] carbamoylmethyl } -1,3, 4,5 -tetrahydro-1,5-benzodiazepin-2(2H)-one NMR (CDCl$_3$, δ): 2.38 (3H, s), 2.38–2.48 (6H, m), 2.56–2.88 (2H, m), 3.20–3.48 (2H, m), 3.72 (4H, t, J=5Hz), 3.84 (1H, dd, J=5, 13Hz), 4.27 (1H, d, J=15Hz), 4.62–4.83 (2H, m), 4.70 (1H, d, J=15Hz), 6.72 (1H, d, J=7Hz), 6.85–7.12 (6H, m), 7.20 (2H, d, J=9Hz), 7.24–7.59 (6H, m), 7.83 (1H, dd, J=1, 8Hz)

42) 5-{4-[2-(4-Methylphenyl)benzoylamino]benzoyl}-1-[(4morpholinyl)carbamoylmethyl]   -1,3,4,5-tetrahydro-1,5 -benzodiazepin-2 (2H)-one NMR (CDCl$_3$, δ) 2.37 and 2.38 (total 3H, s), 2.53–2.92 (5H, m), 3.00–3.33 (1H, m), 3.72–3.95 (4H, m), 4.13 (2H, d, J=17Hz), 4.58–4.80 (2H, m), 5.37 (1H, d, J=17Hz), 6.48 (1H, s), 6.68–6.78 (1H, br), 6.90–7.09 (4H, m), 7.10–7.60 (10H, m), 7.82 (1H, dd, J=1, 8Hz)

43) 1-{4-[2-(4-Methylphenyl)benzoylamino]benzoyl}-5-[(4 -methyl-1-piperazinyl)carbonylmethoxyimino]-2,3,4,5 -tetrahydro-1H-1-benzazepine NMR (CDCl$_3$, δ): 1.60–1.88 (1H, br s), 1.90–2.21 (1H, br s), 2.28 (3H, s), 2.36 (3H, s), 2.21–2.54 (4H, m), 2.70–3.05 (2H, br s), 3.21–3.75 (5H, m), 4.30–4.65 (1H, br s), 4.90 (2H, s), 6.65 (1H, d, J=8Hz), 6.86–7.60 (15H, m), 7.80 (1H, d, J=8Hz)

44) 5-{3-Hydroxy-4-[2-(4-methylphenyl)benzoylamino] benzoyl} -1-[(4-methyl-1-piperazinyl)carbonylmethyl] -1,3, 4,5-tetrahydro-1,5-benzodiazepin-2(2H)-one NMR (CDCl$_3$, δ): 2.32 (3H, s), 2.36 (3H, s), 2.20–2.66 (5H, m), 2.79 (1H, m), 3.50–3.88 (5H, m), 4.46 (1H, d, J=15Hz), 4.64 (1H, m), 4.96 (1H, d, J=15Hz), 6.62–6.84 (3H, m), 6.90–7.08 (2H, m), 7.09–7.60 (10H, m), 7.78 (1H, d, J=9Hz)

45) 4,4-Dimethyl-5-{4-[2-(4-methylphenyl)benzoylamino]benzoyl} -1-[(4-methyl-1-piperazinyl)carbonylmethyl] -1,3,4,5-tetrahydro-1,5-benzodiazepin-2(2H)-one NMR (CDCl$_3$, δ): 1 .56 (3H, s), 1.62 (3H, s), 1.93 (3H, s), 2.20-2.60 (5H, m), 2.36 (3H, s), 2.70 (1H, d, J=13Hz), 3.60–3.83 (4H, m), 4.10 (1H, d, J=15Hz), 5.24 (1H, d, J=15Hz), 6.69 (1H, dd, J=1, 8Hz), 6.83–6.97 (4H, m), 7.04–7.32 (7H, m), 7.37–7.57 (3H, m), 7.80 (1H, dd, J=1, 8Hz)

46) 4-Methyl-5-{4-[2-(4-methylphenyl)benzoylamino] benzoyl} -1-[(4-methyl-1-piperazinyl)carbonylmethyl] -1,3, 4,5-tetrahydro-1,5-benzodiazepin-2(2H)-one Rf: 0.33 (10% methanol in chloroform)

NMR (CDCl$_3$, δ): 1.27 (3H, d, J=6Hz), 2.38 (3H, s), 2.39 (3H, s), 2.40–2.64 (7H, m), 3.55–3.80 (4H, m), 3.98 (1H, d, J=16Hz), 5.13–5.30 (1H, br), 5.24 (1H, d, J=16Hz), 6.64–6.72 (1H, br), 6.92–7.02 (5H, m), 7.17–7.55 (8H, m), 7.80 (1H, d, J=8Hz)

47) 1-{[4-(2-Hydroxyethyl)-1-piperazinyl]carbonylmethyl} -5-{4-[2-(4-methylphenyl)benzoylamino]benzoyl} -1,3,4,5-tetrahydro-1,5-benzodiazepin-2(2H)-one Rf: 0.19 (chloroform:methanol:acetic acid = 8:2:1) 0.21 (10% methanol in chloroform)

NMR (CDCl$_3$, δ): 2.40 (3H, s), 2.55–2.85 (8H, m), 3.60–3.88 (7H, m), 4.10 (1H, d, J=15Hz), 4.62–4.80 (1H, m), 5.16 (1H, d, J=15Hz), 6.73 (1H, d, J=8Hz), 6.90–7.15 (6H, m), 7.17–7.55 (8H, m), 7.82 (1H, dd, J=1, 8Hz)

48) 5-{4-[2-(4-Methylphenyl)benzoylamino]benzoyl}-1-{[4 -(1-pyrrolidinylcarbonylmethyl)-1-piperazinyl]carbonylmethyl} -1,3,4,5-tetrahydro-1,5 -benzodiazepin-2(2H)-one NMR (CDCl$_3$, δ): 1.82–2.04 (4H, m), 2.38 (3H, s), 2.58–2.85 (6H, m), 3.20 (2H, s), 3.49 (4H, dd, J=8, 13Hz), 3.62–3.88 (5H, m), 4.10 (1H, d, J=16Hz), 4.63–4.80 (1H, m), 5.16 (1H, d, J=16Hz), 6.72 (1H, d, J=8Hz), 6.93–7.15 (4H, m), 7.18–7.58 (10H, m), 7.82 (1H, d, J=8Hz)

49) 1-{[4-(3,4-Methylenedioxybenzyl)-1-piperazinyl] carbonylmethyl} -5-{4-[2-(4-methylphenyl)benzoylamino] benzoyl}-1,3,4,5-tetrahydro-1,5-benzodiazepin -2(2H)-one NMR (CDCl$_3$, δ): 2.37 (3H, s), 2.41–2.68 (5H, m), 2.74–2.85 (1H, m), 3.43–3.86 (8H, m), 4.08 (1H, d, J=16Hz), 4.62–4.79 (1H, m), 5.15 (1H, d, J=16Hz), 5.96 (2H, s), 6.68–6.78 (3H, m), 6.85–7.02 (5H, m), 7.08 (2H, d, J=9Hz), 7.17–7.58 (8H, m), 7.82 (1H, dd, J=1, 8Hz)

50) 5-{4-[2-(4-Methylphenyl)benzoylamino]benzoyl}-1{ [4-(2-pyridyl)-1-piperazinyl]carbonylmethyl} -1,3,4,5-tetrahydro-1,5-benzodiazepin-2(2H)-one NMR (CDCl$_3$, δ): 2.39 (3H, s), 2.63 (1H, dd, J=5, 14Hz), 2.78–2.87 (1H, m), 3.59–3.88 (9H, m), 4.14 (1H, d, J=15Hz), 4.65–4.78 (1H, m), 5.21 (1H, d, J=15Hz), 6.67–6.73 (3H, m), 6.95–7.02 (4H, m), 7.11 (2H, d, J=8Hz), 7.19–7.33 (4H, m), 7.38–7.58 (5H, m), 7.82 (1H, d, J=8Hz), 8.21–8.24 (1H, m)

51) 1-[(4-Methyl-1-homopiperazinyl)carbonylmethyl]-5-{4-[ 2-(4-methylphenyl)benzoylamino]benzoyl}-1,3,4,5 -tetrahydro-1,5-benzodiazepin-2(2H)-one NMR (CDCl$_3$, δ): 1.92–2.11 (2H, m), 2.38 (3H, s), 2.42 and 2.44 (total 3H, s), 2.59–2.72 (4H, m), 2.77–2.89 (2H, m), 3.63–3.87 (5H, m), 4.02 (1H, dd, J=6, 15Hz), 4.64–4.78 (1H, m), 5.18 (1H, dd, J=2, 15Hz), 6.69–6.74 (1H, br), 6.92–7.01 (4H, m), 7.10 (2H, d, J=8Hz), 7.18–7.32 (5H, m), 7.39–7.57 (4H, m), 7.83 (1H, d, J=8Hz)

52) 1-[(4-tert-Butoxycarbonyl-1-piperazinyl)carbonylmethyl] -5-{4-[2-(4-methylphenyl)benzoylamino]benzoyl} -1,3,4,5-tetrahydro-1,5-benzodiazepin-2(2H)-one Rf: 0.79 (10% methanol in chloroform)

53) 1-[(4-Ethoxycarbonylmethyl-1-piperazinyl)carbonylmethyl] -5-{4-[2-(4-methylphenyl)benzoylamino]benzoyl} -1,3,4,5-tetrahydro-1,5-benzodiazepin-2(2H)-one NMR (CDCl$_3$, δ): 1.31 (3H, t, J=8Hz), 2.38 (3H, s), 2.59–2.80 (6H, m), 3.28 (2H, s), 3.63–3.88 (5H, m), 4.17 (1H, d, J=15Hz), 4.21 (2H, dd, J=7, 15Hz), 4.62–4.81 (1H, m), 5.17 (1H, d, J=15Hz), 6.68–6.76 (1H, br), 6.93–7.02 (3H, m), 7.08–7.14 (2H, m), 7.18–7.59 (10H, m), 7.83 (1H, dd, J=1, 8Hz)

54) 5-{4-[2-(4-Methylphenyl)benzoylamino]benzoyl}-1-([4 -(3 -phthalimidopropyl)-1 -piperazinyl ] carbonylmethyl) -1,3,4,5-tetrahydro-1,5-benzodiazepin-2 (2H)-one NMR (CDCl$_3$, δ): 1.90 (2H, q, J=7Hz), 2.38 (3H, s), 2.40–2.67 (7H, m), 2.73–2.92 (1H, m), 3.40–3.58 (4H, m), 3.79–3.88 (3H, m), 4.02 (1H, d, J=15Hz), 4.62–4.79 (1H, m), 5.13 (1H, d, J=15Hz), 6.68–6.76 (1H, m), 6.95–7.15 (6H, m), 7.19–7.58 (9H, m), 7.70–7.79 (2H, m), 7.80–7.90 (3H, m)

55) 5-(4-[2-(4-Methylphenyl)benzoylamino]benzoyl}-1-[(4 -methyl-1-piperazinyl)carbonylmethyl]-8 -trifluoromethyl-1,3,4,5-benzodiazepin-2(2H)-one NMR (CDCl$_3$, δ): 2.37 (3H, s), 2.38 (3H, s), 2.42–2.78 (6H, m), 3.60–3.78 (4H, m), 3.80–3.92 (1H, m), 4.12 (1H, d, J=15Hz), 4.62–4.73 (1H, m), 5.15 (1H, d, J=15Hz), 6.86 (1H, d, J=8Hz), 6.98–7.06 (3H, m), 7.14 (2H, d, J=9Hz), 7.19–7.34 (4H, m), 7.39–7.57 (3H, s), 7.67 (1H, s), 7.84 (1H, d, J=8Hz)

56) 5-{2-Methoxy-4-[2-(4-methylphenyl)benzoylamino] benzoyl} -1-(4-methyl-1-piperazinylcarbonyl)methyl -1,3, 4,5-tetrahydro-1,5-benzodiazepin-2(2H)-one NMR (CDCl$_3$, δ): 2.37 (3H, s), 2.38 (3H, s), 2.75–2.64 (6H, m), 2.80 (1H, m), 3.50–3.86 (5H, m), 3.69 (1H, s), 4.88 (1H, dt, J=5, 15Hz), 5.71 (1H, d, J=16Hz), 6.40 (1H, d, J=7.5Hz), 6.70–6.79 (1H, m), 6.85–6.94 (2H, m), 7.06–7.56 (11H, m), 7.82 (1H, d, J=7.5Hz)

57) 5-{ 6-[ 2-(4-Methylphenyl) benzoylamino] nicotinoyl} -1 -(4-methyl-1-piperazinylcarbonyl)methyl-1,3,4,5 -tetrahydro-1,5-benzodiazepin-2 (2H)-one NMR (CDCl$_3$, δ): 2.32 (3H, s), 2.35 (3H, s), 2.40–2.68 (5H, m), 2.83 (1H, m), 3.57 (2H, m), 3.71 (2H, m), 3.84 (1H, m), 4.18 (1H, d, J=16Hz), 4.72 (1H, dt, J=5, 13Hz), 5.07 (1H, d, J=16Hz), 6.72 (1H, d, J=7.5Hz), 6.98 (1H, m), 7.16 (2H, d, J=8.5Hz), 7.23–7.55 (9H, m), 7.70 (1H, m), 7.97 (1H, m), 8.05 (1H, d, J=7.5Hz)

58) 5-{ 4 -[ 2-(3 -Methylphenyl) benzoylamino] benzoyl} -1-(4 -methyl-1-piperazinylcarbonyl)methyl-1,3,4,5 -tetrahydro-1,5 -benzodiazepin-2 (2H )-one NMR (CDCl$_3$, δ): 2.29 (3H, s), 2.36 (3H, s), 2.41–2.67 (5H, m), 2.82 (1H, m), 3.56–3.87 (5H, m), 4.07 (1H, d, J=16Hz), 4.71 (1H, dt, J=5, 13Hz), 5.70 (1H, d, J=16Hz), 6.69 (1H, d, J=7.5Hz), 6.88–7.00 (3H, m), 7.08 (2H, d, J=8.5Hz), 7.17–7.58 (10H, m), 7.86 (1H, m)

59) 7,8-Dimethyl-5-{4-[2-(2,6-dimethylphenyl)benzoylamino] benzoyl}-1-(4-methyl-1-piperazinylcarbonyl) -methyl-1,3,4,5-tetrahydro-1,5-benzodiazepin-2(2H)-one NMR (CDCl$_3$, δ): 1.95 (3H, s), 1.99 (3H, s), 2.02 (3H, s), 2.19 (3H, s), 2.35 (3H, s), 2.43–2.61 (5H, m), 2.79 (1H, m), 3.50–3.86 (5H, m), 4.01 (1H, d, J=15.5Hz), 4.64 (1H, m), 5.13 (1H, d, J=1, 5.5Hz), 6.44 (1H, br), 6.87 (2H, d, J=8.5Hz), 7.06–3.37 (6H, m), 7.54 (1H, s), 7.55–7.64 (2H, m), 8.28 (1H, dd, J=1.5, 7.5Hz)

60) 5-{4-[2-(4-Methylphenyl)benzoylamino]benzoyl}-1-(4 -methyl-1-piperazinylcarbonyl)methyl-2,3,4,5 -tetrahydro-1H-1,5-benzodiazepine NMR (CDCl$_3$, δ): 1.80–2.18 (2H, m), 2.25–3.56 (4H, m), 2.29 (3H, s), 2.39 (3H, s), 3.00–3.27 (2H, m), 3.41–3.88 (5H, m), 3.98 (1H, d, J=17.5Hz), 4.16 (1H, d, J=17.5Hz), 4.62 (1H, m), 6.52–6.65 (2H, m), 6.82

(1H, d, J=7.5Hz), 6.87–6.96 (3H, m), 7.05–7.55 (10H, m), 7.83 (1H, dd, J=1.5, 7.5Hz)

61) 5-{4-[2-(2,6-Dimethylphenyl)benzoylamino]benzoyl}-1 -(4-methyl-1-piperazinylcarbonyl)methyl-1,3,4,5-tetrahydro-1,5-benzodiazepin-2(2H)-one NMR (CDCl₃, δ): 1.99 (3H, s), 2.04 (3H, s), 2.36 (3H, s), 2.43–2.68 (5H, m), 2.81 (1H, m), 3.56–3.86 (5H, m), 4.05 (1H, d, J=16Hz), 4.69 (1H, m), 5.18 (1H, d, J=16Hz), 6.69 (1H, d, J=7.5Hz), 6.82–6.96 (3H, m), 7.07 (2H, d, J=8.5Hz), 7.12–7.37 (7H, m), 7.44–7.64 (2H, m), 8.28 (1H, dd, J=1.5, 7.5Hz)

62) 5-{4-[N-2-(4-Methylphenyl)benzoyl-N-methyl]aminobenzoyl} -1-(4-methyl-1-piperazinylcarbonyl)methyl-1,3,4,5-tetrahydro-1,5-benzodiazepin-2(2H)one NMR (CDCl₃, δ): 2.35 (3H, s), 2.38 (3H, s), 2.38–2.88 (6H, m), 3.11 (3H, s), 3.47–3.86 (5H, m), 4.02 (1H, d, J=17Hz), 4.67 (1H, m), 5.10 (1H, d, J=17Hz), 5.97 (2H, d, J=8.5Hz), 6.62 (1H, m), 6.69–6.87 (3H, m), 6.94–7.12 (4H, m), 7.21–7.48 (6H, m)

63) 5 -{ 4 -[ 2 -(4 -Methylphenyl) benzoylamino] benzoyl } -1 -(3 -quinuclidinylcarbamoylmethyl)-1,3,4,5-tetrahydro-1,5-benzodiazepin-2 (2H)-one FAB-MASS (m/z): 642 (M+1)

64) 1-{4-[2-(4-Methylphenyl)benzoylamino]benzyl}-5-(4-methyl-1-piperazinylcarbonyl)methyl-1,3,4,5-tetrahydro-1,5-benzodiazepin-2(2H)-one NMR (CDCl₃, δ): 2.26 (3H, s), 2.34 (2H, m), 2.40 (3H, s), 2.53 (2H, t, J=7.5Hz), 3.33 (2H, m), 3.50–3.62 (4H, m), 3.82 (2H, s), 4.87 (2H, m), 6.95–7.23 (9H, m), 7.35–7.56 (7H, m), 7.88 (1H, dd, J=1.5, 7.5Hz)

65) 1-(4-Methyl-1-piperazinylcarbonyl)methyl-5-{4-[2-(2-trifluoromethylphenyl) benzoylamino]benzoyl}-1,3,4,5-tetrahydro-1,5-benzodiazepin-2(2H)-one NMR (CDCl₃, δ): 2.37 (3H, s), 2.40–2.66 (5H, m), 2.82 (1H, m), 3.58 (2H, m), 3.70 (2H, m), 3.77 (1H, m), 4.05 (1H, d, J=16Hz), 4.70 (1H, m), 5.69 (1H, d, J=16Hz), 6.70 (1H, d, J=7.5Hz), 6.93 (1H, t, J=7.5Hz), 7.00–7.11 (4H, m), 7.15–7.36 (5H, m), 7.43–7.60 (4H, m), 7.73–7.81 (2H, m)

66) 1-(4-Methyl-1-piperazinylcarbonyl)methyl-5-(4-[2-(2,4,6-trimethylphenyl)benzoylamino]benzoyl}-1,3,4,5-tetrahydro-1,5-benzodiazepin-2(2H)-one NMR (CDCl₃, δ): 1.92 (3H, s), 1.99 (3H, s), 2.36 (3H, s), 2.40 (3H, s), 2.42–2.67 (4H, m), 2.83 (1H, m), 3.59 (2H, m), 3.72 (2H, m), 3.80 (1H, m), 4.04 (1H, d, J=17Hz), 4.70 (1H, m), 5.20 (1H, d, J=17Hz), 6.69 (1H, d, J=7.5Hz), 6.75 (2H, d, J=8.5Hz), 6.92 (1H, m), 7.02–7.23 (5H, m), 7.34 (1H, dd, J=1.5, 7.5Hz), 7.44–7.60 (3H, m), 8.25 (1H, dd, J=1.5, 7.5Hz)

67) 5-{ 2-Methyl-4-[ 2-(4-methylphenyl) benzoylamino] -benzoyl } -1-(4-methyl-1-piperazinylcarbonyl) methyl -1,3,4,5-tetrahydro-1,5-benzodiazepin-2 (2H)-one FAB-MASS (m/z): 630 (M+1)

68) 7-Chloro-1-{4-[2-(4-methylphenyl)benzoylamino] -benzoyl}-5-(4-methyl-1-piperazinylcarbonyl)methyl -2,3,4,5-tetrahydro-1H-1-benzazepine NMR (CDCl₃, δ): 2.35 (6H, s×2), 2.41 (2H, t, J=5Hz), 2.48 (2H, t, J=5Hz), 3.55–3.72 (4H, m), 1.25–4.50 (7H, m), 6.52 (1H, d, J=7.5Hz), 6.86–7.08 (4H, m), 7.14–7.54 (10H, m), 7.83 (1H, d, J=7.5Hz)

69) 1-{4-[2-(4-Methylphenyl)benzoylamino]benzoyl}-5-(4 -methyl-1-piperazinylcarbonyl)methyl-2,3,4,5 -tetrahydro-1H-1-benzazepine FAB-MASS (m/z): 601 (M+1)

70)1-{4-[2-(2-Methylphenyl)benzoylamino]benzoyl}-5-(4 -methyl-1-piperazinylcarbonyl)methyl-2,3,4,5 -tetrahydro-1H-1 -benzazepine FAB-MASS (m/z): 601 (M+ 1)

71) 1-{4-[2-(4-Methylphenyl)benzoylamino]benzoyl}-5-(4methyl -1 -piperazinylcarbonyl) methyl -2,3 -dihydro-1H -1 -benzazepine FAB-MASS (m/z): 599 (M+1)

Example 17

A mixture of 1-(4-aminobenzoyl)-1,2,3,4-tetrahydroquinoline (252 mg), diphenic anhydride (224 mg), triethylamine (202 mg) and catalytic amount of 4-dimethylaminopyridine in dichloromethane (15 ml) was stirred for 8 hours at ambient temperature. The mixture was evaporated in vacuo and diluted with ethyl acetate and washed with saturated sodium hydrogen carbonate aqueous solution, brine, and dried over magnesium sulfate. The solvent was evaporated in vacuo and triturated from ethyl acetate to give 1-{4-[2-(2-carboxyphenyl)benzoylamino]benzoyl} -1,2,3,4-tetrahydroquinoline (400 mg).

NMR (CDCl₃+ CD₃OD, δ): 1.92–2.13 (2H, m), 2.81 (2H, t, J=7Hz), 3.85 (2H, t, J=7Hz), 6.64 (1H, d, J=9Hz), 6.85 (1H, dd, J=9, 9Hz), 7.00 (1H, dd, J=9, 9Hz), 7.07–7.26 (8H, m), 7.31–7.57 (5H, m), 7.65–7.77 (1H, m), 7.77–7.86 (1H, m)

Example 18

To a solution of acetyl chloride (1 ml) and methanol (20 ml) was added 1-{4-[2-(2-carboxyphenyl)benzoylamino] benzoyl} -1,2,3,4-tetrahydroquinoline (350 mg) at 0° C. The solution was stirred for 30 minutes at the same temperature and then stirred for 3 hours at ambient temperature. The solvent was evaporated in vacuo and triturated from dichloromethane to give 1-{4-[2-(2methoxycarbonylphenyl)benzoylamino] benzoyl}-1,2,3,4tetrahydroquinoline (300 mg).

NMR (CDCl₃, δ): 1.95–2.11 (2H, m), 2.81 (2H, t, J=7Hz), 3.83 (3H, s), 3.78–3.95 (2H, m), 6.66 (1H, br d, J=9Hz), 6.85 (1H, dd, J=9, 9Hz), 6.99 (1H, dd, J=9, 9Hz), 7.03–7.29 (6H, m), 7.32–7.60 (5H, m), 7.72–7.83 (2H, m), 8.68 (1H, br s)

Example 19

A solution of 1-{4-[2-(2-methoxycarbonylphenyl)benzoylamino] benzoyl}-1,2,3,4-tetrahydroquinoline (300 mg) and dry tetrahydrofuran (15 ml) was cooled to 0° C., and lithium aluminum hydride (46 mg) was added. The reaction mixture was maintained at 0° C. for 1 hour, and then was quenched by adding 1N hydrochloric acid. The resulting mixture was filtered through a bed of celite, diluted with ethyl acetate, washed with brine, dried over magnesium sulfate, and concentrated. Purification of the residue by column chromatography (silica gel, 15 g; ethyl acetate-n-hexane, 1:2) gave 1-{4-[2-(2-hydroxymethylphenyl)benzoylamino] benzoyl}-1,2,3,4-tetrahydroquinoline (80 mg) as a amorphous.

NMR (CDCl₃, δ): 1.90–2.10 (2H, m), 2.83 (2H, t, J=7Hz), 2.96 (1H, br s), 3.84 (2H, t, J=7Hz), 4.51 (1H, br d, J=1, 1Hz), 4.93 (1H, br d, J=1, 1Hz), 6.66 (1H, d, J=8Hz), 6.85 (1H, dd, J=8, 8Hz), 6.98 (1H, dd, J=8, 8Hz), 7.05–7.86 (13H, m), 8.86 (1H, br s)

Example 20

The following compound was obtained according to a similar manner to that of Example 4.

5-{4-[2-(2-Methylphenyl)benzoylamino]benzoyl}-1-(4-pyridylcarbamoyl)methyl-1,3,4,5-tetrahydro-1,5-benzodiazepin-2(2H)-one NMR (CDCl₃, δ): 2.29 (3H, s), 2.36 (3H, s), 2.41–2.67 (5H, m), 2.82 (1H, m), 3.56–3.87 (5H, m), 4.07 (1H, d, J=16Hz), 4.71 (1H, dt, J=5, 13Hz), 5.70 (1H, d, J=16Hz), 6.69 (1H, d, J=7.5Hz), 6.88–7.00 (3H, m), 7.08 (2H, d, J=8.5Hz), 7.17–7.58 (10H, m), 7.86 (1H, m)

Example 21

To a solution of 1-carboxymethyl-5-{4-[2-(2-methylphenyl)benzoylamino] benzoyl}-1,3,4,5-tetrahydro-1,5-benzodiazepin-2(2H)-one (220 mg), 2-dimethylaminoethanol (37 mg) and 4-dimethylaminopyridine (10 mg) in dichloromethane (5 ml) were added dicyclohexylcarbodiimide (102 mg) at ambient temperature and the mixture was stirred at the same temperature for 30 hours. The resulting mixture was washed with saturated sodium bicarbonate aqueous solution. Drying over magnesium sulfate, filtering and the removal of solvents afforded a crude product. The crude product was purified by silica gel column (3% methanol in chloroform). The solvent was evaporated in vacuo and the residue was solidified with diethyl ether to give 1-[(2-dimethylaminoethoxy)carbonylmethyl] -5-{4-[2-(2-methylphenyl)benzoylamino]benzoyl} -1,3,4,5-tetrahydro-1,5-benzodiazepin-2(2H)-one (86 mg) as a white powder.

NMR (CDCl₃, δ): 2.08 (3H, s), 2.30 (6H, s), 2.55–2.85 (4H, m), 3.72–3.88 (1H, m), 4.22 (1H, d, J=18Hz), 4.33 (2H, d, J=6Hz), 4.70 (1H, dt, J=5, 14Hz), 4.90 (1H, d, J=18Hz), 6.65–7.62 (15H, m), 8.10 (1H, d, J=9Hz)

Example 22

The following compound was obtained according to a similar manner to that of Example 21.

1-[(2-Dimethylaminoethoxy) carbonylmethyl ] -5-{ 4-[ 2-(4-methylphenyl)benzoylamino] benzoyl }-1,3,4,5-tetrahydro -1,5-benzodiazepin-2 (2H)-one NMR (CDCl₃, δ): 2.32 (6H, s), 2.37 (3H, s), 2.56–2.81 (2H, m), 2.63 (2H, t, J=5Hz), 3.83 (1H, dd, J=5, 11Hz), 4.25 (1H, d, J=18Hz), 4.34 (2H, t, J=5Hz), 4.61–4.80 (1H, m), 4.89 (1H, d, J=1, 8Hz), 6.74 (1H, d, J=8Hz), 6.96 (4H, d, J=9Hz), 7.10 (2H, d, J=8Hz), 7.16–7.36 (5H, m), 7.38–7.59 (3H, m), 7.83 (1H, dd, J=1, 8Hz)

Example 23

To a solution of 2-(4-methylphenyl)benzoic acid (240 mg) in dichloromethane (5 ml) was added oxalyl chloride (0.2 ml) and a few drop of N,N-dimethylformamide and the solution was stirred at 0° C. for 30 minutes. Dichloromethane was evaporated in vacuo to give a crude acid chloride as an oil. The crude acid chloride was added to a mixture of 1,5-bis(4-aminobenzoyl)-2,3,4,5-tetrhydro-1H-1,5-benzodiazepine (218 mg) and triethylamine (171 mg) in dichloromethane (5 ml) at 0° C. The mixture was stirred at ambient temperature for 18 hours, and then the resulting mixture was washed successively with 0.5N hydrochloric acid and saturated aqueous sodium bicarbonate solution. Drying, filtering and the removal of solvents afford a crude product. The crude product was subjected to silica gel column (eluent: 1% methanol in chloroform) to give 1,5-bis(4-[2-(4-methylphenyl)benzoylamino] -benzoyl}-2,3,4,5-tetrahydro-1H-1,5-benzodiazepine (300 mg) as a white powder.

Rf: 0.61 (10% methanol in chloroform)
NMR (DMSO-d₆, ): 2.23–2.45 (6H, m), 2.28 (6H, s), 7.12–7.26 (6H, m), 7.28–7.40 (6H, m), 7.42–7.60 (16H, m)

Example 24

To a solution of 3-chloro-4-[2-(2-methylphenyl)benzoylamino] benzoic acid (309 mg), diphenyl chlorophosphate (251 mg), 1-ethoxycarbonylmethyl-1,3,4,5-tetrahydro-1,5-benzodiazepin-2(2H)-one (210 mg) in tetrahydrofuran (15 ml) was added triethylamine (172 mg) at 0° C. The resulting mixture was allowed to warm to ambient temperature where it was maintained for 5 hours. The solvent was evaporated and diluted with ethyl acetate and washed with water, diluted hydrochloric acid, saturated sodium bicarbonate aqueous solution and brine. The organic layer was dried over magnesium sulfate and concentrated to give 5-{3-chloro-4-[2-(2-methylphenyl)benzoylamino] benzoyl}-1-ethoxycarbonylmethyl-1,3,4,5-tetrahydro-1,5-benzodiazepin-2(2H)-one (390 mg) which was purified by recrystallization from a mixture of ethyl acetate and n-hexane.

NMR (CDCl₃, δ): 1.31 (3H, t, J=7Hz), 2.12 and 2.14 (total 3H, s), 2.52–2.89 (2H, m), 3.72–3.93 (1H, m), 4.15–4.40 (3H, m), 4.56–4.89 (2H, m), 6.72 (1H, br d, J=8Hz), 6.84–7.09 (2H, m), 7.11–7.40 (8H, m), 7.42–7.76 (3H, m), 7.95 (1H, d, J=8Hz), 8.16–8.35 (1H, m)

Example 25

The following compounds were obtained according to a similar manner to that of Example 24.

1) 5-{3-Chloro-4-[2-(2,4-dimethylphenyl)benzoylamino] benzoyl} -1-ethoxycarbonylmethyl-1,3,4,5-tetrahydro -1,5-benzodiazepin-2(2H)-one NMR (CDCl₃, δ): 1.31 (3H, t, J=7Hz), 2.08 and 2.11 (total 3H, s), 2.33 (3H, s), 2.54–2.90 (2H, m), 3.74–3.92 (1H, m), 4.17–4.40 (3H, m), 4.60–4.86 (1H, m), 4.78 (1H, d, J=17Hz), 6.75 (1H, br d, J=8Hz), 6.85–7.41 (8H, m), 7.41–7.63 (2H, m), 7.72 (1H, br s), 7.90–8.01 (2H, m), 8.22–8.37 (1H, m)

2) 1-Ethoxycarbonylmethyl-5-{4-[2-(2-methylphenyl)benzoylamino] -3-nitrobenzoyl}-1,3,4,5-tetrahydro -1,5-benzodiazepin-2(2H)-one NMR (CDCl₃, δ): 1.30 (3H, t, J=7Hz), 2.17 and 2.18 (total 3H, s), 2.58–2.92 (2H, m), 3.77–3.95 (1H, m), 4.25 (2H, q, J=7Hz), 4.41 (1H, d, J=16Hz), 4.63–4.82 (1H, m), 4.77 (1H, d, J=16Hz), 6.71 (1H, br d, J=8Hz), 6.92–7.73 (11H, m), 7.75–7.93 (2H, m), 8.62 (1H, d, J=8Hz), 10.02 (1H, br s)

3) 1-Ethoxycarbonylmethyl-5-{4-[2-(2,4-dimethylphenyl)benzoylamino] -2-nitrobenzoyl}-1,3,4,5-tetrahydro-1,5-benzodiazepin-2(2H)-one NMR (CDCl₃, δ): 1.35 (3H, t, J=7Hz), 2.01 and 2.03 (total 3H, s), 2.45 (3H, s), 2.55–2.89 (2H, m), 3.73–3.92 (1H, m), 4.18–4.39 (3H, m), 4.84 (1H, d, J=16Hz), 4.82–5.03 (1H, m), 6.84–7.00 (1H, m), 7.03–7.68 (13H, m), 8.08 (1H, d, J=9Hz)

Example 26

To a solution of 6-[2-(4-methylphenyl)benzoylamino] nicotinic acid (332 mg) in dichloromethane (5 ml) were added oxalyl chloride (153 mg) and a few drop of N,N-dimethylformamide and the solution was stirred at ambient temperature for 2 hours. Dichloromethane was evaporated in vacuo to give an acid chloride as an oil and the oil was added to a mixture of 1-ethoxycarbonylmethyl -1,3,4,5-tetrahydro-1,5-benzodiazepin-2(2H)-one (249 mg) and triethylamine (0.167 ml) in dichloromethane (20 ml). The mixture was stirred at ambient temperature for 2 hours and washed successively with 1N hydrochloric acid, water and brine, and dried over magnesium sulfate. The solvent was evaporated in vacuo to give an oil and the oil was subjected to a silica gel column (30 g, 2% methanol in chloroform) to give 1-ethoxycarbonylmethyl-5-(6-[2-(4methylphenyl)benzoylamino] nicotinoyl}-1,3,4,5-tetrahydro -1,5-benzodiazepin-2(2H)-one (250 mg).

NMR (CDCl$_3$, δ): 1.15–1.33 (3H, m), 2.34 (3H, s), 2.54–2.88 (2H, m), 3.85 (1H, m), 4.17–4.40 (3H, m), 4.65–4.82 (2H, m), 6.74 (1H, d, J=7.5Hz), 7.00 (1H, m), 7.16 (2H, d, J=8.5Hz), 7.20–7.35 (3H, m), 7.38–7.46 (2H, m), 7.48–7.58 (2H, m), 7.70 (1H, m), 7.87 (1H, s), 7.98–8.07 (2H, m)

Example 27

The following compound was obtained according to a similar manner to that of Example 26.

1-Ethoxycarbonylmethyl-5-{2-methoxy-4-[2-(4methylphenyl)benzoylamino] benzoyl}-1,3,4,5-tetrahydro-1,5 -benzodiazepin-2(2H)-one NMR (CDCl$_3$, δ): 1.27–1.40 (3H, m), 2.33–2.42 (3H, m), 2.52–2.90 (2H, m), 3.40–3.95 (5H, m), 4.20–4.40 (2H, m), 4.77–5.01 (2H, m), 6.77–7.93 (16H, m)

Example 28

A mixture of 1-(2-acetoxyethyl)-5-{4-[2-(4-methylphenyl)benzoylamino] benzoyl}-1,3,4,5-tetrahydro-1,5 -benzodiazepin-2(2H)-one (450 mg) and potassium carbonate (117 mg) in methanol (15 ml) was stirred at ambient temperature for 3 hours. The mixture was diluted with chloroform and the solution was washed with water and brine, and dried over magnesium sulfate. The solvent was evaporated in vacuo to give 1-(2-hydroxyethyl)-5-{4-[2 -(4-methylphenyl)benzoylamino]benzoyl}-1,3,4,5-tetrahydro -1,5-benzodiazepin-2(2H)-one (430 mg).

NMR (CDCl$_3$, δ): 2.36 (3H, s), 2.42–2.76 (2H, m), 3.75–4.20 (5H, m), 4.63 (1H, m), 6.93–7.10 (3H, m), 7.07–7.58 (13H, m), 7.81 (1H, d, J=7.5Hz)

Example.29

To a solution of 1-{4-[2-(2-methylphenyl)benzoylamino] benzoyl}-2,3,4,5-tetrahydro-1H-1-benzazepin-5-one (620 mg) in methanol (20 ml) was added sodium borohydride (49.4 mg) and the mixture was stirred at ambient temperature for 4 hours. The mixture was diluted with chloroform and the solution was washed with water and brine, and dried over magnesium sulfate. The solvent was evaporated in vacuo to give a syrup and the residue was purified by silica gel column (30g, 1% methanol in chloroform) to give 5-hydroxy-1-{4-[2-(2-methylphenyl)benzoylamino] benzoyl}-2,3,4,5-tetrahydro-1H-1-benzazepine (580 mg).

NMR (CDCl$_3$, δ): 1.61–1.89 (2H, m), 2.04 (3H, s), 2.21 (1H, m), 2.50 (1H, m), 2.76 (1H, m), 4.73–5.65 (2H, m), 6.56 (1H, d, J=7.5Hz), 6.81 (2H, d, J=8.5Hz), 6.90–7.37 (11H, m), 7.44–7.66 (3H, m), 8.08 (1H, d, J=7.5Hz)

Example 30

To a solution of oxalyl chloride (0.134 ml) in dichloromethane (10 ml) was added dimethyl sulfoxide (0.109 ml) at −78° C. and the mixture was stirred at the same temperature. After 10 minutes, 1-(2-hydroxyethyl) -5-{4-[2-(4-methylphenyl)benzoylamino]benzoyl}-1,3,4,5 -tetrahydro-1,5-benzodiazepin-2(2H)-one (400 mg) in dichloromethane (10 ml) was added dropwise at −78° C. and the mixture was stirred at the same temperature for 30 minutes. To the mixture was added triethylamine (0.537 ml) and the mixture was allowed to ambient temperature. The solution was washed with water and brine, and dried over magnesium sulfate. The solvent was evaporated in vacuo to give 1-formylmethyl-5-{4-[2-(4-methylphenyl)benzoylamino] benzoyl}-1,3,4,5-tetrahydro-1,5 -benzodiazepin-2(2H)-one (301 mg) as an unstable oil. The oil was used for next step without further purification.

Example 31

To a mixture of 1-formylmethyl-5-{4-[2-(4-methylphenyl)benzoylamino] benzoyl}-1,3,4,5-tetrahydro-1,5 -benzodiazepin-2(2H)-one (380 mg) and 4-methylpiperazine (73.4 mg) in a mixture of methanol (10 ml) and acetic acid (0.5 ml) was added sodium cyanoborohydride (46.1 mg) and the mixture was stirred at ambient temperature for 5 hours. The mixture was poured into a mixture of chloroform and saturated aqueous sodium hydrogen carbonate and the mixture was stirred at ambient temperature for 30 minutes. The solution was extracted with chloroform and washed with brine, and dried over magnesium sulfate. The solvent was evaporated in vacuo and the residue was subjected to a silica gel column (20g, 5% methanol in chloroform). The solvent was evaporated in vacuo and the residue was solidified with diethyl ether to give 5-{4-[2-(4-methylphenyl)benzoylamino]benzoyl}-1-[2-(4 -methyl-1-piperazinyl)ethyl]-1,3,4,5-tetrahydro-1,5 -benzodiazepin-2(2H)-one (115 mg).

NMR (CDCl$_3$, δ): 2.30 (3H, s), 2.38 (3H, s), 2.41–2.91 (12H, m), 3.78 (1H, dd, J=6, 12.5Hz), 4.00 (2H, m), 4.67 (1H, dt, J=6, 12.5Hz), 6.72 (1H, br d, J=7.5Hz), 6.90–7.02 (3H, m), 7.10–7.56 (11H, m), 7.83 (1H, dd, J=1.5, 7.5Hz)

Example 32

To a solution of 1-[(4-tert-butoxycarbonyl-1piperazinyl)carbonylmethyl] -5-{4-[2-(4-methylphenyl)benzoylamino] benzoyl}-1,3,4,5-tetrahydro-1,5 -benzodiazepin-2(2H)-one (150 mg) in ethyl acetate (5 ml) was added 4N hydrogen chloride - ethyl acetate solution, and then the mixture was stirred at ambient temperature for 12 hours. The solvents were evaporated in vacuo and the residue was diluted with saturated aqueous sodium bicarbonate solution, and then the aqueous layer was extracted with ethyl acetate. Drying, filtering and the removal of solvents afforded a crude product. The crude product was chromatographed on silica gel (20% methanol in chloroform) to give 5-{4-[2-(4-methylphenyl)benzoylamino]benzoyl} -1-[(1-piperazinyl)carbonylmethyl]-1,3,4,5 -tetrahydro-1,5-benzodiazepin-2(2H)-one (58 mg) as a white powder.

NMR (CDCl$_3$, δ): 2.38 (3H, s), 2.63 (1H, dd, J=3, 15Hz), 2.77–3.06 (5H, m), 3.53–3.60 (2H, br), 3.66–3.72 (2H, m), 3.81 (1H, dd, J=7, 14Hz), 4.08 (1H, d, J=t5Hz), 4.66–4.78 (1H, m), 5.17 (1H, d, J=15Hz), 6.68–6.75 (1H, br), 6.93–7.01 (3H, m), 7.09 (2H, d, J=8Hz), 7.20 (2H, d, J=9Hz), 7.24–7.32 (3H, m), 7.35–7.43 (3H, m), 7.45–7.57 (2H, m), 7.82 (1H, dd, J=1, 8Hz)

Example 33

To a solution of 1-[[4-(2-hydroxyethyl)-1-piperazinyl] carbonylmethyl}-5-{4-[2-(4-methylphenyl)benzoylamino] benzoyl}-1,3,4,5-tetrahydro-1,5 -benzodiazepin-2(2H)-one (178 mg) and triethylamine (31 mg) in dichloromethane (4 ml) was added acetic anhydride (31 mg) and the mixture was stirred at ambient temperature for 1.5 hours. To the mixture was added 4-dimethylaminopyridine (10 mg) and acetic anhydride (10 mg), and then the mixture was stirred at ambient temperature for 15 minutes. The resulting mixture was diluted with dichloromethane and the organic layer was washed successively with saturated aqueous sodium bicarbonate solution and brine. Drying, filtering and the removal of solvents afforded a crude product. The crude product was triturated with a mixture of diethyl ether and n-hexane (1:1) to give 1-{[4-(2-acetoxyethyl)-1-piperazinyl] -carbonylmethyl)-5-{4-[2-(4-methylphenyl)benzoylamino] -benzoyl}-1,3,4,5-tetrahydro-1,5-benzodiazepin-2(2H)-one (205 mg) as a slightly-yellow powder.

NMR (CDCl$_3$, δ): 2.09 (3H, s), 2.39 (3H, s), 2.54–2.90 (8H, m), 3.58–3.88 (5H, m), 4.10 (1H, d, J=16Hz), 4.23 (2H, t, J=6Hz), 4.63–4.80 (1H, m), 5.16 (1H, d, J=16Hz), 6.72 (1H, d, J=8Hz), 6.90–7.15 (7H, m), 7.18–7.58 (7H, m), 7.82 (1H, dd, J=1, 8Hz)

Example 34

A solution of 5-(4-[2-(4-methylphenyl)benzoylamino] -benzoyl}-1,3,4,5-tetrahydro-1,5-benzodiazepine-2(2H)thione (460 mg), 3-dimethylaminopropyl chloride hydrochloride (740 mg), potassium carbonate (1.29 g) and sodium iodide (catalytic amount) in acetone (40 ml) was stirred for 19 hours at 60° C. The mixture was filtered and the filtrate was evaporated. The residue was purified by column chromatography (SiO$_2$ 30 g, 5% methanol in chloroform) to give 2-[3-(dimethylamino)propylthio]-5-{4-[2-(4-methylphenyl)benzoylamino] benzoyl}-4,5-dihydro-3H-1,5benzodiazepine (200 mg).

NMR (CDCl$_3$, δ): 1.92 (2H, s), 2.24 (6H, s), 2.35 (3H, s), 2.32–2.50 (2H, m), 2.54–2.94 (2H, m), 3.17 (2H, t, J=7Hz), 3.79–3.94 (1H, m), 4.66–4.88 (1H, m), 6.60 (1H, d, J=9Hz), 6.77 (1H, dd, J=9, 9Hz), 6.87–7.32 (11H, m), 7.33–7.57 (3H, m), 7.80 (1H, d, J=9Hz)

Example 35

A solution of 5-{3-hydroxy-4-[2-(4-methylphenyl)benzoylamino] benzoyl}-1-[(4-methyl-1-piperazinyl)carbonylmethyl] -1,3,4,5-tetrahydro-1,5-benzodiazepin-2(2H)-one (350 mg), 3-dimethylaminopropyl chloride hydrochloride (96.4 mg) and potassium carbonate (230 mg) in N,N-dimethylformamide (15 ml) were stirred for 4 hours at 80° C. The mixture was diluted with ethyl acetate and washed with water, saturated aqueous sodium bicarbonate and brine. The organic solution was dried over sodium sulfate, concentrated, and purified by silica gel column chromatography (SiO$_2$ 10 g, 15% methanol in chloroform) to give 5-{3-dimethylaminopropoxy-4-[2-(4-methylphenyl)benzoylamino] benzoyl}-1-[(4-methyl-1-piperazinyl)carbonylmethyl] -1,3,4,5-tetrahydro-1,5-benzodiazepin -(2H)-one (150 mg).

NMR (CDCl$_3$, δ): 1.74 (2H, s), 2.15 (6H, s), 2.32 (3H, s), 2.33 (3H, s), 2.08–2.67 (7H, m), 2.82 (1H, m), 3.46–3.92 (7H, m), 4.06 (1H, d, J=15Hz), 4.69 (1H, m), 5.18 (1H, d, J=15Hz), 6.43 (1H, br d, J=9Hz), 6.72 (1H, br d, J=9Hz), 6.96 (1H, dd, J=9, 9Hz), 7.00–7.56 (10H, m), 7.68 (1H, d, J=9Hz), 7.86 (1H, s), 8.16 (1H, d, J=9Hz)

Example 36

To a solution of 1-ethoxycarbonylmethyl-5-{4-[2-(4methylphenyl)benzoylamino] benzoyl}-1,3,4,5-tetrahydro-1,5 -benzodiazepin-2(2H)-one (377 mg) in N,N-dimethylformamide (5 ml) was added sodium hydride (60% in oil, 19.3 mg) and the mixture was stirred at ambient temperature for 30 minutes. Methyl iodide (143 mg) was added to the solution and the mixture was stirred at ambient temperature for 8 hours. The mixture was diluted with ethyl acetate and washed successively with 1N hydrochloric acid, aqueous sodium hydrogen carbonate and brine, and dried over magnesium sulfate. The solvent was evaporated in vacuo and the residue was purified by silica gel column (20g, 1% methanol in chloroform) to give 1-ethoxycarbonylmethyl-5-{ 4-[N-2-(4-methylphenyl)benzoyl-N-methyl]aminobenzoyl} -1,3,4, 5-tetrahydro-1,5-benzodiazepin-2(2H)-one (390 mg).

NMR (CDCl$_3$, δ): 1.33 (3H, t, J=7.5Hz), 2.39 (3H, s), 2.52–2.82 (2H, m), 3.10 (3H, s), 3.77 (1H, m), 4.08–4.34 (3H, m), 4.66 (1H, m), 4.78 (1H, d, J=17Hz), 5.99 (2H, d, J=8.5Hz), 6.61–6.84 (4H, m), 6.93–7.10 (4H, m), 7.21–7.33 (5H, m), 7.47 (1H, m)

Example 37

A solution of 5-{4-[2-(4-methylphenyl)benzoylamino] benzoyl} -1-[(4-methyl-1-piperazinyl)carbonylmethyl] -1,3, 4,5-tetrahydro-1,5-benzodiazepin-2(2H)-one (130 mg), ditert-butyldicarbonate (150 mg), triethylamine (64 mg) and 4-dimethylaminopyridine (catalytic amount) in acetone (10 ml) was stirred for 5 hours at ambient temperature. The solvent was washed with water, saturated sodium bicarbonate aqueous solution and brine, and dried over sodium sulfate. The solvent was evaporated and purified by silica gel column chromatography (30 g, 5% methanol in chloroform) to give 5-{4-[N-tert-butoxycarbonyl-2-(4 -methylphenyl)benzoylamino]benzoyl}-1-[(4-methyl-1piperazinyl)carbonylmethyl] -1,3,4,5-tetrahydro-1,5 -benzodiazepin-2(2H)-one (120 mg).

NMR (CDCl$_3$, δ): 1.12 (9H, s), 2.34 (3H, s), 2.41 (3H, s), 2.38–2.69 (5H, m), 2.76–2.94 (1H, m), 3.51–3.71 (3H, m), 3.72–3.90 (2H, m), 4.07 (1H, d, J=15Hz), 4.64–4.83 (1H, m), 5.14 (1H, d, J=15Hz), 6.60–6.80 (3H, m), 6.88–7.01 (1H, m), 7.12–7.53 (12H, m)

Example 38

A mixture of 5-{4-[2-(4-methylphenyl)benzoylamino] benzoyl} -1-(4-methyl-1-piperazinylcarbonyl)methyl-1,3, 4,5 -tetrahydro-1,5-benzodiazepin-2(2H)-one (110 mg) and methyl iodide (76.1 mg) in dichloromethane (10 ml) was stirred at ambient temperature overnight and a precipitate was filtered to give 4-{ 5-{4-[2-(4-methylphenyl)benzoylamino]benzoyl} -2-oxo-1,3,4 ,5-tetrahydro-2H-1,5-benzodiazepin-1-yl) acetyl-1,1-dimethylpiperazinium iodide (118 mg).

NMR (DMSO-d$_6$, δ): 2.29 (3H, s), 2.44–2.71 (2H, m), 3.19 6H, s), 3.38–3.56 (4H, m), 3.72 (1H, m), 3.87–4.02 (4H, m), 4.41 (1H, m), 4.48 (1H, d, J=17.5Hz), 5.60 (1H, d, J=17.5Hz), 6.84 (1H, d, J=7.5Hz), 7.02 (1H, m), 7.08–7.17 (4H, m), 7.25–7.31 (4H, m), 7.37–7.56 (7H, m)

Example 39

To a solution of 5-{4-[2-(4-methylphenyl)benzoylamino]benzoyl}-1-(4-methyl-1-piperazinylcarbonyl)-methyl-1,3,4,5-tetrahydro-1,5-benzodiazepin-2(2H)-one (12.2 g) in hot ethanol (125 ml) was added sulfuric acid (972 mg) in ethanol (10 ml) and the solution was gently stirred at 80° C. for 1 hour. The solution was cooled to ambient temperature and the precipitated solid was filtered and dried in air to give 5-4-[2-(4-methylphenyl)benzoylamino]benzoyl}-1-(4-methyl 1-piperazinylcarbonyl)methyl-1,3,4,5-tetrahydro-1,5-benzodiazepin-2(2H)-one ½ sulfate (12.1 g).

NMR (DMSO-$d_6$, δ): 2.28 (3H, s), 2.43–3.81 (11H, m), 2.59 (3H, s), 4.45 (1H, m), 4.52 (1H, d, J=17.5Hz), 5.07 (1H, d, J=17.5Hz), 6.82 (1H, d, J=7.5Hz), 7.01 (1H, m), 7.07–7.60 (15H, m)

Example 40

To a solution of 5-{4-[2-(4-methylphenyl)benzoylamino]benzoyl}-1-(4-methyl-1-piperazinylcarbonyl)methyl-1,3,4,5-tetrahydro-1,5-benzodiazepin-2(2H)-one (12.2 g) in hot ethanol (125 ml) was added methanesulfonic acid (1.90 g) in ethanol (10 ml). The solution was cooled to ambient temperature and the precipitated solid was filtered and dried in air to give 5-{4-[2-(4-methylphenyl)benzoylamino]benzoyl}-1-(4-methyl-1-piperazinylcarbonyl)-methyl-1,3,4,5-tetrahydro-1,5-benzodiazepin-2(2H)-one methanesulfonate (13.7 g).

NMR (DMSO-$d_6$, δ): 2.26 (3H, s), 2.32 (3H, s), 2.43–3.60 (10H, m), 2.73 (3H, s), 3.71 (1H, m), 4.36–4.57 (2H, m), 5.10 (1H, d, J=17.5Hz), 6.80 (1H, d, J=7.5Hz), 7.00 (1H, m), 7.09–7.58 (15H, m), 9.80 (1H, br)

What we claim is:

1. A compound of the formula:

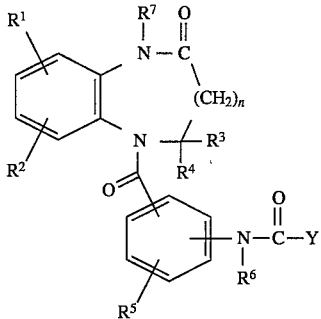

wherein $R^1$ is hydrogen or lower alkyl, $R^2$ is hydrogen, lower alkyl, halo(lower) alkyl, halogen or lower alkoxy, $R^3$ and $R^4$ are each hydrogen, lower alkyl or taken together to form oxo, $R^5$ is hydrogen, halogen, nitro, hydroxy, protected hydroxy, lower alkyl, or lower alkoxy optionally substituted with lower alkylamino or di(lower)alkyl amino, $R^6$ is hydrogen, lower alkyl or acyl, $R^7$ is hydrogen; lower alkyl optionally substituted with halogen, amino, lower alkylamino, di(lower)alkylamino, protected amino, acyl, a heterocyclic group, hydroxy or protected hydroxy; or acyl;

Y is

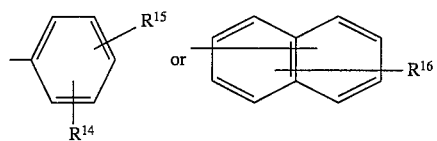

wherein $R^{14}$ is hydrogen, halogen, hydroxy or lower alkoxy;

$R^{15}$ is aryloxy, naphthyl, phenyl substituted with substituent(s) selected from the group consisting of lower alkyl, lower alkoxy, halogen, halo(lower)alkyl, hydroxy, amino(lower)alkyl, azido(lower)alkyl, lower alkylamino(lower)alkyl, di(lower)alkylamino(lower)alkyl, acylamino(lower)alkyl, hydroxy(lower)alkyl, cyano and acyl, or a heterocyclic group, and $R^{16}$ is aryl; and n is 0, 1, 2 or 3, and pharmaceutically acceptable salts thereof.

2. The compound of claim 1, wherein $R^1$ is hydrogen; $R^2$ is hydrogen, lower alkyl or halogen; $R^3$ is hydrogen; $R^4$ is hydrogen; $R^5$ is hydrogen or lower alkoxy; $R^6$ is hydrogen; $R^7$ is hydrogen or lower alkyl optionally substituted with amino, lower alkylamino, di(lower)alkylamino, protected amino, acyl or a heterocyclic group; Y is

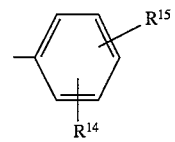

wherein $R^{14}$ and $R^{15}$ are as defined above, and n is 0, 1 or 2.

3. The compound of claim 2, wherein $R^7$ is lower alkyl optionally substituted with amino, lower alkylamino, di(lower)alkylamino, protected amino, acyl or piperidino; Y is

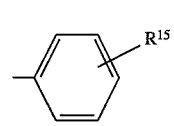

wherein $R^{15}$ is phenyl substituted with substituent(s) selected from the group consisting of lower alkyl, lower alkoxy, halogen, halo(lower)alkyl, hydroxy, amino(lower)alkyl, azido(lower)alkyl, lower alkylamino(lower)alkyl, di(lower)alkylamino(lower) alkyl, acylamino (lower) alkyl, hydroxy(lower)alkyl, cyano and acyl.

4. The compound of claim 3, wherein $R^7$ is lower alkyl substituted with N-lower alkylpiperazinylcarbonyl or lower alkyl substituted with di(lower)alkylamino; and $R^{15}$ is phenyl substituted with lower alkyl or di(lower alkyl).

5. The compound of claim 4, wherein $R^2$ is hydrogen; $R^5$ is hydrogen; $R^7$ is lower alkyl substituted with N-lower alkylpiperazinylcarbonyl; $R^{15}$ is phenyl substituted with lower alkyl or di(lower alkyl), and n is 1.

6. The compound of claim 5, which is 5-{4-(2-(4-methylphenyl)benzoylamino)benzoyl}-1-((4-methyl-1-piperazinyl)carbonylmethyl)-1,3,4,5-benzodiazepin-2(2H)-one.

7. A pharmaceutical composition comprising the compound of claim 1 together with a pharmaceutically acceptable substantially non-toxic carrier or excipient.

8. A method of therapeutic treatment or prevention of hypertension, heart failure, renal insufficiency, edema, ascites, vasopressin parasecretion syndrome, hepatocirrhosis, hyponatremia, hypokalemia, diabetic or circulation disorders which comprises administering an effective amount of the compound of claim 1 to a human being or animal in need thereof.

* * * * *